US008039474B2

(12) United States Patent
Fecher et al.

(10) Patent No.: US 8,039,474 B2
(45) Date of Patent: Oct. 18, 2011

(54) 2,3,4,9-TETRAHYDRO-1*H*-CARBAZOLE DERIVATIVES AS CRTH2 RECEPTOR ANTAGONISTS

(75) Inventors: Anja Fecher, Basel (CH); Heinz Fretz, Riehen (CH); Markus Riederer, Liestal (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 1068 days.

(21) Appl. No.: 11/722,095

(22) PCT Filed: Dec. 22, 2005

(86) PCT No.: PCT/IB2005/054380

§ 371 (c)(1),
(2), (4) Date: Jun. 19, 2007

(87) PCT Pub. No.: WO2006/070325

PCT Pub. Date: Jul. 6, 2006

(65) Prior Publication Data

US 2009/0270414 A1    Oct. 29, 2009

(30) Foreign Application Priority Data

Dec. 27, 2004 (WO) .................. PCT/EP2004/014719

(51) Int. Cl.
*A61K 31/473* (2006.01)
*A61K 31/497* (2006.01)
*C07D 403/02* (2006.01)
*C07D 209/88* (2006.01)

(52) U.S. Cl. .................. 514/254.08; 514/290; 514/307; 514/411; 540/479; 544/372; 546/110; 548/441

(58) Field of Classification Search ............. 514/254.08, 514/290, 307, 411; 540/479; 544/372; 546/110; 548/441
See application file for complete search history.

(56) References Cited

U.S. PATENT DOCUMENTS 4,808,608 A    2/1989   Guindon et al.

FOREIGN PATENT DOCUMENTS

| EP | 1 505 061 | | 2/2005 |
|---|---|---|---|
| EP | 1 600 440 | | 11/2005 |
| GB | 2 388 540 | A | 11/2003 |
| GB | 2 407 318 | | 4/2005 |
| WO | WO 01/79169 | | 10/2001 |
| WO | WO 02/094830 | | 11/2002 |
| WO | WO-03/051837 | | 6/2003 |
| WO | WO-03/062200 | | 7/2003 |
| WO | WO 03/066046 | | 8/2003 |
| WO | WO 03/066047 | | 8/2003 |
| WO | WO 03/097042 | | 11/2003 |
| WO | WO 03/097598 | | 11/2003 |
| WO | WO 03/101961 | | 12/2003 |
| WO | WO 2003/101981 | | 12/2003 |
| WO | WO 2004/007451 | | 1/2004 |
| WO | WO 2004/039807 | | 5/2004 |
| WO | WO 2004/078719 | | 9/2004 |
| WO | WO 2004/103970 | | 12/2004 |
| WO | WO 2004/106302 | | 12/2004 |
| WO | WO 2004/111047 | | 12/2004 |
| WO | WO 2005/019171 | | 3/2005 |
| WO | WO 2005/040112 | | 5/2005 |
| WO | WO 2005/040114 | | 5/2005 |
| WO | WO 2005/044260 | | 5/2005 |
| WO | WO 2005/054232 | | 6/2005 |
| WO | WO 2005/056527 | | 6/2005 |
| WO | WO 2005/073234 | | 8/2005 |
| WO | WO 2005/094816 | | 10/2005 |
| WO | WO 2005/095397 | | 10/2005 |
| WO | WO 2006/021418 | | 3/2006 |
| WO | WO 2008/017989 | | 2/2008 |

OTHER PUBLICATIONS

Dorwald F. A. Side Reactions in Organic Synthesis, 2005, Wiley: VCH, Weinheim p. IX of Preface.*
Sugimoto, H. et al.; "An Orally Bioavailable Small Molecule Antagonist of CRTH2, Ramatroban (BAY u3405), Inhibits Prostaglandin $D_2$-Induced Eosinophil Migration in Vitro"; The Journal of Pharacology and Experimental Therapeutics, 2003, vol. 305, No. 1, pp. 347-352.
Berge, Stephen M., et al.; "Pharmaceutical Salts"; Journal of Pharmaceutical Sciences, Jan. 1977, vol. 66, No. 1, pp. 1-19.
Bundgaard, H.; "Design of Prodrugs"; 1985 Elsevier Amsterdam, pp. 7-9, 21-24.
Silverman R.B.; The Organic Chemistry of Drug Design and Drug Action; pp. 352-401, Academic Press, San Diego, CA (1992).
Higuchi, T. et al.; "Pro-drugs as Novel Drug Delivery Systems"; A.C.S. Symposium Series, American Chemical Society, 1975, vol. 14, pp. 154-183.
Sawyer, N. et al.; "Molecular pharmacology of the human prostaglandin $D_2$ receptor, CRTH2"; British Journal of Pharmacology (2002), vol. 137, pp. 1163-1172.
Larock Richard C.; "Comprehensive Organic Transformations"; Wiley-VCH Publishers, 1999.
Greene, Theodora W., et al.; "Protective Groups in Organic Synthesis"; Wiley-Interscience (1999).
Block, Michael H. et al.; "Discovery and Optimization of a Series of Carbazole Ureas as NPY5 Antagonists for the Treatment of Obesity"; Journal of Medicinal Chemistry, 2002, vol. 45, No. 16, pp. 3509-3523.
Wustrow, David et al.; Aminopyrimidines with High Affinity for Both Serotonin and Dopamine Receptors'; Journal of Medicinal Chemistry, 1998, vol. 41, No. 5, pp. 760-771.
Rubin, Martin et al.; "1-Methyl-3-ethyl-4-(*p*—hydroxyphenyl)-$\Delta^3$-cyclohexenylethylcarbinol, and "Open-Model" of Estradiol"; J. Amer. Chem. Soc. 1946, vol. 68, pp. 338-340.

(Continued)

*Primary Examiner* — Sabiha Qazi
(74) *Attorney, Agent, or Firm* — Hunton & Williams LLP

(57) ABSTRACT

The invention relates to novel tetrahydro-1H-carbazole derivatives and their use as active ingredients in the preparation of pharmaceutical compositions. The invention also concerns related aspects including processes for the preparation of the compounds, pharmaceutical compositions containing one or more of those compounds and methods of treatment comprising administration of said compounds to patients.

14 Claims, No Drawings

OTHER PUBLICATIONS

Chapman, N.B. et al.; "The Preparation of 4-Substituted 1-Methoxycarbonylbicyclo[2.2.2]octanes, Substituted 1-Phenylbicyclo[2.2.2]octanes, 4-Substituted 1-p—Nitrophenylbicyclo[2.2.2]octanes, and 1,4-Disubstituted Bicyclo[2.2.2]octanes"; The Journal of Organic Chemistry, vol. 35, No. 4, Apr. 1970, pp. 917-923.

Bruson, Herman A. et al.; "The Chemistry of Acrylonitrile. II. Reactions with Ketones"; J. Amer. Chem. Soc. 1942, vol. 64, pp. 2850-2858.

Kotake, Y. et al.; "Novel 6-5 Fused Ring Heterocycle Antifolates with Potent Antitumor Activity: Bridge Modifications and Heterocyclic Benzoyl Isosters of 2,4-Diamino-6,7-dihydro-5$H$—cyclopenta[$d$]pyrimidine Antifolate"; Chem. Pharm. Bull, May 1995, vol. 43, No. 5, pp. 829-841.

Arcari, M. et al; "Synthesis and Pharmacological Evaluation of 2,3-Dialkylindoles, "In Vitro" Inhibitors of Thrombin-Induced Platelet Aggregation"; Il Farmaco, vol. 47, No. 4, pp. 405-425, 1992.

Beller, M. et al.; "Base-Catalyzed Synthesis of $N$-(2-Arylethyl)anilines and Base-Promoted Domino Synthesis of 2,3-Dihydroindoles"; Angew. Chem. Int. Ed., 1998, vol. 37, No. 24, pp. 3389-3391.

Kwong, Fuk Yee et al; "Copper-Catalyzed Coupling of Alkylamines and Aryl Iodides: An Efficient System Even in an Air Atmosphere"; Organic Letters, 2002, vol. 4, No. 4, pp. 581-584.

Lewin, G. et al; "One-Pot Access to 2,3-Disbustituted 1,2,3,4-Tetrahydroquinolines by Reductive Amination of Aldehydes with Sodium Cyanoborohydride"; Heterocycles, vol. 48, No. 1, 1998, pp. 171-174.

Monro, A.M. et al.; "Some Analogs of Imipramine"; J. Med. Chem., 1963, vol. 6, pp. 255-261.

Warawa, Edward J. et al.; "Behavioral Approach to Nondyskinetic Dopamine Antagonists: Identification of Seroquel"; J. Med. Chem., 2001, vol. 44, pp. 372-389.

Werner, L.H. et al.; "Derivatives of Morphanthridine"; J. Med. Chem., 1965, vol. 8, pp. 74-80.

Margolis, Brandon J. et al.; "An Efficient Assembly of Heterobenzazepine Ring Systems Utilizing and Intramolecular Palladium-Catalyzed Cycloamination"; J. Org. Chem., 2003, vol. 68, pp. 644-647.

Bryant, William S. et al.; "A Study of the Complexation of Bis($m$-Phenylene) Crown Ethers and Secondary Ammonium Ions"; J. Org. Chem., 1998, vol. 63, pp. 7634-7639.

Albright, J. Donald et al.; "Potential Antiatherosclerotic Agents. 2. [1](Aralkylamino)-and (Alkylamino)benzoic Acid Analogues of Cetaben"; J. Med. Chem., 1983, vol. 26, pp. 1378-1393.

Ishizuka et al., Cardiovascular Drug Reviews, vol. 22, No. 2, pp. 71-90 (2004).

Robarge et al., Bioorganic & Medicinal Chemistry Letters, vol. 15, pp. 1749-1753 (2005).

Ulven et al., Journal of Medicinal Chemistry, vol. 48, No. 4, pp. 897-900 (2005).

* cited by examiner

2,3,4,9-TETRAHYDRO-1H-CARBAZOLE DERIVATIVES AS CRTH2 RECEPTOR ANTAGONISTS

FIELD OF THE INVENTION

The present invention relates to 2,3,4,9-tetrahydro-1H-carbazole compounds of the Formula I and their use as potent "chemoattractant receptor-homologous molecule expressed on Th2 cells" (hereinafter called CRTH2) antagonists in the treatment of prostaglandin mediated diseases, to pharmaceutical compositions containing these compounds and to processes for their preparation. In particular, a compound of the Formula I may be used in pharmaceutical compositions for the treatment of both chronic and acute allergic/immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophil-related diseases, such as basophilic leukemia and basophilic leukocytosis, in humans and other mammals.

BACKGROUND OF THE INVENTION

The complex response to allergen exposure results in a cascade of effects involving numerous mediators comprising different cell types like neutrophiles, monocytes, eosinophiles, mast cells and T helper (Th) cells as well as cytokines and chemokines. For example, Th2 cells regulate allergic responses by producing Th2 cytokines, such as interleukin (IL)-4, IL-5 and IL-13. Among the events triggered by such mediators are Th2 cell differentiation, immunoglobulin (Ig)E synthesis, mast cell growth and differentiation, upregulation of CD23 expression, differentiation, recruitment, migration and activation of effector cells, such as eosinophils and basophils as well as the priming for their prolonged survival. Allergic or immune responses due to sustained release of above-mentioned mediators may culminate, if untreated, in severe inflammatory diseases with end-organ damage, hyper-responsiveness, enhanced vascular permeability, edema, mucous hyper-secretion, airway hyperactivity, and bronchio-constriction.

Prostaglandin D2 (PGD2), histamine, cysteinyl leukotrienes (CysLTs) and thromboxane A2 (TxA2) are chemokines considered to act as proinflammatory key mediators in allergic responses. PGD2 is a major cyclooxygenase metabolite of arachidonic acid and is released in large amounts from activated mast cells during allergic attacks.

PGD2 is known to activate thromboxane A2 (TP) receptor, PGD2 (DP1) receptor and recently identified G-protein-coupled "chemoattractant receptor-homologous molecule expressed on Th2 cells" (CRTH2 or DP2) receptor. CRTH2 receptors are expressed on Th2 cells, eosinophiles and basophiles. PGD2 induces migration and activation of these cells via CRTH2 receptor activation.

A plethora of medications, such as anti-histamines, β2-agonists, leukotriene modifiers, non-steroidal anti-inflammatory agents, cyclooxygenase-2 inhibitors, immuno-suppressants, and monoclonal anti-IgE antibody have been used to treat symptoms of allergic conditions. Corticosteroids remain the most effective medication in the treatment of allergen-induced disorders, despite severe dose-limiting side effects that are due to non-specific inhibition of the transcription of several cytokines and chemokines. Such medications do not cure the disease and debilitating symptoms may relapse soon after treatment is stopped. Thus, there is still a need for new modalities to treat and/or to prevent allergic responses by suppressing specifically chemoattractant induced, e.g. PGD2 induced, tissue invasion of effector cells. Therefore, antagonists blocking CRTH2 receptor binding of PGD2 should be useful for the treatment of allergic conditions.

So far, few compounds having CRTH2 antagonistic activity have been reported in the patent literature. Bayer AG claims in GB Patent Specification No. 2388540 the use of Ramatroban ((3R)-3-(4-fluorobenzene-sulfonamido)-1,2,3,4-tetrahydrocarbazole-9-propionic acid) for the prophylaxis and treatment of allergic diseases, such as asthma, allergic rhinitis or allergic conjuvatitis. Oral bioavailability of Ramatroban and its ability to inhibit prostaglandin D2-induced eosinophil migration in vitro has been reported in *Journal of Pharmacology and Experimental Therapeutics*, 2003, 305 (1), 347-352.

DESCRIPTION OF THE INVENTION

In a first aspect, the present invention relates to novel 2,3,4,9-tetrahydro-1H-carbazole compounds of the Formula I:

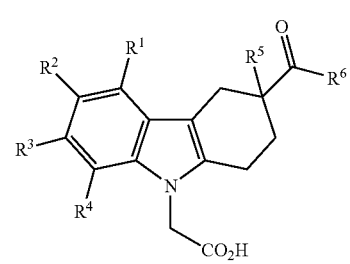

wherein
$R^1$, $R^2$, $R^3$ and $R^4$ independently represent hydrogen, alkyl (especially methyl or isopropyl), alkoxy (especially methoxy), halogen, nitro, cyano, trifluoromethyl, or formyl; preferably hydrogen, alkyl (especially methyl or isopropyl), alkoxy (especially methoxy), halogen, nitro, cyano, or trifluoromethyl; preferably $R^1$ represents hydrogen;
$R^5$ represents hydrogen, alkyl, or —$CF_3$; preferably hydrogen or alkyl, such as especially hydrogen, methyl, ethyl, or n-propyl;
$R^6$ represents alkoxy, aryl-alkoxy, or —$NR^7R^8$; especially phenyl-alkoxy or —$NR^7R^8$, most preferably —$NR^7R^8$;
$R^7$ and $R^8$ independently represent hydrogen, alkyl, cyano-alkyl, alkenyl, aryl, aryl-alkyl, phenylcarbonyl, cycloalkyl, pyridyl-alkyl (especially pyridyl-ethyl), thienyl-alkyl (especially thienyl-methyl), furanyl-alkyl, or imidazolyl-alkyl; or $R^7$ and $R^8$, together with the nitrogen atom to which they are attached, form a heterocyclic 5-, 6-, 7-, or 8-membered ring system with one to three heteroatoms which are selected from nitrogen, oxygen and sulfur (especially 1 or 2 nitrogen heteroatoms) and which ring system is optionally substituted with (i) one or two annellated benzene rings, which benzene rings are unsubstituted or substituted with one or two substituents independently selected from C1-C4 alkyl, C1-C4 alkoxy (especially methoxy), halogen, —$CF_3$, and —$OCF_3$; (ii) an unsubstituted phenyl ring; (iii) a mono- or di-substituted phenyl ring, wherein the substituents are independently selected from halogen, C1-C4 alkyl, C1-C4 alkoxy, —CF$_3$, and —OCF$_3$; or (iv) phenyl-alkyl wherein the alkyl moiety is substituted by phenyl, such as especially benzhydryl;

and optically pure enantiomers, mixtures of enantiomers such as racemates, optically pure diastereomers, mixtures of diastereomers, mixtures of enantiomers and diasteromers such as diastereomeric racemates, meso forms, and geometric isomers;

prodrugs of such compounds in which a prodrug forming group is present, as well as solvates and morphological forms, and pharmaceutically acceptable salts thereof.

The compounds of the Formula I are CRTH2 receptor antagonists and may be used for the prevention and/or treatment of chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, and basophil-related diseases, comprising basophilic leukemia and basophilic leukocytosis, in humans and other mammals.

In one embodiment, the present invention relates to a compound of Formula I, wherein $R^1$, $R^2$, $R^3$ and $R^4$ independently represent hydrogen, alkyl, alkoxy, halogen, nitro, cyano, trifluoromethyl, or formyl;

$R^5$ represents hydrogen, alkyl, or —CF$_3$;

$R^6$ represents alkoxy; aryl-alkoxy; mono-, di-, or tri-substituted aryl-alkoxy substituted independently in the aryl moiety with halogen, C1-C4 alkyl, C1-C4 alkoxy, —CF$_3$, —OCF$_3$; or —NR$^7$R$^8$;

$R^7$ and $R^8$ independently represent hydrogen; alkyl; cyanoalkyl; alkenyl; aryl; mono-, di-, or tri-substituted aryl substituted independently in the aryl moiety with halogen, C1-C4 alkyl, C1-C4 alkoxy, —CF$_3$, —OCF$_3$; aryl-alkyl; mono-, di-, or tri-substituted aryl-alkyl substituted independently in the aryl moiety with halogen, C1-C4 alkyl, C1-C4 alkoxy, —CF$_3$, —OCF$_3$; phenylcarbonyl; phenyl-C1-C4 alkyl optionally substituted with a methylendioxy group at the phenyl ring; cycloalkyl; pyridyl-alkyl; thienyl-alkyl; furanyl-alkyl; or imidazolyl-alkyl; or $R^7$ and $R^8$, together with the nitrogen atom to which they are attached, form a heterocyclic 5-, 6-, 7-, or 8-membered ring system with one to three heteroatoms which are selected from nitrogen, oxygen and sulfur and which ring system is optionally substituted with (i) one or two annellated benzene rings, which benzene rings are unsubstituted or substituted with one or two substituents selected from C1-C4 alkyl, C1-C4 alkoxy, halogen, —CF$_3$, —OCF$_3$; (ii) an unsubstituted phenyl ring; or (iii) a mono- or di-substituted phenyl ring substituted with halogen, C1-C4 alkyl, C1-C4 alkoxy, —CF$_3$, or —OCF$_3$.

In a preferred embodiment, $R^1$, $R^2$, $R^3$ and $R^4$ represent C$_1$-C$_4$ alkyl, C$_1$-C$_4$ alkoxy, halogen, nitro, cyano or trifluoromethyl. In a particularly preferred embodiment, $R^1$, $R^2$, $R^3$ and $R^4$ are selected from the group consisting of methyl, trifluoromethyl, methoxy, fluoro, chloro, bromo or iodo.

In another preferred embodiment, $R^7$ represents hydrogen, alkenyl, alkyl, aryl-alkyl, cycloalkyl, or heteroaryl-alkyl; and $R^8$ represents aryl; aryl-alkyl; or heteroaryl-alkyl.

In a further preferred embodiment, $R^7$ represents alkenyl, alkyl, aryl-C1-C4 alkyl, cycloalkyl, thienyl-C1-C4 alkyl, furanyl-C1-C4 alkyl, pyridyl-C1-C4 alkyl, or imidazolyl-C1-C4 alkyl; and $R^8$ represents hydrogen, aryl, aryl-C1-C4 alkyl, furanyl-C1-C4 alkyl, pyridyl-C1-C4 alkyl, or thienyl-C1-C4 alkyl.

In a particularly preferred embodiment, $R^7$ represents hydrogen, allyl, 2-cyano-ethyl, methyl, butyl, ethyl, isopropyl, benzyl, 1-phenyl-ethyl, 2-phenyl-ethyl, phenyl-propyl, cyclohexyl, or thiophen-3-ylmethyl; and $R^8$ represents phenyl, 2-benzyl-phenyl, 2-methoxy-phenyl, 2-methyl-phenyl, 2-trifluoromethyl-phenyl, 3,4-dichloro-phenyl, 3-benzoyl-phenyl, 3-chloro-phenyl, 2-fluoro-phenyl, 3-fluoro-phenyl, 4-chloro-phenyl, 4-fluoro-phenyl, 4-methoxy-biphenyl-3-yl, 4-trifluoromethoxy-phenyl, 5-chloro-2-methoxy-phenyl, naphthalen-1-yl, benzo[1,3]dioxol-5-ylmethyl, benzyl, diphenylmethyl, 1-phenyl-ethyl, 2-phenyl-ethyl, 2-pyridin-2-yl-ethyl, 4-phenyl-benzyl, 3,4-dichloro-benzyl, 2,4-dichloro-benzyl, difluoromethoxy-benzyl, 2-chloro-benzyl, 4-chloro-benzyl, 2-methylsulfanyl-benzyl, 2-fluoro-benzyl, 3-fluoro-benzyl, 4-fluoro-benzyl, 2-trifluoromethyl-benzyl, 3-trifluoromethyl-benzyl, 2,4-difluoro-benzyl, 2,5-difluoro-benzyl, 2,6-difluoro-benzyl, 3,5-difluoro-benzyl, 4-chloro-2-fluoro-benzyl, (2-fluoro-phenyl)-ethyl, (3-fluoro-phenyl)-ethyl, (4-fluoro-phenyl)-ethyl, (4-chloro-phenyl)-ethyl, (2,6-dichloro-phenyl)-ethyl, naphthalene-1-ylmethyl, 1,2,3,4-tetrahydro-naphthalen-1-yl, indan-2-yl, or 2,2-diphenyl-ethyl.

In a particular embodiment, $R^7$ represents hydrogen, allyl, 2-cyano-ethyl, butyl, ethyl, isopropyl, 3-phenyl-propyl, benzyl, phenylethyl, cyclohexyl, or thiophen-3-ylmethyl; and $R^8$ represents 2-benzyl-phenyl, 2-methoxy-phenyl, 2-methyl-phenyl, 2-trifluoromethyl-phenyl, 3,4-dichloro-phenyl, 3-benzoyl-phenyl, 3-chloro-phenyl, 3-fluoro-phenyl, 4-chloro-phenyl, 4-fluoro-phenyl, 4-methoxy-biphenyl-3-yl, 4-trifluoromethoxy-phenyl, 5-chloro-2-methoxy-phenyl, naphthalen-1-yl, (R)-1-phenyl-ethyl, (S)-1-phenyl-ethyl, benzo[1,3]dioxol-5-ylmethyl, benzyl, diphenylmethyl, phenylethyl, or 2-pyridin-2-yl-ethyl.

In a further embodiment, $R^7$ represents allyl, 2-cyano-ethyl, butyl, ethyl, isopropyl, 3-phenyl-propyl, benzyl, phenylethyl, cyclohexyl, or thiophen-3-ylmethyl; and $R^8$ represents 2-benzyl-phenyl, 2-methoxy-phenyl, 2-methyl-phenyl, 2-trifluoromethyl-phenyl, 3,4-dichloro-phenyl, 3-benzoyl-phenyl, 3-chloro-phenyl, 3-fluoro-phenyl, 4-chloro-phenyl, 4-fluoro-phenyl, 4-methoxy-biphenyl-3-yl, 4-trifluoromethoxy-phenyl, 5-chloro-2-methoxy-phenyl, naphthalen-1-yl, (R)-1-phenyl-ethyl, (S)-1-phenyl-ethyl, benzo[1,3]dioxol-5-ylmethyl, benzyl, diphenylmethyl, phenylethyl, or 2-pyridin-2-yl-ethyl; or $R^8$ represents hydrogen, aryl; aryl-C1-C4 alkyl, furanyl-C1-C4 alkyl, pyridyl-C1-C4 alkyl, or thienyl-C1-C4 alkyl.

In still another preferred embodiment, $R^7$ and $R^8$, together with the nitrogen atom to which they are attached, form a dihydro-dibenzo[b,f]azocine, dihydro-indole, dihydroisoquinoline, dihydroquinoline, or dibenzoazepine ring. Particularly preferred is 11,12-dihydro-6H-dibenzo[b,f]azocine-5-yl, 2,3-dihydro-indole-1-yl, 3,4-dihydro-1H-isoquinoline-2-yl, 3,4-dihydro-2H-quinoline-1-yl, 4-(4-fluoro-phenyl)-piperazine-1-yl, 6,11-dihydro-dibenzo[b,e]azepine-5-yl, 6,7-dimethoxy-3,4-dihydro-1H-isoquinoline-2-yl, 7-trifluoromethyl-3,4-dihydro-2H-quinoline-1-yl, and dibenzo[b,f]azepine-5-yl. In a further particularly preferred embodiment $R^7$ and $R^8$, together with the nitrogen atom to which they are attached, form 11,12-dihydro-6H-dibenzo[b,f]azocine-5-yl, 2,3-dihydro-indole-1-yl, 3,4-dihydro-1H-isoquinoline-2-yl, 3,4-dihydro-2H-quinoline-1-yl, 4-(4-fluoro-phenyl)-piperazine-1-yl, 6,11-dihydro-dibenzo[b,e]azepine-5-yl, 6,7-dimethoxy-3,4-dihydro-1H-isoquinoline-2-yl, 7-trifluoromethyl-3,4-dihydro-2H-quinoline-1-yl, dibenzo[b,f]azepine- 5-yl, 1H,3H-benzo[d,e]isoquinoline-2-yl, 4-benzhydryl-piperazine-1-yl, or azocane-1-yl.

In a further preferred embodiment, $R^6$ represents $C_1$-$C_4$ alkoxy or aryl-C1-C4 alkoxy, in particular (R)-1-phenyl-ethyloxy or benzyloxy.

The present invention also relates to compounds of Formula I wherein the meanings of one or more of the substituents and symbols as defined for Formula I, or an embodiment of Formula I, are replaced by their preferred meanings as defined herein, such as those defined hereinabove.

In a very preferred embodiment, the present invention relates to a compound of Formula I, wherein
$R^1$, $R^2$, $R^3$ and $R^4$ independently represent hydrogen, alkyl, alkoxy, halogen, nitro, cyano, or trifluoromethyl; preferably $R^1$ represents hydrogen;
$R^5$ represents hydrogen or alkyl;
$R^6$ represents phenyl-alkoxy or —$NR^7R^8$;
$R^7$ and $R^8$ independently represent hydrogen; alkyl; cyano-alkyl; alkenyl; phenyl optionally mono-substituted by halogen, alkyl, alkoxy, —$CF_3$, —$OCF_3$, phenyl-alkyl or phenyl-carbonyl; phenyl, di-substituted with a substituent independently selected from halogen, alkoxy and phenyl; phenyl-alkyl optionally substituted in the alkyl moiety by phenyl or optionally substituted in the phenyl ring by methylenedioxy; phenyl-alkyl which is di-substituted by halogen or mono-substituted by halogen, —$CF_3$, —$OCHF_2$, alkyl or alkylsulfanyl; naphthyl; naphthyl-alkyl; cycloalkyl, especially cyclopentyl or cyclohexyl, which is optionally substituted with an annellated benzene ring; pyridyl-alkyl; or thienyl-alkyl; or
$R^7$ and $R^8$, together with the nitrogen atom to which they are attached, form a heterocyclic 5-, 6-, 7-, or 8-membered ring system with one or two heteroatoms selected from nitrogen and which ring system is optionally substituted with (i) one or two annellated benzene rings, which benzene rings are unsubstituted or substituted with one or two substituents independently selected from alkoxy and —$CF_3$; (ii) a mono-substituted phenyl ring substituted with halogen; or (iii) phenyl-alkyl, wherein the alkyl moiety is substituted with phenyl.

Most preferred novel compounds of the present invention include:
[3-methyl-3-(methyl-phenyl-carbamoyl)-1,2,3,4-tetrahydro-carbazol-9-yl]-acetic acid;
{3-[(3-chloro-phenyl)-methyl-carbamoyl]-3-methyl-1,2,3,4-tetrahydro-carbazol-9-yl}-acetic acid;
[3-(2,3-dihydro-indole-1-carbonyl)-1,2,3,4-tetrahydro-carbazol-9-yl]-acetic acid;
[3-methyl-3-(phenyl-thiophen-3-ylmethyl-carbamoyl)-1,2,3,4-tetrahydro-carbazol-9-yl]-acetic acid;
[3-(benzyl-phenyl-carbamoyl)-3-methyl-1,2,3,4-tetrahydro-carbazol-9-yl]-acetic acid;
{3-[(4-fluoro-phenyl)-methyl-carbamoyl]-3-methyl-1,2,3,4-tetrahydro-carbazol-9-yl}-acetic acid;
[3-(6,11-dihydro-dibenzo[b,e]azepine-5-carbonyl)-1,2,3,4-tetrahydro-carbazol-9-yl]-acetic acid;
[3-(benzyl-phenyl-carbamoyl)-1,2,3,4-tetrahydro-carbazol-9-yl]-acetic acid;
{3-[phenyl-(3-phenyl-propyl)-carbamoyl]-1,2,3,4-tetrahydro-carbazol-9-yl}-acetic acid;
[3-(2,3-dihydro-indole-1-carbonyl)-3-methyl-1,2,3,4-tetrahydro-carbazol-9-yl]-acetic acid;
{3-[(3,4-dichloro-phenyl)-methyl-carbamoyl]-3-methyl-1,2,3,4-tetrahydro-carbazol-9-yl}-acetic acid;
[3-(allyl-phenyl-carbamoyl)-3-methyl-1,2,3,4-tetrahydro-carbazol-9-yl]-acetic acid;
{3-[benzyl-((S)-1-phenyl-ethyl)-carbamoyl]-1,2,3,4-tetrahydro-carbazol-9-yl}-acetic acid; and
{3-[methyl-(2-trifluoromethyl-phenyl)-carbamoyl]-1,2,3,4-tetrahydro-carbazol-9-yl}-acetic acid.

Particularly preferred novel compounds of the present invention include:
[3-(methyl-phenyl-carbamoyl)-6-trifluoromethyl-1,2,3,4-tetrahydro-carbazol-9-yl]-acetic acid;
[3-methyl-3-(methyl-o-tolyl-carbamoyl)-1,2,3,4-tetrahydro-carbazol-9-yl]-acetic acid;
[3-(2-benzyl-phenylcarbamoyl)-1,2,3,4-tetrahydro-carbazol-9-yl]-acetic acid;
[3-(dibenzo[b,f]azepine-5-carbonyl)-1,2,3,4-tetrahydro-carbazol-9-yl]-acetic acid;
[3-(ethyl-naphthalen-1-yl-carbamoyl)-1,2,3,4-tetrahydro-carbazol-9-yl]-acetic acid;
[3-(benzhydryl-methyl-carbamoyl)-1,2,3,4-tetrahydro-carbazol-9-yl]-acetic acid;
{3-methyl-3-[phenyl-(3-phenyl-propyl)-carbamoyl]-1,2,3,4-tetrahydro-carbazol-9-yl}-acetic acid;
[3-(ethyl-phenyl-carbamoyl)-1,2,3,4-tetrahydro-carbazol-9-yl]-acetic acid;
[3-(phenyl-thiophen-3-ylmethyl-carbamoyl)-1,2,3,4-tetrahydro-carbazol-9-yl]-acetic acid;
[3-(benzyl-isopropyl-carbamoyl)-1,2,3,4-tetrahydro-carbazol-9-yl]-acetic acid;
{3-[4-(4-fluoro-phenyl)-piperazine-1-carbonyl]-1,2,3,4-tetrahydro-carbazol-9-yl}-acetic acid;
[3-(benzyl-phenethyl-carbamoyl)-3-methyl-1,2,3,4-tetrahydro-carbazol-9-yl]-acetic acid;
[3-(3,4-dihydro-2H-quinoline-1-carbonyl)-1,2,3,4-tetrahydro-carbazol-9-yl]-acetic acid;
[3-(cyclohexyl-phenyl-carbamoyl)-1,2,3,4-tetrahydro-carbazol-9-yl]-acetic acid;
{3-[(3-chloro-phenyl)-methyl-carbamoyl]-1,2,3,4-tetrahydro-carbazol-9-yl}-acetic acid;
[3-methyl-3-(phenethyl-phenyl-carbamoyl)-1,2,3,4-tetrahydro-carbazol-9-yl]-acetic acid;
[3-(2-methoxy-phenylcarbamoyl)-1,2,3,4-tetrahydro-carbazol-9-yl]-acetic acid;
[3-(allyl-phenyl-carbamoyl)-1,2,3,4-tetrahydro-carbazol-9-yl]-acetic acid;
[3-(benzyl-phenethyl-carbamoyl)-1,2,3,4-tetrahydro-carbazol-9-yl]-acetic acid;
[3-(phenethyl-phenyl-carbamoyl)-1,2,3,4-tetrahydro-carbazol-9-yl]-acetic acid;
[3-(methyl-o-tolyl-carbamoyl)-1,2,3,4-tetrahydro-carbazol-9-yl]-acetic acid;
{3-[benzyl-((R)-1-phenyl-ethyl)-carbamoyl]-1,2,3,4-tetrahydro-carbazol-9-yl}-acetic acid;
[3-(methyl-phenyl-carbamoyl)-6-nitro-1,2,3,4-tetrahydro-carbazol-9-yl]-acetic acid;
[3-(7-trifluoromethyl-3,4-dihydro-2H-quinoline-1-carbonyl)-1,2,3,4-tetrahydro-carbazol-9-yl]-acetic acid;
[3-(3,4-dihydro-2H-quinoline-1-carbonyl)-3-methyl-1,2,3,4-tetrahydro-carbazol-9-yl]-acetic acid;
{3-[(4-fluoro-phenyl)-methyl-carbamoyl]-1,2,3,4-tetrahydro-carbazol-9-yl}-acetic acid;
[3-(4-methoxy-biphenyl-3-ylcarbamoyl)-1,2,3,4-tetrahydro-carbazol-9-yl]-acetic acid;
[6-fluoro-3-(methyl-phenyl-carbamoyl)-1,2,3,4-tetrahydro-carbazol-9-yl]-acetic acid;
[7-chloro-3-(methyl-phenyl-carbamoyl)-1,2,3,4-tetrahydro-carbazol-9-yl]-acetic acid;
[6-chloro-3-(methyl-phenyl-carbamoyl)-1,2,3,4-tetrahydro-carbazol-9-yl]-acetic acid;
{3-[methyl-(2-pyridin-2-yl-ethyl)-carbamoyl]-1,2,3,4-tetrahydro-carbazol-9-yl}-acetic acid;

{3-[(4-chloro-phenyl)-methyl-carbamoyl]-1,2,3,4-tetrahydro-carbazol-9-yl}-acetic acid;
{(R)-3-[(4-chloro-phenyl)-methyl-carbamoyl]-1,2,3,4-tetrahydro-carbazol-9-yl}-acetic acid;
[3-(isopropyl-phenyl-carbamoyl)-1,2,3,4-tetrahydro-carbazol-9-yl]-acetic acid;
{3-[(3,4-dichloro-phenyl)-methyl-carbamoyl]-1,2,3,4-tetrahydro-carbazol-9-yl}-acetic acid;
[3-(benzhydryl-carbamoyl)-1,2,3,4-tetrahydro-carbazol-9-yl]-acetic acid;
[6-cyano-3-(methyl-phenyl-carbamoyl)-1,2,3,4-tetrahydro-carbazol-9-yl]-acetic acid;
{3-[benzyl-((R)-1-phenyl-ethyl)-carbamoyl]-3-methyl-1,2,3,4-tetrahydro-carbazol-9-yl}-acetic acid;
[3-(2-benzyl-phenylcarbamoyl)-3-methyl-1,2,3,4-tetrahydro-carbazol-9-yl]-acetic acid;
[6-isopropyl-3-(methyl-phenyl-carbamoyl)-1,2,3,4-tetrahydro-carbazol-9-yl]-acetic acid;
[6-methyl-3-(methyl-phenyl-carbamoyl)-1,2,3,4-tetrahydro-carbazol-9-yl]-acetic acid;
[3-(11,12-dihydro-6H-dibenzo[b,f]azocine-5-carbonyl)-1,2,3,4-tetrahydro-carbazol-9-yl]-acetic acid;
[3-(methyl-phenethyl-carbamoyl)-1,2,3,4-tetrahydro-carbazol-9-yl]-acetic acid;
[6-bromo-3-(methyl-phenyl-carbamoyl)-1,2,3,4-tetrahydro-carbazol-9-yl]-acetic acid;
[3-(3-benzoyl-phenylcarbamoyl)-1,2,3,4-tetrahydro-carbazol-9-yl]-acetic acid;
(3-dibenzylcarbamoyl-1,2,3,4-tetrahydro-carbazol-9-yl)-acetic acid;
[3-(ethyl-naphthalen-1-yl-carbamoyl)-3-methyl-1,2,3,4-tetrahydro-carbazol-9-yl]-acetic acid;
{3-[(3-fluoro-phenyl)-methyl-carbamoyl]-1,2,3,4-tetrahydro-carbazol-9-yl}-acetic acid;
{3-[benzyl-(2-cyano-ethyl)-carbamoyl]-1,2,3,4-tetrahydro-carbazol-9-yl}-acetic acid;
(3-phenylcarbamoyl-1,2,3,4-tetrahydro-carbazol-9-yl)-acetic acid;
[3-(isopropyl-phenyl-carbamoyl)-3-methyl-1,2,3,4-tetrahydro-carbazol-9-yl]-acetic acid;
(3-diphenethylcarbamoyl-1,2,3,4-tetrahydro-carbazol-9-yl)-acetic acid;
[3-(benzhydryl-methyl-carbamoyl)-3-methyl-1,2,3,4-tetrahydro-carbazol-9-yl]-acetic acid;
[3-(5-chloro-2-methoxy-phenylcarbamoyl)-1,2,3,4-tetrahydro-carbazol-9-yl]-acetic acid;
[3-(butyl-phenyl-carbamoyl)-1,2,3,4-tetrahydro-carbazol-9-yl]-acetic acid;
{3-[ethyl-(4-trifluoromethoxy-phenyl)-carbamoyl]-1,2,3,4-tetrahydro-carbazol-9-yl}-acetic acid;
[3-(methyl-phenyl-carbamoyl)-1,2,3,4-tetrahydro-carbazol-9-yl]-acetic acid; and
[6-iodo-3-(methyl-phenyl-carbamoyl)-1,2,3,4-tetrahydro-carbazol-9-yl]-acetic acid.

Preferred novel compounds of the present invention include:
[6-methoxy-3-(methyl-phenyl-carbamoyl)-1,2,3,4-tetrahydro-carbazol-9-yl]-acetic acid;
9-carboxymethyl-2,3,4,9-tetrahydro-1H-carbazole-3-carboxylic acid (R)-1-phenyl-ethyl ester;
{(S)-3-[(4-chloro-phenyl)-methyl-carbamoyl]-1,2,3,4-tetrahydro-carbazol-9-yl}-acetic acid;
[3-(6,11-dihydro-dibenzo[b,e]azepine-5-carbonyl)-3-methyl-1,2,3,4-tetrahydro-carbazol-9-yl]-acetic acid;
[8-chloro-3-(methyl-phenyl-carbamoyl)-1,2,3,4-tetrahydro-carbazol-9-yl]-acetic acid;
9-carboxymethyl-2,3,4,9-tetrahydro-1H-carbazole-3-carboxylic acid benzyl ester;
[3-(3,4-dihydro-1H-isoquinoline-2-carbonyl)-1,2,3,4-tetrahydro-carbazol-9-yl]-acetic acid;
[3-(6,7-dimethoxy-3,4-dihydro-1H-isoquinoline-2-carbonyl)-1,2,3,4-tetrahydro-carbazol-9-yl]-acetic acid;
{3-[(benzo[1,3]dioxol-5-ylmethyl)-carbamoyl]-1,2,3,4-tetrahydro-carbazol-9-yl}-acetic acid; and
[3-(cyclohexyl-phenyl-carbamoyl)-3-methyl-1,2,3,4-tetrahydro-carbazol-9-yl]-acetic acid.

Most preferred novel compounds of the present invention further include:
{3-[benzyl-((R)-1-phenyl-ethyl)-carbamoyl]-6-fluoro-1,2,3,4-tetrahydro-carbazol-9-yl}-acetic acid;
[3-(benzhydryl-methyl-carbamoyl)-6-fluoro-1,2,3,4-tetrahydro-carbazol-9-yl]-acetic acid;
{3-[benzyl-((S)-1-phenyl-ethyl)-carbamoyl]-6-fluoro-1,2,3,4-tetrahydro-carbazol-9-yl}-acetic acid;
[3-(benzyl-phenethyl-carbamoyl)-6-fluoro-1,2,3,4-tetrahydro-carbazol-9-yl]-acetic acid;
[3-(2,3-dihydro-indole-1-carbonyl)-6-fluoro-1,2,3,4-tetrahydro-carbazol-9-yl]-acetic acid;
[3-(benzyl-isopropyl-carbamoyl)-6-fluoro-1,2,3,4-tetrahydro-carbazol-9-yl]-acetic acid;
[3-(azocane-1-carbonyl)-6-fluoro-1,2,3,4-tetrahydro-carbazol-9-yl]-acetic acid;
(3-phenylcarbamoyl-3-propyl-1,2,3,4-tetrahydro-carbazol-9-yl)-acetic acid;
[3-(methyl-phenyl-carbamoyl)-3-propyl-1,2,3,4-tetrahydro-carbazol-9-yl]-acetic acid;
[6-fluoro-3-(methyl-phenyl-carbamoyl)-1,2,3,4-tetrahydro-carbazol-9-yl]-acetic acid; and
{6-fluoro-3-[4-(4-fluoro-phenyl)-piperazine-1-carbonyl]-1,2,3,4-tetrahydro-carbazol-9-yl}-acetic acid.

Particularly preferred novel compounds of the present invention include:
[3-(4-fluoro-phenylcarbamoyl)-3-propyl-1,2,3,4-tetrahydro-carbazol-9-yl]-acetic acid;
{6-fluoro-3-[4-(4-fluoro-phenyl)-piperazine-1-carbonyl]-1,2,3,4-tetrahydro-carbazol-9-yl}-acetic acid;
[3-(benzhydryl-methyl-carbamoyl)-6-fluoro-1,2,3,4-tetrahydro-carbazol-9-yl]-acetic acid;
(3-{benzyl-[2-(2,6-dichloro-phenyl)-ethyl]-carbamoyl}-1,2,3,4-tetrahydro-carbazol-9-yl)-acetic acid;
{3-[benzyl-((S)-1-phenyl-ethyl)-carbamoyl]-6-fluoro-1,2,3,4-tetrahydro-carbazol-9-yl}-acetic acid;
[3-(3-fluoro-phenylcarbamoyl)-3-methyl-1,2,3,4-tetrahydro-carbazol-9-yl]-acetic acid;
[3-(3,5-difluoro-benzylcarbamoyl)-3-methyl-1,2,3,4-tetrahydro-carbazol-9-yl]-acetic acid;
[3-(3-fluoro-phenylcarbamoyl)-3-propyl-1,2,3,4-tetrahydro-carbazol-9-yl]-acetic acid;
[3-(3-fluoro-phenylcarbamoyl)-1,2,3,4-tetrahydro-carbazol-9-yl]-acetic acid;
[3-(2,3-dihydro-indole-1-carbonyl)-3-ethyl-1,2,3,4-tetrahydro-carbazol-9-yl]-acetic acid;
[3-ethyl-3-(3-fluoro-phenylcarbamoyl)-1,2,3,4-tetrahydro-carbazol-9-yl]-acetic acid;
[3-ethyl-3-(4-fluoro-phenylcarbamoyl)-1,2,3,4-tetrahydro-carbazol-9-yl]-acetic acid;
[3-(2-chloro-benzylcarbamoyl)-3-methyl-1,2,3,4-tetrahydro-carbazol-9-yl]-acetic acid;
[3-(benzyl-phenethyl-carbamoyl)-6-fluoro-1,2,3,4-tetrahydro-carbazol-9-yl]-acetic acid;
[3-methyl-3-(2-methylsulfanyl-benzylcarbamoyl)-1,2,3,4-tetrahydro-carbazol-9-yl]-acetic acid;

(3-ethyl-3-phenylcarbamoyl-1,2,3,4-tetrahydro-carbazol-9-yl)-acetic acid;
{3-[benzyl-((R)-1-phenyl-ethyl)-carbamoyl]-6-fluoro-1,2,3,4-tetrahydro-carbazol-9-yl}-acetic acid;
[3-ethyl-3-(methyl-phenyl-carbamoyl)-1,2,3,4-tetrahydro-carbazol-9-yl]-acetic acid;
[3-(2-fluoro-phenylcarbamoyl)-3-propyl-1,2,3,4-tetrahydro-carbazol-9-yl]-acetic acid;
[3-(2-fluoro-phenylcarbamoyl)-3-methyl-1,2,3,4-tetrahydro-carbazol-9-yl]-acetic acid;
{3-methyl-3-[(naphthalen-1-ylmethyl)-carbamoyl]-1,2,3,4-tetrahydro-carbazol-9-yl}-acetic acid;
{3-[benzyl-(2-cyano-ethyl)-carbamoyl]-3-methyl-1,2,3,4-tetrahydro-carbazol-9-yl}-acetic acid;
[3-(benzyl-butyl-carbamoyl)-3-methyl-1,2,3,4-tetrahydro-carbazol-9-yl]-acetic acid;
[3-(4-fluoro-phenylcarbamoyl)-3-methyl-1,2,3,4-tetrahydro-carbazol-9-yl]-acetic acid;
[3-(4-fluoro-phenylcarbamoyl)-1,2,3,4-tetrahydro-carbazol-9-yl]-acetic acid;
[3-(2,4-dichloro-benzylcarbamoyl)-3-methyl-1,2,3,4-tetrahydro-carbazol-9-yl]-acetic acid;
{3-[benzyl-(4-fluoro-benzyl)-carbamoyl]-1,2,3,4-tetrahydro-carbazol-9-yl}-acetic acid;
[3-(benzyl-isopropyl-carbamoyl)-6-fluoro-1,2,3,4-tetrahydro-carbazol-9-yl]-acetic acid;
[3-(2-difluoromethoxy-benzylcarbamoyl)-3-methyl-1,2,3,4-tetrahydro-carbazol-9-yl]-acetic acid;
[3-(2-fluoro-phenylcarbamoyl)-1,2,3,4-tetrahydro-carbazol-9-yl]-acetic acid;
[3-(benzyl-ethyl-carbamoyl)-3-methyl-1,2,3,4-tetrahydro-carbazol-9-yl]-acetic acid;
(3-methyl-3-phenylcarbamoyl-1,2,3,4-tetrahydro-carbazol-9-yl)-acetic acid;
[3-ethyl-3-(2-fluoro-phenylcarbamoyl)-1,2,3,4-tetrahydro-carbazol-9-yl]-acetic acid;
[3-(4-chloro-benzylcarbamoyl)-3-methyl-1,2,3,4-tetrahydro-carbazol-9-yl]-acetic acid; and
(3-{benzyl-[2-(4-fluoro-phenyl)-ethyl]-carbamoyl}-1,2,3,4-tetrahydro-carbazol-9-yl)-acetic acid.

Preferred novel compounds of the present invention include:
[3-methyl-3-(4-pentyl-benzylcarbamoyl)-1,2,3,4-tetrahydro-carbazol-9-yl]-acetic acid;
{3-[benzyl-(4-chloro-2-fluoro-benzyl)-carbamoyl]-1,2,3,4-tetrahydro-carbazol-9-yl}-acetic acid;
[3-(azocane-1-carbonyl)-6-fluoro-1,2,3,4-tetrahydro-carbazol-9-yl]-acetic acid;
[3-(2-fluoro-benzylcarbamoyl)-3-methyl-1,2,3,4-tetrahydro-carbazol-9-yl]-acetic acid;
[3-(3,4-dichloro-benzylcarbamoyl)-3-methyl-1,2,3,4-tetrahydro-carbazol-9-yl]-acetic acid;
(3-{benzyl-[2-(4-chloro-phenyl)-ethyl]-carbamoyl}-1,2,3,4-tetrahydro-carbazol-9-yl)-acetic acid;
[3-(2,4-difluoro-benzylcarbamoyl)-3-methyl-1,2,3,4-tetrahydro-carbazol-9-yl]-acetic acid;
[3-(benzhydryl-carbamoyl)-3-propyl-1,2,3,4-tetrahydro-carbazol-9-yl]-acetic acid;
{8-chloro-3-[4-(4-fluoro-phenyl)-piperazine-1-carbonyl]-1,2,3,4-tetrahydro-carbazol-9-yl}-acetic acid;
[8-chloro-3-(2,3-dihydro-indole-1-carbonyl)-1,2,3,4-tetrahydro-carbazol-9-yl]-acetic acid;
[3-(2,6-difluoro-benzylcarbamoyl)-3-methyl-1,2,3,4-tetrahydro-carbazol-9-yl]-acetic acid;
{3-[benzyl-(3-fluoro-benzyl)-carbamoyl]-1,2,3,4-tetrahydro-carbazol-9-yl}-acetic acid;
[3-(benzhydryl-methyl-carbamoyl)-8-chloro-1,2,3,4-tetrahydro-carbazol-9-yl]-acetic acid;
[3-(benzhydryl-carbamoyl)-3-methyl-1,2,3,4-tetrahydro-carbazol-9-yl]-acetic acid;
{3-[benzyl-(3-trifluoromethyl-benzyl)-carbamoyl]-1,2,3,4-tetrahydro-carbazol-9-yl}-acetic acid;
[3-(benzhydryl-carbamoyl)-3-ethyl-1,2,3,4-tetrahydro-carbazol-9-yl]-acetic acid;
[3-(4-fluoro-benzylcarbamoyl)-3-methyl-1,2,3,4-tetrahydro-carbazol-9-yl]-acetic acid;
(3-{benzyl-[2-(3-fluoro-phenyl)-ethyl]-carbamoyl}-1,2,3,4-tetrahydro-carbazol-9-yl)-acetic acid;
[3-(benzyl-isopropyl-carbamoyl)-3-methyl-1,2,3,4-tetrahydro-carbazol-9-yl]-acetic acid;
{3-[benzyl-(3,5-difluoro-benzyl)-carbamoyl]-1,2,3,4-tetrahydro-carbazol-9-yl}-acetic acid;
(3-{benzyl-[2-(2-fluoro-phenyl)-ethyl]-carbamoyl}-1,2,3,4-tetrahydro-carbazol-9-yl)-acetic acid;
{3-[benzyl-(2-trifluoromethyl-benzyl)-carbamoyl]-1,2,3,4-tetrahydro-carbazol-9-yl}-acetic acid;
{3-[benzyl-(4-fluoro-benzyl)-carbamoyl]-3-methyl-1,2,3,4-tetrahydro-carbazol-9-yl}-acetic acid; and
[3-(1H,3H-benzo[de]isoquinoline-2-carbonyl)-3-methyl-1,2,3,4-tetrahydro-carbazol-9-yl]-acetic acid.

Other preferred novel compounds of the present invention include:
{3-[benzyl-(2,5-difluoro-benzyl)-carbamoyl]-1,2,3,4-tetrahydro-carbazol-9-yl}-acetic acid;
{3-[benzyl-(3-fluoro-benzyl)-carbamoyl]-3-methyl-1,2,3,4-tetrahydro-carbazol-9-yl}-acetic acid;
{3-methyl-3-[(R)-(1,2,3,4-tetrahydro-naphthalen-1-yl)carbamoyl]-1,2,3,4-tetrahydro-carbazol-9-yl}-acetic acid;
{3-[benzyl-(3,5-difluoro-benzyl)-carbamoyl]-3-methyl-1,2,3,4-tetrahydro-carbazol-9-yl}-acetic acid;
[3-(benzyl-methyl-carbamoyl)-3-methyl-1,2,3,4-tetrahydro-carbazol-9-yl]-acetic acid;
(3-{benzyl-[2-(4-chloro-phenyl)-ethyl]-carbamoyl}-3-methyl-1,2,3,4-tetrahydro-carbazol-9-yl)-acetic acid;
(3-{benzyl-[2-(4-fluoro-phenyl)-ethyl]-carbamoyl}-3-methyl-1,2,3,4-tetrahydro-carbazol-9-yl)-acetic acid;
[8-chloro-3-(2,2-diphenyl-ethylcarbamoyl)-1,2,3,4-tetrahydro-carbazol-9-yl]-acetic acid;
{3-[benzyl-(3-trifluoromethyl-benzyl)-carbamoyl]-3-methyl-1,2,3,4-tetrahydro-carbazol-9-yl}-acetic acid;
[3-(4-benzhydryl-piperazine-1-carbonyl)-8-chloro-1,2,3,4-tetrahydro-carbazol-9-yl]-acetic acid;
{3-[benzyl-(4-chloro-2-fluoro-benzyl)-carbamoyl]-3-methyl-1,2,3,4-tetrahydro-carbazol-9-yl}-acetic acid;
[3-(benzhydryl-carbamoyl)-8-chloro-1,2,3,4-tetrahydro-carbazol-9-yl]-acetic acid;
[3-(2,3-dihydro-indole-1-carbonyl)-3-propyl-1,2,3,4-tetrahydro-carbazol-9-yl]-acetic acid;
(3-{benzyl-[2-(3-fluoro-phenyl)-ethyl]-carbamoyl}-3-methyl-1,2,3,4-tetrahydro-carbazol-9-yl)-acetic acid;
(3-{benzyl-[2-(2,6-dichloro-phenyl)-ethyl]-carbamoyl}-3-methyl-1,2,3,4-tetrahydro-carbazol-9-yl)-acetic acid;
{3-[benzyl-(2-trifluoromethyl-benzyl)-carbamoyl]-3-methyl-1,2,3,4-tetrahydro-carbazol-9-yl}-acetic acid;
{3-[benzyl-(2,5-difluoro-benzyl)-carbamoyl]-3-methyl-1,2,3,4-tetrahydro-carbazol-9-yl}-acetic acid;
[8-chloro-3-(indan-2-yl-carbamoyl)-1,2,3,4-tetrahydro-carbazol-9-yl]-acetic acid;
(3-{benzyl-[2-(2-fluoro-phenyl)-ethyl]-carbamoyl}-3-methyl-1,2,3,4-tetrahydro-carbazol-9-yl)-acetic acid;
[6-fluoro-3-((R)-1-phenyl-ethylcarbamoyl)-1,2,3,4-tetrahydro-carbazol-9-yl]-acetic acid;

[6-fluoro-3-((R)-1-phenyl-ethylcarbamoyl)-1,2,3,4-tetrahydro-carbazol-9-yl]-acetic acid;
[3-(benzyl-cyanomethyl-carbamoyl)-3-methyl-1,2,3,4-tetrahydro-carbazol-9-yl]-acetic acid;
[3-(2,3-dichloro-benzylcarbamoyl)-3-methyl-1,2,3,4-tetrahydro-carbazol-9-yl]-acetic acid; and
[7-methyl-3-(methyl-phenyl-carbamoyl)-1,2,3,4-tetrahydro-carbazol-9-yl]-acetic acid.

Unless explicitly stated otherwise, the general terms and names used hereinbefore and hereinafter preferably have within the context of this disclosure the following meanings:

The term "alkyl" as used herein, alone or in any combination, refers to a saturated aliphatic group including a straight or branched hydrocarbon chain containing 1-7, preferably 1-4 carbon atoms, i.e. C1-C4 alkyl. The alkyl group can optionally be substituted with one or more substituents, each independently selected from alkenyl, alkoxy, alkoxycarbonyl, alkylcarbonyl, alkylcarbonyloxy, alkylendioxy, alkylsulfinyl, alkylsulfonyl, alkylthio, alkynyl, amino, aminocarbonyl, aryl, arylalkenyl, arylalkyloxy, aryloxy, aryloxycarbonyl, arylsulfinyl, arylsulfonyl, arylthio, carboxy, cyano, formyl, halogen, haloalkoxy, heterocyclyl, hydroxy, mercapto, and nitro, appended to any carbon atom of the alkyl moiety. If not explicitly indicated otherwise, the term "alkyl" preferably relates to an unsubstituted alkyl group. Representative examples of alkyl include, but are not limited to, methyl, ethyl, n-propyl, iso-propyl, n-butyl, tert-butyl, iso-butyl (or 2-methylpropyl), cyclopropylmethyl, n-pentyl, iso-pentyl, iso-amyl, n-amyl, n-hexyl, n-heptyl, and n-octyl.

The term "alkenyl" as used herein, alone or in any combination, refers to a straight or branched hydrocarbon chain containing 2-7, preferably 2-4 carbon atoms with at least one carbon-carbon double bond ($R_aR_bC=CR_cR_d$). $R_a$-$R_d$ refer to substituents, each individually and independently selected from hydrogen, alkyl, alkoxy, and alkoxyalkyl, preferably hydrogen and alkyl. Representative examples of alkenyl include, but are not limited to, ethenyl, 2-propenyl, 2-methyl-2-propenyl, 3-butenyl, 4-pentenyl, and 5-hexenyl, especially 2-propenyl.

The term "alkylendioxy" as used herein, alone or in any combination, refers to an —$O(CH_2)_nO$— group, wherein n is preferably 1 or 2, and wherein the oxygen atoms are appended to two adjacent carbon atoms of the parent molecular moiety, preferably the two adjacent carbon atoms of a phenyl ring. Representative examples of alkylendioxy include, but are not limited to, methylendioxy and ethylendioxy.

The term "alkynyl" as used herein, alone or in any combination, refers to a straight or branched hydrocarbon chain containing 2-7 carbon atoms with at least one carbon-carbon triple bond ($R_a$—C≡C—$R_b$), $R_a$ and $R_b$ referring to substituents, each individually and independently selected from hydrogen, alkyl, alkenyl, alkoxy, and alkoxyalkyl, preferably hydrogen and alkyl. Representative examples of alkynyl include, but are not limited to, acetylenyl, 1-propynyl, 2-propynyl, 1-butynyl, 3-butynyl, and 2-pentynyl.

The term "alkoxy" as used herein, alone or in any combination, refers to an alkyl group with 1 to 7, preferably 1 to 4, carbon atoms appended to the parent molecular moiety through an oxygen bridge. Representative examples of alkoxy include, but are not limited to, methoxy, ethoxy, propoxy, 2-propoxy, butoxy, tert-butoxy, pentyloxy, and hexyloxy, especially methoxy.

The term "alkoxyalkyl", as used herein, alone or in any combination, refers to an alkoxy group appended to the parent molecular moiety through an alkyl group. Representative examples of alkoxyalkyl include, but are not limited to, tert-butoxymethyl, 2-ethoxyethyl, 2-methoxyethyl, and methoxymethyl.

The term "alkoxycarbonyl", as used herein, alone or in any combination, refers to an alkoxy group appended to the parent molecular moiety through a carbonyl group. Representative examples of alkoxycarbonyl include, but are not limited to, methoxycarbonyl, ethoxycarbonyl, and tert-butoxycarbonyl.

The term "alkoxycarbonylalkyl", as used herein, alone or in any combination, refers to an alkoxycarbonyl group appended to the parent molecular moiety through an alkyl group. Representative examples of alkoxycarbonylalkyl include, but are not limited to, methoxycarbonylmethyl, methoxycarbonylpropyl, ethoxycarbonylbutyl, and 2-tert-butoxycarbonylethyl.

The term "alkylcarbonyl" or "acyl", as used herein, alone or in any combination, refers to an alkyl group appended to the parent molecular moiety through a carbonyl group. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl", as used herein, alone or in any combination, refers to an alkylcarbonyl group appended to the parent molecular moiety through an alkyl group. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy", as used herein, alone or in any combination, refers to an alkylcarbonyl group appended to the parent molecular moiety through an oxygen bridge. Representative examples of alkylcarbonyloxy include, but are not limited to, acetyloxy, ethylcarbonyloxy, and tert-butylcarbonyloxy.

The term "alkylsulfinyl", as used herein, alone or in any combination, refers to an alkyl group appended to the parent molecular moiety through a sulfinyl group. Representative examples of alkylsulfinyl include, but are not limited to, methylsulfinyl and ethylsulfinyl.

The term "alkylsulfinylalkyl", as used herein, alone or in any combination, refers to an alkylsulfinyl group appended to the parent molecular moiety through an alkyl group. Representative examples of alkylsulfinylalkyl include, but are not limited to, methylsulfinylmethyl and ethylsulfinylmethyl.

The term "alkylsulfonyl", as used herein, alone or in any combination, refers to an alkyl group appended to the parent molecular moiety through a sulfonyl group. Representative examples of alkylsulfonyl include, but are not limited to, methylsulfonyl and ethylsulfonyl.

The term "alkylsulfonylalkyl", as used herein, alone or in any combination, refers to an alkylsulfonyl group appended to the parent molecular moiety through an alkyl group. Representative examples of alkylsulfonylalkyl include, but are not limited to, methylsulfonylmethyl and ethylsulfonylmethyl.

The term "alkylthio" (synonym "alkylsulfanyl"), as used herein, alone or in any combination, refers to an alkyl group appended to the parent molecular moiety through a thio group. Representative examples of alkylthio include, but are not limited to, methylthio, ethylthio, tert-butylthio, and hexylthio.

The term "alkylthioalkyl" (synonym "alkylsulfanylalkyl"), as used herein, alone or in any combination, refers to an alkylthio group appended to the parent molecular moiety through an alkyl group. Representative examples of alkylthioalkyl include, but are not limited to, methylthiomethyl and 2-(ethylthio)ethyl.

The term "amino", as used herein, alone or in any combination, refers to a —NR$_e$R$_f$ group, wherein R$_e$ and R$_f$ are substituents, each individually and independently selected from hydrogen, alkyl, aryl, arylalkyl, acyl, alkylcarbonyl, arylcarbonyl, carbamoyl, ureido, formyl, alkylsulfonyl, arylsulfonyl, and the like. Representative examples of amino include, but are not limited to, dimethylamino, ethylamino, and benzyl-(methyl)amino.

The term "aminoalkyl", as used herein, alone or in any combination, refers to an amino group appended to the parent molecular moiety through an alkyl group. Representative examples of aminoalkyl include, but are not limited to, aminomethyl, 2-(amino)ethyl, benzyl-(methyl)aminomethyl, and dimethylaminomethyl.

The term "aminocarbonyl" or "carbamoyl", as used herein, alone or in any combination, refers to an amino group appended to the parent molecular moiety through a carbonyl group. Representative examples of aminocarbonyl include, but are not limited to, dimethylaminocarbonyl, benzyl-aminocarbonyl, and ethylaminocarbonyl.

The term "aminocarbonylalkyl", as used herein, alone or in any combination, refers to an aminocarbonyl group appended to the parent molecular moiety through an alkyl group. Representative examples of aminocarbonylalkyl include, but are not limited to, 2-amino-2-oxoethyl, 2-(benzylamino)-2-oxoethyl, 2-(methylamino)-2-oxoethyl, 4-amino-4-oxobutyl, and 4-(dimethylamino)-4-oxobutyl.

The term "aryl", as used herein, alone or in any combination, refers to a carbocyclic group having at least one aromatic ring, e.g. phenyl or biphenyl, especially phenyl, or multiple condensed ring systems, in which at least one ring is aromatic, e.g. 1,2,3,4-tetrahydronaphthyl, naphthyl, anthryl, phenanthryl, and fluorenyl, especially 1,2,3,4-tetrahydronaphthyl, naphthyl or indanyl. The aryl group may be optionally substituted with one or more functional groups individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy (especially methylendioxy), alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro, and the like, such as also arylcarbonyl like especially phenylcarbonyl.

If R$^7$ and/or R$^8$ represents "aryl", this term preferably represents a phenyl or naphthyl, preferably a phenyl, radical, said radicals being optionally mono-substituted by halogen, alkyl, alkoxy, —CF$_3$, —OCF$_3$, phenyl-alkyl or phenyl-carbonyl; or di-substituted with a substituent independently selected from halogen, alkoxy and phenyl; and most preferably represents phenyl optionally mono-substituted by halogen, alkyl, alkoxy, —CF$_3$, —OCF$_3$, phenyl-alkyl or phenyl-carbonyl; phenyl, di-substituted with a substituent independently selected from halogen, alkoxy and phenyl; or naphthyl.

The term "arylalkenyl", as used herein, alone or in any combination, refers to an aryl group appended to the parent molecular moiety through an alkenyl group. The aryl group may be unsubstituted or substituted, especially as defined hereinabove for the aryl group. Representative examples of arylalkenyl include, but are not limited to, 2-phenylethenyl, 3-phenylpropen-2-yl, and 2-naphth-2-ylethenyl.

The term "aryl-alkoxy", as used herein, alone or in any combination, refers to an aryl group appended to the parent molecular moiety through an alkoxy group. The aryl group may be unsubstituted or substituted, especially as defined hereinabove for the aryl group. Representative examples of aryl-alkoxy include, but are not limited to, 2-phenylethoxy, 5-phenylpentyloxy, and 3-naphth-2-ylpropoxy. If R$^6$ is "aryl-alkoxy", this term preferably represents benzyloxy or 1-phenyl-ethoxy.

The term "arylalkyl", as used herein, alone or in any combination, refers to an aryl group appended to the parent molecular moiety through an alkyl group. The aryl group may be unsubstituted or substituted, especially as defined hereinabove for the aryl group.

Representative examples of arylalkyl include, but are not limited to, benzyl, 2-phenylethyl, 3-phenylpropyl, and 2-naphth-2-ylethyl, such as especially benzyl, phenylethyl, phenyl-propyl, 1-phenyl-ethyl, 2-phenyl-ethyl, diphenylmethyl, 4-phenyl-benzyl, 3,4-dichloro-benzyl, 2,4-dichloro-benzyl, difluoromethoxy-benzyl, 2-chloro-benzyl, 4-chloro-benzyl, 2-methylsulfanyl-benzyl, 2-fluoro-benzyl, 3-fluoro-benzyl, 4-fluoro-benzyl, 2-trifluoromethyl-benzyl, 3-trifluoromethyl-benzyl, 2,4-difluoro-benzyl, 2,5-difluoro-benzyl, 2,6-difluoro-benzyl, 3,5-difluoro-benzyl, 4-chloro-2-fluoro-benzyl, (2-fluoro-phenyl)-ethyl, (3-fluoro-phenyl)-ethyl, (4-fluoro-phenyl)-ethyl, (4-chloro-phenyl)-ethyl, (2,6-dichloro-phenyl)-ethyl, naphthalene-1-ylmethyl, and 2,2-diphenyl-ethyl.

If R$^7$ and/or R$^8$ represents "aryl-alkyl", this term preferably represents phenyl-alkyl optionally substituted in the alkyl moiety by phenyl or optionally substituted in the phenyl ring by methylendioxy; phenyl-alkyl which is di-substituted by halogen or mono-substituted by halogen, —CF$_3$, —OCHF$_2$, alkyl or alkylsulfanyl; or naphthyl-alkyl.

The term "aryloxy", as used herein, alone or in any combination, refers to an aryl group appended to the parent molecular moiety through an oxygen bridge. The aryl group can be unsubstituted or substituted, especially as defined hereinabove for the aryl group. Representative examples of aryloxy include, but are not limited to, phenoxy, naphthyloxy, 3-bromophenoxy, 4-chlorophenoxy, 4-methylphenoxy, and 3,4-dimethoxyphenoxy.

The term "carbamoyl", as used herein, alone or in any combination, refers to a —C(O)NR$_e$R$_f$ group. R$_e$ and R$_f$ are substituents, each individually and independently selected from hydrogen, alkyl, arylalkyl, and the like.

Similarly, the term "thiocarbamoyl", as used herein, alone or in any combination, refers to a —C(S)NR$_e$R$_f$ group.

The term "carbonyl", as used herein, alone or in any combination, refers to a —C(O)— group.

The term "carboxy", as used herein, alone or in any combination, refers to a —CO$_2$H group.

The term "carboxyalkyl", as used herein, alone or in any combination, refers to a carboxy group appended to the parent molecular moiety through an alkyl group. Representative examples of carboxyalkyl include, but are not limited to, carboxymethyl, 2-carboxyethyl, and 3-carboxypropyl.

The term "cyano", as used herein, alone or in any combination, refers to a —C≡N group.

The term "cyanoalkyl", as used herein, alone or in any combination, refers to a cyano group appended to the parent molecular moiety through an alkyl group. Representative examples of cyanoalkyl include, but are not limited to, cyanomethyl, 2-cyanoethyl, and 3-cyanopropyl, especially 2-cyanoethyl.

The term "cycloalkyl", as used herein, alone or in any combination, refers to a saturated cyclic hydrocarbon moiety containing 3-10 carbon atoms, optionally substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro, and the like. Representative examples of cycloalkyl include, but are not limited to, cyclopropyl, cyclobutyl, cyclopentyl, cyclohexyl, cycloheptyl, and cyclooctyl, especially cyclopentyl and cyclohexyl. In polycyclic cycloalkyl groups one of the distal rings may be aromatic, e.g., 1-indanyl, 2-indanyl, tetrahydronaphthyl, bicyclo[4.2.0]octa-1,3,5-trien-7-yl, and the like. If $R^7$ and/or $R^8$ represents "cycloalkyl", this term preferably represents a cyclopentyl or cyclohexyl radical, said radicals, especially the cyclohexyl radical, being optionally substituted with an annellated benzene ring.

The terms "cycloalkenyl" and "cycloalkynyl", as used herein, alone or in any combination, refer to unsaturated cyclic hydrocarbon moieties containing at least one carbon-carbon double or carbon-carbon triple bond, respectively. Such moieties may optionally be substituted with one or more groups as discussed hereinabove for the cycloalkyl groups.

The term "formyl", as used herein, alone or in any combination, refers to a —C(O)H group.

The term "formylalkyl", as used herein, alone or in any combination, refers to a formyl group, appended to the parent molecular moiety through an alkyl group. Representative examples of formylalkyl include, but are not limited to, formylmethyl and 2-formylethyl.

The term "halo" or "halogen", as used herein, alone or in any combination, refers to fluorine, bromine, chlorine, and iodine.

The term "haloalkyl", as used herein, alone or in any combination, refers to an alkyl group having at least one hydrogen atom replaced with a halogen atom. Representative examples of haloalkyl include, but are not limited to, chloromethyl, 2-fluoroethyl, trifluoromethyl, pentafluoroethyl, and 2-chloro-3-fluoropentyl.

The term "haloalkoxy", as used herein, alone or in any combination, refers to an alkoxy group having at least one hydrogen atom replaced with a halogen atom. Representative examples of haloalkoxy include, but are not limited to, chloromethoxy, 2-fluoroethoxy, trifluoromethoxy, and pentafluoroethoxy.

The term "heterocyclyl", as used herein, alone or in any combination, refers to a monocyclic, bicyclic or polycyclic ring system containing up to 15 ring atoms, at least one of these being a heteroatom, preferably one to three heteroatoms, independently selected from nitrogen, oxygen or sulfur. The ring system may be saturated, partially unsaturated, unsaturated or aromatic, mono- or bicyclic. Representative examples of heterocyclyl include, but are not limited to, furyl, imidazolyl, imidazolinyl, imidazolidinyl, isothiazolyl, isoxazolyl, morpholinyl, oxadiazolyl, oxazolyl, oxazolinyl, oxazolidinyl, piperazinyl, piperidinyl, pyranyl, pyrazinyl, pyrazolyl, pyridyl, pyrimidinyl, pyridazinyl, pyrrolyl, pyrrolinyl, pyrrolidinyl, tetrahydrofuranyl, tetrahydrothienyl, thiadiazolyl, thiazolyl, thiazolinyl, thiazolidinyl, thienyl, thiomorpholinyl, 1,1-dioxothiomorpholinyl, benzimidazolyl, phthalazinyl, benzothiazolyl, benzothienyl, benzoxazolyl, benzofuranyl, indolyl, indolinyl, indazolyl, isobenzofuranyl, isobenzothienyl, isoindolyl, isoindolinyl, isoquinolinyl, quinolinyl, and quinazolinyl. Defined heterocyclyl moieties may be optionally substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, arylcarbonyl, arylalkylcarbonyl, (diaryl)alkylcarbonyl, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, cycloalkyl, cycloalkylcarbonyl, cycloalkylalkylcarbonyl, formyl, formylalkyl, halogen, haloalkoxy, haloalkyl, heterocyclyl, heterocyclylcarbonyl, hydroxy, hydroxyalkyl, mercapto, nitro, and the like.

If $R^7$ and $R^8$, together with the nitrogen atom to which they are attached, form a heterocyclic 5-, 6-, 7-, or 8-membered ring system, this ring system may be saturated, partially saturated or unsaturated, preferably saturated or partially saturated (partially saturated preferably meaning that 1 double bond is present), and preferably contains one or two ring heteroatoms selected from nitrogen, and which ring system is optionally substituted as defined for Formula I. Preferably the ring system is optionally substituted with (i) one or two annellated benzene rings, which benzene rings are unsubstituted or substituted with one or two substituents independently selected from alkoxy and —$CF_3$; (ii) a mono-substituted phenyl ring substituted with halogen; or (iii) phenyl-alkyl, wherein the alkyl moiety is substituted with phenyl.

The term "heteroaryl", as used herein, alone or in any combination, is a special case of heterocyclyl and refers to a mono- or bicyclic or polycyclic aromatic ring system, in which at least one heterocyclic ring is aromatic.

The term "saturated heterocyclyl" is another special case of "heterocyclyl" and refers to saturated rings as defined above for "heterocyclyl".

The term "heterocyclylalkenyl", as used herein, alone or in any combination, refers to a heterocyclyl group appended to the parent molecular moiety through an alkenyl group. Representative examples of heterocyclylalkenyl include, but are not limited to, 2-pyrid-3-ylethenyl, 3-quinolin-3-ylpropen-2-yl, and 5-pyrid-4-ylpenten-4-yl.

The term "heterocyclylalkoxy", as used herein, alone or in any combination, refers to a heterocyclyl group appended to the parent molecular moiety through an alkoxy group. Representative examples of heterocyclylalkoxy include, but are not limited to, 2-pyrid-3-ylethoxy, 3-quinolin-3-ylpropoxy, and 5-pyrid-4-ylpentyloxy.

The term "heterocyclylalkyl", as used herein, alone or in any combination, refers to a heterocyclyl group appended to the parent molecular moiety through an alkyl group. Representative examples of heterocyclylalkyl include, but are not limited to, 2-pyrid-3-ylmethyl and 2-pyrimidin-2-ylpropyl.

The term "heterocyclyloxy", as used herein, alone or in any combination, refers to a heterocyclyl group appended to the parent molecular moiety through an oxy group. Representative examples of heterocyclyloxy include, but are not limited to, pyrid-3-yloxy and quinolin-3-yloxy.

The term "hydroxy" or "hydroxyl" as used herein, alone or in any combination, refers to an —OH group The term "hydroxyalkyl", as used herein, alone or in any combination, refers to an alkyl group having at least one hydrogen atom replaced by a hydroxy group. Representative examples of hydroxyalkyl include, but are not limited to, hydroxymethyl, 2-hydroxyethyl, 3-hydroxypropyl, and 2-ethyl-4-hydroxyheptyl.

The term "nitro", as used herein, alone or in any combination, refers to a —$NO_2$ group.

The term "oxo", as used herein, alone or in any combination, refers to an =O group.

The term "oxy", as used herein, alone or in any combination, refers to an —O— group.

The terms "mercapto" and "thiol", as used herein, alone or in any combination, refer to an —SH group.

The terms "thio" (synonym "sulfanyl"), "sulfinyl" and "sulfonyl", as used herein, alone or in any combination, refer to a —$S(O)_n$ group with n=0, 1 and 2, respectively.

Within the scope of the present invention, unless indicated otherwise, compounds of Formula I or pharmaceutically acceptable salts thereof are included, that may exist in, and be isolated in, isomeric forms, including cis- or trans-isomers or mixtures thereof, and tautomers. Other compounds of this invention may contain one or more stereogenic or asymmetric centers, such as one or more asymmetric carbon atoms, and thus may give rise to optically pure enantiomers, mixtures of enantiomers, racemates, enantiomer-pure diastereomers, mixtures of diastereomers, epimers, and other stereoisomeric forms that may be defined, in terms of absolute stereochemistry, as (R)-, (S)- or (R,S)-configured, preferably in the (R)- or (S)-configuration. Such isomers can be obtained by methods within the knowledge of one skilled in the art, e.g. by stereochemically controlled synthesis using chiral synthons or chiral reagents, or by means of classical separation techniques, such as chromatographic or crystallization methods, or by other methods known in the art, such as through formation of diastereomeric salts, for example by salt formation with an enantiomerically pure chiral acid, or with an enantiomerically pure chiral base, or by means of chromatography, for example by using chromatographic materials modified with chiral ligands. Furthermore, the present invention refers to compounds containing centers of any geometric asymmetry, like, for example, unsymmetrically substituted olefinic double bond, including E or Z geometric isomers and mixtures thereof. Generally, pure isomers of compounds of Formula I are preferred over isomeric mixtures.

In the present invention, the compounds of Formula I may be used in the form of pharmaceutically acceptable salts. The term "pharmaceutically acceptable salts" refers to relatively nontoxic, inorganic or organic acid and base addition salts, which retain the biological effectiveness and properties of the parent compound, and which are not biologically or otherwise undesirable (see, e.g. Berge et al., *J. Pharm. Sci.* 1977, 66, 1-19).

Certain compounds of the present invention can contain one or more basic functional groups, such as amino, alkylamino, or arylamino, and, thus, be capable of forming pharmaceutically acceptable acid addition salts. These acid addition salts may be prepared by standard procedures in a suitable solvent from the parent compound of Formula I, with an appropriate amount of an inorganic acid, including, but not limited to, for example, hydrochloric acid, hydrobromic acid, sulfuric acid, or phosphoric acid; or of an organic acid, including, but not limited to, acetic acid, propionic acid, octanoic acid, decanoic acid, glycolic acid, pyruvic acid, oxalic acid, maleic acid, malonic acid, succinic acid, fumaric acid, tartaric acid, citric acid, ascorbic acid, amino acids, such as glutamic acid or aspartic acid, benzoic acid, cinnamic acid, salicylic acid, mandelic acid, methanesulfonic acid, ethanesulfonic acid, p-toluenesulfonic acid, or other acidic organic compounds.

Certain compounds of the present invention may, on the other hand, contain one or more acidic functional groups and, thus, be capable of forming pharmaceutically acceptable base addition salts. These salts can be prepared by addition of an appropriate amount, usually in stoichiometric ratio, of an alkaline reagent, such as hydroxide, carbonate or alkoxide, containing the appropriate cation, to the free acid in a suitable solvent. Preferred inorganic salts include, but are not limited to, ammonium, sodium, potassium, calcium or magnesium, also zinc salts and the like. Preferred salts derived from organic bases include, but are not limited to, salts of primary, secondary, and tertiary amines, substituted amines, cyclic amines, and basic ion exchange resins, such as isopropylamine, trimethylamine, diethylamine, triethylamine, tripropylamine, ethanolamine, lysine, arginine, N-ethylpiperidine, piperidine, polyamine resins, and the like.

Compounds of the present invention containing both acidic and basic groups can also form internal salts (zwitter ions).

For isolation or purification purposes, it is also possible to use pharmaceutically unacceptable salts, for example perchlorates, picolinates, picrates, or the like. For therapeutic use, only pharmaceutically acceptable salts or free compounds are employed, where applicable in the form of pharmaceutical preparations, and these are therefore preferred.

Certain compounds of Formula I, including their salts, may exist in solvated as well as unsolvated forms, such as, for example, hydrated forms, or their crystals may, for example, include the solvent used for crystallization. Different crystalline forms may be present. The present invention encompasses all such solvated and unsolvated forms.

The present invention also relates to prodrug derivatives of the parent compounds of Formula I. The term "prodrug" refers to pharmacologically inactive precursors of a drug that may be converted into its therapeutically active form under physiological conditions in vivo, for example, when they undergo solvolysis, or enzymatic degradation in blood, or in cells, (Bundgard H., in *Design of Prodrugs*, pp. 7-9, 21-24, Elsevier, Amsterdam (1985); Silverman R. B., in *The Organic Chemistry of Drug Design and Drug Action*, pp. 352-401, Academic Press, San Diego, Calif. (1992); Higuchi T. et al., "Pro-drug as Novel Delivery Systems", A.C.S. Symposium Series, Vol. 14). The term "prodrug" also includes any covalently bonded carriers, which release the active parent compound in vivo when administered to a mammal. Prodrug modifications of a compound often offer advantages of solubility, bioavailability, absorption, tissue compatibility, tissue distribution, or delayed release in the mammalian organism. Prodrugs are variations or derivatives of the compounds of Formula I, which have groups cleavable under metabolic conditions, for example, pharmaceutically acceptable esters, or amides. Such groups can be cleaved enzymatically or non-enzymatically, or hydrolytically to the free hydroxy, carboxy, or amino group of the active parent compound. In another embodiment, the prodrug is a reduced form, which is oxidized in vivo to the therapeutic compound, for example, a thiol, which is oxidized to a sulfonate or sulfate, or an alcohol which is oxidized to a carboxylic acid.

Further included within the scope of the present invention are pharmaceutically acceptable esters of the compounds of Formula I. The term "pharmaceutically acceptable esters" refers to relatively non-toxic, esterified products of the parent compound. These esters can be prepared in situ during the final isolation and purification of the compounds, or by separately reacting the purified compounds in its free acid or hydroxyl form with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term further includes lower hydrocarbon groups capable of being solvated under physiological conditions, for example, alkyl esters, preferred methyl, ethyl, and propyl esters, methoxymethyl ester, methylthiomethyl ester, pivaloyloxymethyl ester and the like (see, e.g. Berge et al., *J. Pharm. Sci.* 1977, 66, 1-19).

The compounds of the present invention have useful, in particular pharmacologically useful, properties. They are able to specifically antagonize the effect of endogenous $PGD_2$ on the CRTH2 receptor, and may be used for the prevention and/or treatment of chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, and basophil-related diseases, comprising basophilic leukemia and basophilic leukocytosis, in humans and other mammals.

A compound or a pharmaceutical composition of the invention may be used as a drug (medicine) or therapeutic agent for prevention and/or treatment of both chronic and acute allergic/immune disorders such as allergic asthma, rhinitis, COPD, dermatitis, inflammatory bowel disease, rheumatoid arthritis.

In another aspect, the compounds of Formula I may be used as standard or reference compounds in tests or assays involving the inhibition of the CRTH2 receptor. Such compounds could be made commercially available for use as a reference, quality standard or control, for example in pharmaceutical research when developing new assays or protocols related to CRTH2 activity.

As mentioned earlier, compounds of Formula I, or salts, or prodrugs thereof, antagonize the $PGD_2$ activation of the CRTH2 receptor. The biological effect of such compounds may be tested in a variety of in vitro, ex vivo and in vivo assays.

The ability of the compounds of Formula I to bind to the CRTH2 receptor may be measured by methods similar to those described in Sawyer N. et al., *Br. J. Pharmacol.,* 2002, 137, 1163-1172 and by the method described below in the experimental part.

With this type of assay, $IC_{50}$ values (i.e. the concentrations where half-maximal inhibition of the interaction is found) in the range of 0.001 to 10 µM, preferably values below 1 µM, in particular values below 0.05 µM, are found with test compounds of Formula I. Exemplary $IC_{50}$ values determined in this test are given below in Table 4.

A functional assay with cells expressing the human CRTH2 receptor may be used to detect changes in the levels of intracellular calcium concentration following compound treatment. After addition of the compound the cells are challenged with $PGD_2$. In a Fluorescent Imaging Plate Reader (FLIPR™, Molecular Devices, Sunnyvale, Calif.) fluorescence emission is recorded during both additions, emission peak values above base level after $PGD_2$ addition were exported, normalized to low controls (no $PGD_2$) and high controls (no active compound). The relative values of the remaining activity were used to determine $IC_{50}$ values by curve fitting the data to a single site to a four-parameter logistic sigmoid dose response curve of the equation $(A+((B-A)/(1+((C/x)^{\wedge}D))))$.

The ability of the compounds to inhibit $PGD_2$ induced change of intracellular calcium levels via CRTH2 activation may be measured by methods known to one skilled in the art or by the method described below in the experimental part.

With this assay, $IC_{50}$ values (i.e. the concentration of a compound at which the remaining activity is 50%) in the range of 0.001 and 10 µM, preferably below 0.5 µM, are obtained with test compounds of Formula I. Exemplary $IC_{50}$ values determined in this test are given below in Table 5.

The results of these assays clearly demonstrate, that the present invention provides functional antagonists of the $PGD_2$ receptor.

On the basis of the biological studies discussed hereinabove, a compound of Formula I according to the invention may show therapeutic efficacy against chronic and acute allergic/immune disorders such as allergic asthma, rhinitis, chronic obstructive pulmonary disease (COPD), dermatitis, inflammatory bowel disease, and rheumatoid arthritis.

A compound of Formula I, a pharmaceutically acceptable salt or a prodrug thereof, can be administered alone in pure form or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula I can besides or in addition be administered especially for prevention and/or treatment of both chronic and acute allergic disorders or immune disorders in combination with other inflammatory diseases. Long-term therapy is equally possible as is adjuvant therapy in the context of other treatment strategies, as described above. Other possible treatments are preventive therapies, for example in patients at risk.

The invention relates also to pharmaceutical compositions comprising compounds of Formula I, to their use in therapeutic, in a broader aspect of the invention also prophylactic treatment or a method of treatment of the diseases mentioned above, to the compounds for said use and to the preparation of pharmaceutical formulations (medicines).

The pharmaceutically acceptable compounds of the present invention may be used, for example, for the preparation of pharmaceutical compositions that comprise an effective amount of the active ingredient together or in admixture with a significant amount of one or more inorganic, organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, for the treatment or, in a broader aspect of the invention, prevention of (i.e. prophylaxis against) a disease that responds to blockade of the interaction of the CRTH2 receptor with $PGD_2$, comprising an amount of a compound of Formula I or a pharmaceutically acceptable salt or a prodrug thereof; which is effective for said inhibition, together with at least one pharmaceutically acceptable carrier.

The pharmaceutical compositions according to the invention are those for enteral administration, such as nasal, buccal, rectal, dermal or, especially oral administration, and for parenteral administration, such as intramuscular, intravenous or subcutaneous, intrasternal, intravitreal, injection or infusion, to warm-blooded animals, especially humans. Such compositions comprise an effective dose of the pharmaceutically active ingredient, alone or together with a significant amount of a pharmaceutically acceptable carrier. The dosage of the active ingredient depends on the species of warm-blooded animal, the body weight, the age and the individual conditions, individual pharmacokinetic data, the disease to be treated and the mode of administration.

The invention relates also to a process or a method for the treatment of a pathological condition mentioned hereinabove, especially a disease, which responds to blockade of the interaction of the CRTH2 receptor with $PGD_2$, especially allergic asthma, rhinitis, chronic obstructive pulmonary disease (COPD), dermatitis, inflammatory bowel disease, and rheumatoid arthritis. The compounds of Formula I or salts or prodrugs thereof can be administered as such or especially in the form of pharmaceutical compositions.

The dose to be administered to warm-blooded animals, for example humans of approximatively 70 kg body weight, is preferably from approximatively 3 mg to approximatively 3000 mg, more preferably from approximatively 10 mg to approximatively 1000 mg per person per day, divided preferably into 1 to 3 single doses which may, for example, be of the same size. The amount of the compound actually administered will typically be determined by a physician, in the light of the relevant circumstances, including the condition to be treated, the chosen route of administration, the actual compound administered, the age, the weight, and response of the individual patient, the severity of the patient's symptoms, and the like, for example, children usually receive half of the adults dose.

The pharmaceutical compositions comprise from approximately 1% to approximately 95%, preferably from approximately 20% to approximately 90%, active ingredient. Pharmaceutical compositions according to the invention may be, for example, in unit dosage forms such as coated and uncoated tablets, pills, ampoules, vials, suppositories, dragées, or capsules. Further dosage forms are, for example, ointments, creams, pastes, emulsions, foams, chewable gums, tinctures, lip-sticks, drops, sprays or aerosols, syrups or elixirs, dispersions, transdermal patches or pads, or via an intravitreal device that releases the compound in a sustained capacity, and the like. Examples are capsules containing from about 0.05 g to about 1.0 g active ingredient.

The pharmaceutical compositions of the present invention are prepared in a manner known, per se, for example by means of conventional mixing, granulating, coating, dissolving, lyophilizing or confectioning processes.

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chain fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is mono- or poly-hydroxy, for example a mono-, di- or trihydroxy, alcohol, for example methanol, ethanol, propanol, butanol, or pentanol or the isomers thereof, but especially glycol and glycerol. The following examples of fatty acid esters are therefore to be mentioned: ethyl oleate, isopropyl myristate, isopropyl palmitate, "Labrafil M2375" (polyoxyethylene glycerol trioleate, Gattefossé, Paris), "Miglyol 812" (triglyceride of saturated fatty acids with chain lengths of C8 to C12, Hüls AG, Germany), but especially vegetable oils, such as cottonseed oil, almond oil, olive oil, castor oil, sesame oil, soybean oil and more especially groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice, or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum Arabic, talc, polyvinylpyrrolidone, polyethylene glycol, and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and of soft sealed capsules made of gelatine and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oil excipients, such as fatty oils, paraffin oil or liquid polyethylene glycols, it being possible also for stabilizers and/or antibacterial agents to be added. Dyes or pigments may be added to the tablets or dragée coatings or the capsule casings, for example for identification purposes or to indicate different doses of active ingredient.

For parenteral administration, aqueous solutions of an active ingredient in water-soluble form, for example of a water-soluble salt, or aqueous injection suspensions that contain viscosity-increasing substances and stabilizers, are especially suitable. The active ingredient, optionally together with excipients, can also be in the form of a lyophilizate and be made into a solution before parenteral administration by the addition of solvents.

A further object of the invention is a process for preparing 2,3,4,9-tetrahydro-1H-carbazole compounds of Formula I. Compounds according to Formula I of the present invention can be prepared according to the general sequence of reactions outlined in Scheme 1 below. The compounds obtained may also be converted into a pharmaceutically acceptable salt thereof in a manner known per se.

Compounds of the invention may be manufactured by the application or adaptation of known methods, by which is meant methods used heretofore or described in the literature, for example those described by Larock R. C. in "*Comprehensive organic transformations: a guide to functional group preparations*", VCH publishers, 1999. In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example see Greene T. W. and Wuts P. G. M. in "*Protective groups in organic synthesis*" Wiley-Interscience (1999).

Generally, the key step to build up a 2,3,4,9-tetrahydro-1H-carbazole compound of Formula I comprises a Fischer indole reaction known to a skilled person (e.g. M. H. Block et al., *J. Med. Chem.* 2002, 45, 3509-3523). In such a reaction, a phenylhydrazine of Formula 1, wherein $R^1$, $R^2$, $R^3$, and $R^4$ are as defined for Formula I, and A represents hydrogen, $CH_2COOH$ or $CH_2COOalkyl$, is condensed with a cyclohexanone derivative of Formula 2, wherein B represents hydroxy or alkoxy, and $R^5$ is as defined for Formula I, in the presence of an acid, such as hydrochloric acid, in a solvent such as ethanol, etc., as outlined in Scheme 1.

Scheme 1

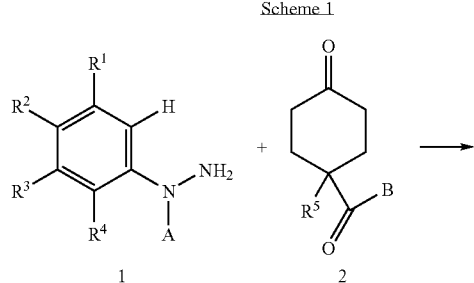

A compound of Formula 5

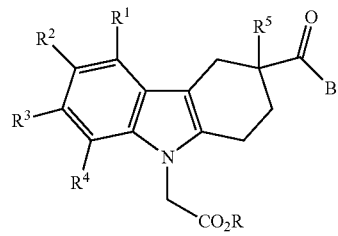

is obtained in an alkylation reaction from an intermediate of Formula 4

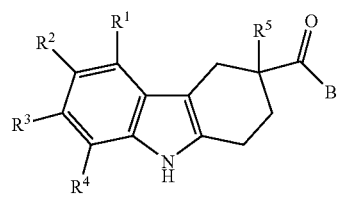

with an alkylating reagent of Formula $L-CH_2CO_2R$, wherein R represents an alkyl group, preferably ethyl or tert.-butyl, and L is a leaving group, in the presence of a base, such as cesium carbonate, sodium hydride, potassium tert.-butoxide or the like, in a suitable solvent, such as acetone, tetrahydrofuran, dioxane or N,N-dimethylformamide.

Suitable leaving groups L are such as halo, in particular bromo or chloro, mesyloxy or tosyloxy. Preferably, the compound of Formula $L-CH_2CO_2R$ is ethyl bromo-acetate.

A precursor of Formula 6

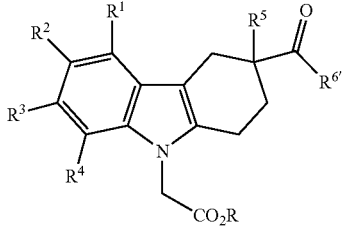

wherein $R^{6'}$ represents $-NR^7R^8$ as defined hereinabove for Formula I, and R represents alkyl, is obtained by condensing an intermediate of Formula 7

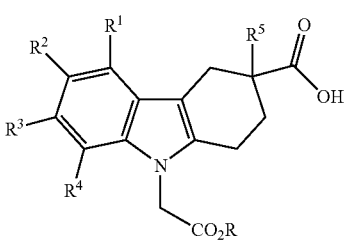

with a primary or secondary amine of Formula $HNR^7R^8$ by means of standard coupling reagents such as 1,3-dicyclohexylcarbodiimide, 1,3-diisopropylcarbodiimide, O-(7-aza-benzotriazol-1-yl)-N,N,N',N'-tetramethyluronium hexafluorophosphate and the like, in the presence of a base; or via the corresponding acid halide of Formula 8

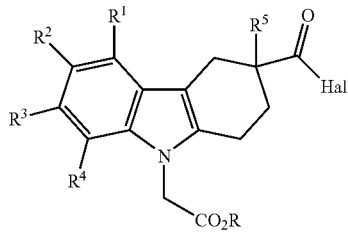

wherein Hal represents halogen, preferably chloro or bromo, in the presence of a base. The acid halide is obtained by reacting the corresponding acid with a halogenating reagent under conditions known to a skilled person, preferably by means of oxalyl chloride in the presence of a catalytic amount of N,N-dimethylformamide, phosphorous oxychloride or bis(trichloromethyl)carbonate.

A precursor of Formula 9

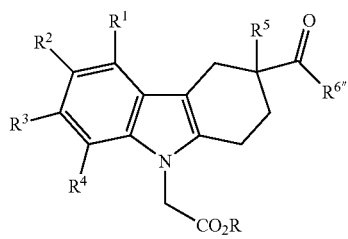

wherein $R^{6''}$ represents alkoxy or aryl-alkoxy, and R represents alkyl, is obtained by condensing the corresponding carboxylic acid with a reagent of Formula X-$R^{6''}$, wherein X is a leaving group such as halogen, in particular chloro or bromo; or alkyl- or arylsulfonate, such as mesylate or tosylate; in the presence of a base.

Hydrolysis of the $CO_2R$ group in Formula 10

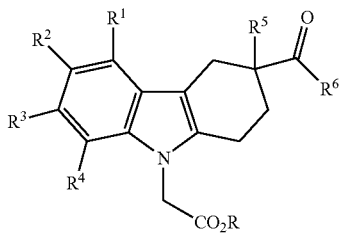

is carried out using routine procedures, for example by treatment with aqueous sodium hydroxide or lithium hydroxide; or trifluoroacetic acid or hydrochloric acid, to give a compound of Formula I.

A precursor of Formula 11

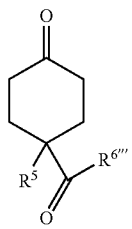

wherein $R^{6'''}$ represents —$NR^7R^8$ and $R^7$ and $R^8$ are as defined hereinabove for Formula I, is obtained by condensing the corresponding 4-oxo-cyclohexanecarboxylic acid with a primary or secondary amine of Formula $HNR^7R^8$ by means of a standard coupling reagent such as 1,3-dicyclohexylcarbodiimide, 1,3-diisopropylcarbodiimide, O-(7-azabenzotriazol-1-yl)-N,N,N',N'-tetramethyluronium hexafluorophosphate and the like, in the presence of a base; or via the corresponding 4-oxo-cyclohexanecarbonyl halide, preferably chloride or bromide, in the presence of a base. The acid halide is obtained by reacting the corresponding acid with a halogenating reagent under conditions known to a skilled person, preferably by means of oxalyl chloride, or phosphorous oxychloride, or bis(trichloromethyl)carbonate.

A precursor of above Formula 11, wherein $R^{6'''}$ represents alkoxy, or aryl-alkoxy, and R represents alkyl, is obtained by condensing the corresponding carboxylic acid with a reagent of Formula X-$R^{6'''}$, wherein X is a leaving group such as halogen, in particular chloro or bromo; or alkyl- or arylsulfonate, such as mesylate or tosylate, respectively, in the presence of a base.

4-Oxo-cyclohexanecarboxylic acid of Formula 12

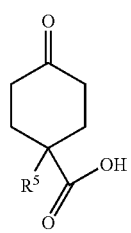

wherein $R^5$ is alkyl (other than hydrogen), is easily accessed by means of known methods (e.g. *J. Am. Chem. Soc.* 1946, 68, 338-340).

A phenyl hydrazine of Formula 13

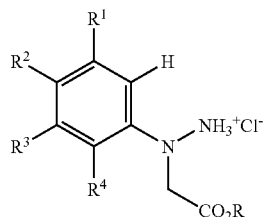

is prepared in three steps according to known methods starting from the corresponding aniline:

(i) alkylation with an alkylating reagent of Formula L-CH$_2$CO$_2$R, wherein R represents an alkyl group, preferably ethyl or tert.-butyl, and L is a leaving group as defined above in the reaction with a compound of Formula 4, in the presence of a base, such as ethyl-diisopropyl-amine, cesium carbonate, sodium hydride, potassium tert.-butoxide or the like, in a suitable solvent, such as acetone, acetonitrile, tetrahydrofuran, dioxane or N,N-dimethylformamide. Suitable L is a leaving group such as halo, in particular bromo or chloro; or mesyloxy or tosyloxy (preferably, the compound of Formula L-CH$_2$CO$_2$R is ethyl bromo-acetate);
(ii) nitrosation by means of sodium nitrite, or amylnitrite, in hydrochloric acid; (iii) and subsequent reduction with zinc metal in acetic acid.

Suitable are organic solvents, which are inert under the chosen reaction conditions. Preferred solvents are ethers, such as diethyl ether, diisopropyl ether, 2-methoxy-2-methyl-propane, [1,4]dioxane, tetrahydrofuran or 1,2-dimethoxy-ethane; or alcohols, such as methanol, ethanol, propanol, isopropanol, butanol, isobutanol or tert-butanol; or hydrocarbons, such as benzene, toluene, xylene, hexane, cyclohexane or petroleum derived hydrocarbons, or halogenated hydrocarbons, such as dichloromethane, trichloro-methane, tetrachloromethane, dichloroethane, trichloroethane or chlorobenzene; or esters, such as ethyl acetate; or amines, such as triethylamine, 4-methyl-morpholine, pyridine, and the like; as well as dimethylsulfoxide, N,N-dimethyl-formamide, N-methyl-pyrrolidone, N,N-dimethyl-acetamide, hexamethyl-phosphoric triamide, acetonitrile, acetone or nitromethane. Likewise, mixtures of above-mentioned solvents can be employed.

Suitable bases used in the processes described herein can be of inorganic or organic nature. Preferred are alkali metal hydroxide, for example lithium, sodium or potassium hydroxide, earth alkali metal hydroxide, for example barium hydroxide, alkali metal carbonate such as sodium or potassium carbonate, earth alkali metal carbonate, such as calcium carbonate, or alkali metal or earth alkali metal alkoxide, such as sodium or potassium methoxide, ethoxide, or tert-butoxide; or organic amines, for example trialkyl-(C$_1$-C$_6$)-amine, such as triethylamine, ethyl-diisopropyl-amine, or heterocyclic amines, such as 1,4-diazabicyclo[2.2.2]octane (DABCO), 1,8-diazabicyclo[5.4.0]undec-7-ene (DBU), pyridine, 2,6-lutidine, 4-dimethylamino-pyridine, 1-methyl-piperidine or 4-methyl-morpholine. Furthermore, alkali metals, such as sodium, or hydrides thereof, such as sodium hydride, can be employed. The above-mentioned bases can be used as antacid agents.

Suitable coupling reagents act as dehydrating reagents, for example carbodiimides, such as diisopropylcarbodiimide, dicyclohexylcarbodiimide, or N-(3-dimethylaminopropyl)-N'-ethylcarbodiimide hydrochloric acid salt; or carbonyl compounds, like carbonyldiimidazole, or 1,2-oxazolium compounds, like 2-ethyl-5-phenyl-isoxazolium-3-sulfonate, as well as 2,4,6-tripropyl-1,3,5,2,4,6-trioxatriphosphorinane-2,4,6-trioxide (PPACA; propanephosphonic acid cyclic anhydride), or alkyl chloroformates, such as iso-butyl chloroformate; or (benzotriazol-1-yloxy)-tris-(dimethylamino)-phosphonium-hexafluorophosphate (BOP), O-(benzotriazol-1-yl)-N,N,N',N'-tetramethyluronium-tetrafluoroborat (TBTU), N'N',N',N'-tetramethyl-O-(7-azabenzotriazole-1-yl)-uronium-hexafluorophosphate (HATU) and the like; or bis(trichloromethyl)carbonate, or diphenylphosphoramidate, or methanesulfonyl chloride; if indicated in the presence of a base such as triethylamine, or 4-ethyl-morpholine, or 4-methyl-piperidine, or ethyl-diisopropyl-amine.

Particular embodiments of the invention are described in the following Examples, which serve to illustrate the invention in more detail without limiting its scope in any way.

Experimental Part

Abbreviations (as Used Herein):
AcOH acetic acid
BSA Bovine Serum Albumine
calcd calculated
CH$_2$Cl$_2$ dichloromethane
CDCl$_3$ deuterated chloroform
conc. concentrated
DIEA ethyl-diisopropyl-amine
DMAP 4-N,N-Dimethylaminopyridine
DMF N,N-dimethylformamide
DMSO dimethylsulfoxide
EDTA ethylenediaminetetraacetic acid
ESI-MS electrospray ionization-mass spectrometry
Et ethyl
EtOAc ethyl acetate
EtOH ethanol
Ex. Example
FLIPR Fluorescent Imaging Plate Reader
g gram(s)
h hour(s)
HBSS Hank's Balanced Salt Solution
HEPES 4-(2-hydroxyethyl)-piperazine-1-ethanesulfonic acid
H$_2$O water
HCl hydrochloric acid
HPLC High-Performance Liquid Chromatography
H$_2$SO$_4$ sulfuric acid
k kilo
K$_2$CO$_3$ potassium carbonate
KH$_2$PO$_4$ potassium dihydrogenphosphate
KOtBu potassium tert-butoxide
l liter(s)
LC liquid chromatography
μ micro
m milli
M molar
MeOH methanol
min minute(s)
mol mole(s)
MS Mass Spectroscopy
MW molecular weight
N normality of solution
NaH sodium hydride
NaCl sodium chloride
NaHCO$_3$ sodium hydrogencarbonate
Na$_2$CO$_3$ sodium carbonate
NaNO$_2$ sodium nitrite
NaOAc sodium acetate
NaOH sodium hydroxide
Na$_2$SO$_4$ sodium sulfate
t$_R$ retention time
rt room temperature
THF tetrahydrofuran
TBME tert-butylmethylether
TFA trifluoroacetic acid
Chemistry
General Remarks:
All solvents and reagents are used as obtained from commercial sources unless otherwise indicated. The starting materials are obtained from commercial sources or synthesized using standard literature procedures.

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

Preparative chiral separations are performed on a HPLC instrument, equipped with a Dinoex P580 binary pump and a Photodiode Array Detector Dionex PDA-100, using a Daicel Chiralcel OD column (20×250 mm, 10 µm) under isocratic elution conditions (% B) employing EtOH (eluent A) and hexane (eluent B), run time 30 min; flow rate 10 ml/min, detection at 220 nm. The compounds are dissolved in EtOH before loading.

HPLC/MS analyses (LC-1 to LC-4) are performed on a Waters 2795 Alliance HPLC instrument, equipped with a Waters 996 Photodiode Array Detector and a Micromass ZQ™ Waters mass spectrometer (electron spray ionization), detection at 200-400 nm, or on a Agilent 1100 system, equipped with a Dionex P580 binary pump, a Dionex PDA-100 Photodiode Array Detector and a Finnigan AQA mass spectrometer (LC-5).

LC-1: Analytical HPLC on a Waters Xterra™ MS $C_{18}$ column (2.1×50 mm, 5 µm). Linear gradient of water/0.06% formic acid (A) and acetonitrile/0.06% formic acid (B) from 5% to 95% B over 2 min; flow rate 0.75 ml/min.

LC-2: Analytical HPLC on a Waters Xterra™ MS $C_{18}$ column (4.6×50 mm, 5 µm). Linear gradient of water/0.06% formic acid (A) and acetonitrile/0.06% formic acid (B) from 5% to 95% B over 1 min; flow rate 3 ml/min.

LC-3: Analytical HPLC on a GromSil MS $C_{18}$ column (2.1×50 mm, 5 µm, Waters). Linear gradient of water/0.06% formic acid (A) and acetonitrile/0.06% formic acid (B) from 5% to 95% B over 6 min; flow rate 0.25 ml/min.

LC-4: Analytical HPLC on a Zorbax SB-AQ column (4.6×50 mm, 5 µm): Linear gradient of water/0.06% formic acid (A) and acetonitrile/0.06% formic acid (B) from 5% to 95% B over 1 min; flow rate 3 ml/min.

LC-5: Analytical HPLC on a Zorbax SB-AQ column (50×4.6 mm, 5 µm): Linear gradient of water/0.04% trifluoroacetic acid (A) and acetonitrile (B) from 5% to 95% B over 1 min; flow rate 4.5 ml/min, detection at 210, 220, 230, 254 and 280 nm.

LC-6: Analytical chiral HPLC performed on a HPLC instrument, equipped with a Dinoex P580 binary pump, a Dionex PDA-100 Photodiode Array Detector and a Jasco OR-1590 Chiral Detector, using a Daicel Chiralcel OD column (4.6×250 mm, 10 µm) under isocratic elution conditions (75% B) employing EtOH/0.1% TFA (eluent A) and hexane (eluent B), run time 30 min; flow rate 0.8 ml/min, detection at 210 nm.

LC-7: Analytical chiral HPLC performed on a HPLC instrument, equipped with a Dinoex P580 binary pump, a Dionex PDA-100 Photodiode Array Detector and a Jasco OR-1590 Chiral Detector, using a Daicel ChiralPak IA column (4.6×250 mm, 5 µm) under isocratic elution conditions (95% B) employing EtOH/0.1% TFA (eluent A) and hexane (eluent B), run time 40 min; flow rate 1.0 ml/min, detection at 220 nm.

LC-8: Analytical chiral HPLC performed on a HPLC instrument, equipped with a Dinoex P580 binary pump, a Photodiode Array Detector Dionex PDA-100, a Jasco OR-1590 chiral detector and a polarimeter, using a Daicel ChiralPak IA column (4.6×250 mm, 5 mm) under isocratic elution conditions (70% B) employing EtOH+1% TFA (eluent A) and hexane (eluent B), run time 20 min; flow rate 0.8 ml/min, detection at 210 nm.

LC-9: Analytical chiral HPLC performed on a HPLC instrument, equipped with a Dinoex P580 binary pump, a Photodiode Array Detector Dionex PDA-100 and a Jasco OR-1590 chiral detector and a polarimeter, using a Daicel ChiralPak IA column (4.6×250 mm, 5 mm) under isocratic elution conditions (80% B) employing EtOH+1% TFA (eluent A) and hexane (eluent B), run time 20 min; flow rate 0.8 ml/min, detection at 210 nm.

Optical rotation of chiral compounds are measured on a Jasco P-1030 polarimeter in ethanolic solution at 20° C.

$^1$H NMR spectra are recorded on a Varian Mercury 300VX FT-NMR spectrometer. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm.

Intermediate 1.1:

9-Ethoxycarbonylmethyl-2,3,4,9-tetrahydro-1H-carbazole-3-carboxylic acid

Method A a) 2,3,4,9-Tetrahydro-1H-carbazole-3-carboxylic acid

A mixture of 4-oxo-cyclohexanecarboxylic acid (4.05 g, 28.5 mmol) and phenylhydrazine hydrochloride (4.12 g, 28.5 mmol) in EtOH (200 ml) is stirred at reflux for 3 h. Then, the solvent is evaporated and the residue is dissolved in boiling toluene. Precipitating ammonium chloride is filtered off and the clear filtrate is cooled to rt. The resulting precipitate is filtered and tried under high vacuum to give pure subtitle compound as a white solid (5.16 g) in 84% yield. $t_R$ (LC-3) 2.21 min; ESI-MS (positive ion): m/z 216.30 [M+H]$^+$(calcd 215.09 for $C_{13}H_{13}NO_2$). $^1$H-NMR (CDCl$_3$): 2.01 (m, 1H); 2.28 (m, 1H); 2.83 (m, 4H); 3.04 (dd, J=14.8 Hz, 4.7 Hz, 1H); 7.02 (m, 2H); 7.19 (d, J=7.2 Hz, 1H); 7.38 (d, J=7.0 Hz, 1H); 7.63 (s br, 1H).

4-Oxo-cyclohexanecarboxylic acid

Following the method described by D. Wustrow et al. (*J. Med. Chem.* 1998, 41, 760-771), subtitle compound is obtained from ethyl 4-oxo-cyclohexanecarboxylate as a white solid in 74% yield. $^1$H-NMR (CDCl$_3$): 1.72 (m, 2H); 2.02 (m, 2H); 2.17 (m, 2H); 2.32 (m, 2H); 2.64 (m, 1H); 12.2 (s, 1H).

b) 9-Ethoxycarbonylmethyl-2,3,4,9-tetrahydro-1H-carbazole-3-carboxylic acid

To a stirred solution of 2,3,4,9-tetrahydro-1H-carbazole-3-carboxylic acid (0.40 g, 1.86 mmol) in dry DMF (4 ml) is added NaH (0.16 g, 4.1 mmol, 60% in mineral oil) in one portion. After gas evolution has ceased, the reaction mixture is kept stirring at rt for 1 h. Then, ethyl bromoacetate (0.21 ml, 1.9 mmol) is added and stirring is continued overnight. Saturated KH$_2$PO$_4$ solution is added and the mixture is extracted with dichloromethane. The organic layers are combined and washed with H$_2$O and brine, dried over Na$_2$SO$_4$, filtered and concentrated. The residue is purified by flash chromatography on silica gel (hexane/EtOAc 3:1) to afford pure title compound as an off-white solid (0.34 mg) in 61% yield. $t_R$ (LC-3) 2.05 min; ESI-MS (positive ion): m/z 324.15 [M+Na]$^+$ (calcd 301.13 for $C_{17}H_{19}NO_4$). $^1$H-NMR (DMSO-d$_6$): 1.13 (t, J=7.0 Hz, 3H); 1.79 (m, 11-1); 2.14 (m, 1H); 2.64

(m, 4H); 2.86 (dd, J=14.3 Hz, 4.8 Hz, 1H); 4.05 (q, J=7.0 Hz, 2H); 4.88 (s, 2H); 6.90 (dd, J=7.6 Hz, 7.0 Hz, 1H); 6.97 (dd, J=7.6 Hz, 7.0 Hz, 1H); 7.23 (d, J=8.1 Hz, 1H); 7.3 (d, J=6.8 Hz, 1H); 12.08 (s br, 1H).

Method B

A mixture of ethyl (N-phenyl-hydrazino)-acetate hydrochloric acid salt (2.3 g, 10 mmol) and 4-oxo-cyclohexanecarboxylic acid (1.42 g, 10 mmol) in glacial AcOH (20 ml) is stirred at 70° C. for 1 h. The suspension is allowed to cool to rt, poured onto $H_2O$ and stirred for 1 h. The resulting precipitate is filtered, washed with $H_2O$ and dried under high vacuum to give pure 9-ethoxycarbonylmethyl-2,3,4,9-tetrahydro-1H-carbazole-3-carboxylic acid as a white solid (2.85 g) in 93% yield.

Intermediate 1.2:

9-Ethoxycarbonylmethyl-6-fluoro-2,3,4,9-tetrahydro-1H-carbazole-3-carboxylic acid Intermediate 1.2 is prepared analogous to the procedures described for Intermediate 1.1, using (4-fluoro-phenyl)-hydrazine in place of phenylhydrazine (Method A), or ethyl [N-(4-fluoro-phenyl)-hydrazino]-acetate hydrochloric acid salt in place of ethyl (N-phenyl-hydrazino)-acetate hydrochloric acid salt (Method B).

Racemic 9-ethoxycarbonylmethyl-6-fluoro-2,3,4,9-tetrahydro-1H-carbazole-3-carboxylic acid is resolved into enantiomerically pure Intermediate 1.2.1 and 1.2.2, respectively, by applying chiral crystallization techniques by means of a chiral base forming the respective diastereomeric salts.

Intermediate 1.2.1:

(+)-9-Ethoxycarbonylmethyl-6-fluoro-2,3,4,9-tetrahydro-1H-carbazole-3-carboxylic acid Racemic 9-ethoxycarbonylmethyl-6-fluoro-2,3,4,9-tetrahydro-1H-carbazole-3-carboxylic acid (15.0 g, 47.0 mmol) in EtOAc (250 ml) is heated to reflux and treated with S(−)-α-methylbenzylamine (2.99 ml, 23.5 mmol). The clear solution is cooled to rt and the crystals formed are collected by filtration. Recrystallization is repeated four times from EtOAc (2×250 ml, 200 ml and 175 ml). The final crystal fraction is dissolved in EtOAc, extracted with 1N HCl, and washed with water. The organic layer is dried over $Na_2SO_4$ and the solvent evaporated to deliver title compound as a beige crystalline solid with an enantiomeric excess (ee)>96%. $t_R$ (LC-7) 23.65 min; $a_D$=+ 33.5232°, +/−0.0215° (20° C. in ethanol).

Intermediate 1.2.2:

(−)-9-Ethoxycarbonylmethyl-6-fluoro-2,3,4,9-tetrahydro-1H-carbazole-3-carboxylic acid The title compound is prepared analogous to the crystallization procedure described for Intermediate 1.2.1, using R(+)-α-methylbenzylamine, with ee>96%: $t_R$ (LC-7) 21.33 min.

Intermediate 1.3:

9-Ethoxycarbonylmethyl-8-chloro-2,3,4,9-tetrahydro-1H-carbazole-3-carboxylic acid Intermediate 1.3 can be prepared analogous to the procedures described for Intermediate 1.1, using (2-chloro-phenyl)-hydrazine in place of phenylhydrazine (Method A), or ethyl [N-(2-chloro-phenyl)-hydrazino]-acetate hydrochloric acid salt in place of ethyl (N-phenyl-hydrazino)-acetate hydrochloric acid salt (Method B), or with Method C (described below).

Method C a) 8-Chloro-2,3,4,9-tetrahydro-1H-carbazole-3-carboxylic acid

A mixture of 4-oxo-cyclohexanecarboxylic acid (3.1 g, 21.7 mmol) and 2-chlorophenylhydrazine hydrochloride (4.0 g, 21.7 mmol) in glacial acetic acid (740 ml) is stirred at reflux for 3 h. The solvent is evaporated and water is added to the residue. The resulting precipitate is filtered off and dried under high vacuum to give the subtitle compound as a brownish solid (4.5 g) in 83% yield. $t_R$ (LC-5) 0.88 min; ESI-MS (positive ion): m/z 250.14 [M+H]$^+$ (calcd 249.70 for $C_{13}H_{12}NO_2Cl$). $^1$H-NMR (DMSO-$d_6$): 1.75 (m, 1H); 2.14 (m, 1H); 2.62 (m, 5H); 6.90 (t, J=7.9 Hz, 1H); 7.02 (d, J=7.3 Hz, 1H); 7.30 (d, J=7.6 Hz, 1H); 7.92 (br s, 1H); 10.9 (br s, 1H).

b) 8-Chloro-2,3,4,9-tetrahydro-1H-carbazole-3-carboxylic acid benzyl ester

A stirred mixture of crude 8-chloro-2,3,4,9-tetrahydro-1H-carbazole-3-carboxylic acid (4.45 g, 17.8 mmol) and cesium carbonate (2.90 g, 8.92 mmol) in ethanol (150 ml) and water (25 ml) is refluxed until a clear solution is obtained (15 min). Then the solvents are evaporated and the dried residue is dissolved in dry DMF. This solution is treated with benzylbromide (2.27 ml, 18.7 mmol) and stirred at 45° C. for 15 min. The resulting precipitate is filtered off and the filtrate is concentrated. The residue is purified by flash chromatography on silica gel (heptane/EtOAc 3:1) to deliver pure title compound as a yellowish solid (4.2 g) in 69% yield. $t_R$ (LC-5) 1.09 min; ESI-MS (positive ion): m/z 340.19 [M+H]$^+$ (calcd 339.82 for $C_{20}H_{18}NO_2Cl$). $^1$H-NMR (DMSO-$d_6$): 1.90 (m, 1H); 2.19 (m, 1H); 2.86 (m, 5H); 5.13 (s, 2H); 6.91 (t, J=7.6 Hz, 1H); 7.04 (d, J=7.6 Hz, 1H); 7.32 (m, 6H); 11.0 (br s, 1H).

c) 8-Chloro-9-ethoxycarbonylmethyl-2,3,4,9-tetrahydro-1H-carbazole-3-carboxylic acid benzyl ester Cesium carbonate (6.32 g, 19.2 mmol) and ethyl bromoacetate (1.16 ml, 10.2 mmol) are added to a stirred solution of 8-chloro-2,3,4,9-tetrahydro-1H-carbazole-3-carboxylic acid benzyl ester (2.17 g, 6.4 mmol) in dry DMF (20 ml). The reaction mixture is stirred at 60° C. for 3 h. The precipitate is filtered off and rinsed thoroughly with acetone. The filtrate is concentrated and the residue is purified by flash chromatography on silica gel (heptane/EtOAc 4:1) to afford pure title compound as a yellow solid (2.54 mg) in 93% yield. $t_R$ (LC-5) 1.14 min; ESI-MS (positive ion): m/z 426.16 [M+H]$^+$ (calcd 425.91 for $C_{24}H_{24}NO_4Cl$). $^1$H-NMR (CDCl$_3$): 1.25 (t, J=7.0 Hz, 3H); 2.07 (m, 1H); 2.37 (m, 1H); 2.69 (m, 2H); 2.89 (m, 2H); 3.07 (dd, J=14.4, 4.4 Hz, 1H); 4.22 (q, J=7.3 Hz, 2H); 5.07 (d, J=18.2 Hz, 1H); 5.18 (s, 2H); 5.19 (d, J=18.5 Hz, 1H); 6.97 (t, J=7.9 Hz, 1H); 7.08 (dd, J=7.6, 0.9 Hz, 1H); 7.34 (m, 6H).

d) 9-Ethoxycarbonylmethyl-8-chloro-2,3,4,9-tetrahydro-1H-carbazole-3-carboxylic acid A mixture of 8-chloro-9-ethoxycarbonylmethyl-2,3,4,9-tetrahydro-1H-carbazole-3-carboxylic acid benzyl ester (2.5 g, 5.9 mmol) and 10% palladium on activated charcoal (480 mg) in ethanol (200 ml) is stirred under a hydrogen atmosphere for 1 h. The catalyst is filtered off and washed with ethanol. The filtrate is concentrated to dryness to deliver Intermediate 1.3. $t_R$ (LC-5) 0.96 min; ESI-MS (positive ion): m/z 336.23 [M+H]$^+$ (calcd 335.79 for $C_{17}H_{18}NO_4Cl$). $^1$H-NMR (DMSO-d$_6$): 1.18 (t, J=7.0 Hz, 3H); 1.85 (m, 1H); 2.19 (m, 1H); 2.66 (m, 4H); 2.90 (m, 1H); 4.14 (q, J=7.0 Hz, 2H); 5.17 (s, 2H); 6.96 (t, J=7.6 Hz, 1H); 7.04 (d, J=7.3 Hz, 1H); 7.38 (d, J=7.6 Hz, 1H); 12.3 (br s, 1H).

Intermediate 2.1:

9-Ethoxycarbonylmethyl-3-methyl-2,3,4,9-tetrahydro-1H-carbazole-3-carboxylic acid Intermediate 2.1 is prepared analogous to the procedures described for Intermediate 1.1, using 1-methyl-4-oxo-cyclohexanecarboxylic acid in place of 4-oxo-cyclohexanecarboxylic acid.

1-Methyl-4-oxo-cyclohexanecarboxylic acid

Applying reported methods (e.g. M. Rubin, H. Wishinsky, *J. Amer. Chem. Soc.* 1946, 68, 338-340; N. B. Chapman, S. Sotheeswaran, K. J. Toyne, *J. Org. Chem.* 1970, 35, 917-923; H. A. Bruson, T. W. Riener, *J. Amer. Chem. Soc.* 1942, 64, 2850-2858) provided subtitle compound as beige waxy solid.

$^1$H-NMR (CDCl$_3$): 1.38 (s, 3H); 1.73 (m, 2H); 2.43 (m, 6H).

Intermediate 2.2:

9-Ethoxycarbonylmethyl-6-fluoro-3-methyl-2,3,4,9-tetrahydro-1H-carbazole-3-carboxylic acid Intermediate 2.2 is prepared analogous to the procedures described for Intermediate 1.2, using 1-methyl-4-oxo-cyclohexanecarboxylic acid in place of and 4-oxo-cyclohexanecarboxylic acid.

Intermediate 3.1:

9-Ethoxycarbonylmethyl-3-ethyl-2,3,4,9-tetrahydro-1H-carbazole-3-carboxylic acid Intermediate 3.1 is prepared analogous to the procedures described for Intermediate 1.1, using 1-ethyl-4-oxo-cyclohexanecarboxylic acid in place of 4-oxo-cyclohexanecarboxylic acid.

1-Ethyl-4-oxo-cyclohexanecarboxylic acid

Applying reported methods (e.g. M. Rubin, H. Wishinsky, *J. Amer. Chem. Soc.* 1946, 68, 338-340; N. B. Chapman, S. Sotheeswaran, K. J. Toyne, *J. Org. Chem.* 1970, 35, 917-923; H. A. Bruson, T. W. Riener, *J. Amer. Chem. Soc.* 1942, 64, 2850-2858) provided subtitle compound as viscous oil.

$^1$H-NMR (CDCl$_3$): 0.95 (t, J=7.2 Hz, 3H); 1.70 (m, 4H); 2.43 (m, 6H).

Intermediate 3.2:

9-Ethoxycarbonylmethyl-3-ethyl-6-fluoro-2,3,4,9-tetrahydro-1H-carbazole-3-carboxylic acid Intermediate 3.2 is prepared analogous to the procedures described for Intermediate 1.2, using 1-ethyl-4-oxo-cyclohexanecarboxylic acid in place of 4-oxo-cyclohexanecarboxylic acid.

Intermediate 4.1:

9-Ethoxycarbonylmethyl-3-propyl-2,3,4,9-tetrahydro-1H-carbazole-3-carboxylic acid Intermediate 4.1 is prepared analogous to the procedures described for Intermediate 1.1, using 4-oxo-1-propyl-cyclohexanecarboxylic acid in place of 4-oxo-cyclohexanecarboxylic acid.

4-Oxo-1-propyl-cyclohexanecarboxylic acid

Applying reported methods (e.g. M. Rubin, H. Wishinsky, *J. Amer. Chem. Soc.* 1946, 68, 338-340; N. B. Chapman, S. Sotheeswaran, K. J. Toyne, *J. Org. Chem.* 1970, 35, 917-923; H. A. Bruson, T. W. Riener, *J. Amer. Chem. Soc.* 1942, 64, 2850-2858) provided subtitle compound as viscous oil.

$^1$H-NMR (CDCl$_3$): 0.93 (t, J=7.0 Hz, 3H); 1.35 (m, 2H); 1.67 (m, 4H); 2.43 (m, 6H).

Intermediate 4.2:

9-Ethoxycarbonylmethyl-6-fluoro-3-propyl-2,3,4,9-tetrahydro-1H-carbazole-3-carboxylic acid Intermediate 4.2 is prepared analogous to the procedures described for Intermediate 1.2, using 4-oxo-1-propyl-cyclohexanecarboxylic acid in place of 4-oxo-cyclohexanecarboxylic acid.

Intermediate 5.1

3-cyano-2,3,4,9-tetrahydro-1H-carbazole

A mixture of 4-cyano-cyclohexanone (0.48 g, 3.9 mmol) and phenylhydrazine hydrochloride (0.42 g, 3.9 mmol) in glacial acetic acid (5 ml) is stirred at reflux for 1 h. The solvent is evaporated and the residue chromatographed on silica gel (heptane/EtOAc 2:1) to deliver the title compound as a brownish solid (158 mg) in 50% yield. $t_R$ (LC-5) 0.91 min; ESI-MS (positive ion): m/z 197.10 [M+H]$^+$ (calcd 196.25 for $C_{13}H_{12}N_2$). $^1$H-NMR (CDCl$_3$): 2.25 (m, 2H); 2.96 (m, 5H); 7.14 (m, 2H); 7.30 (d, J=7.7 Hz, 1H); 7.45 (d, J=7.1 Hz, 1H); 7.79 (br s, 1H).

4-Cyano-cyclohexanone

Applying reported methods (e.g. M. Rubin, H. Wishinsky, *J. Amer. Chem. Soc.* 1946, 68, 338-340; N. B. Chapman, S. Sotheeswaran, K. J. Toyne, *J. Org. Chem.* 1970, 35, 917-923; H. A. Bruson, T. W. Riener, *J. Amer. Chem. Soc.* 1942, 64, 2850-2858) provided subtitle compound as slightly yellow oil.

Ethyl (N-phenyl-hydrazino)-acetate hydrochloric acid salt a) Ethyl phenylamino-acetate According to Kotake et al. (*Chem. Pharm. Bull.* 1995, 43, 829-841), a stirred solution of aniline (15.3 g, 0.16 mol) and DIEA (56 ml, 0.33 mol) in acetonitrile (120 ml) is heated to 60° C. and ethyl bromoacetate (18.2 ml, 0.16 mmol) is added dropwise within 2 h. The reaction mixture is kept stirring at this temperature for another 3 h and is then evaporated to dryness. Water is added to the residue, the solid is filtered and thoroughly rinsed with H$_2$O. Crystallization from toluene provided pure subtitle compound as beige crystals (25.5 g) in 87% yield. $t_R$ (LC-3) 2.33 min; ESI-MS (positive ion): m/z 180.27 [M+H]$^+$ (calcd 179.22 for $C_{10}H_{13}NO_2$). $^1$H-NMR (CDCl$_3$): 1.29 (t, J=7.0 Hz, 3H); 3.90 (s, 2H); 4.25 (m, 3H); 6.61 (d, J=8.2 Hz, 2H); 6.75 (t, J=7.1 Hz, 1H); 7.21 (m, 2H).

b) Ethyl N-nitroso-phenylamino-acetate

A solution of NaNO$_2$ (9.5 g, 0.14 mol) in H$_2$O (27 ml) is added to an ice-cold stirred solution of ethyl phenylamino-acetate (25 g, 0.14 mol) in conc. HCl (20 ml) and H$_2$O (27 ml) within 2 h. The reaction mixture is kept stirring for 1 h and then extracted twice with CH$_2$Cl$_2$. The combined organic layers are washed with H$_2$O and brine, dried over Na$_2$SO$_4$ and filtered. The solvent is evaporated and the crude subtitle compound thus obtained as orange oil is used without further purification. t$_R$ (LC-4) 1.02 min.

c) Ethyl (N-phenyl-hydrazino)-acetate hydrochloric acid salt

According to Arcari et al. (*Farmaco* 1992, 47, 405-425), crude ethyl N-nitroso-phenylamino-acetate (0.14 mol) is dissolved in glacial AcOH (50 ml) and added to an ice-cold stirred suspension of zinc (32 g, 0.49 mol) in H$_2$O (50 ml) within 1 h. The reaction mixture is kept stirring at rt for 2 h, then the resulting precipitate is filtered and thoroughly washed with MeOH. The filtrate is acidified to pH 1 by the addition of conc. HCl and washed with TBME, then basified to pH 10 by the addition of aqueous NH$_4$OH and extracted with CH$_2$Cl$_2$. The combined organic layers are dried over Na$_2$SO$_4$ and evaporated to give desired hydrazine as an oil. The compound is converted in its hydrochloride salt by treatment of the free hydrazine in diethyl ether with HCl (2N in Et$_2$O) to give title compound (20 g) in 63% yield (over two steps). t$_R$ (LC-3) 2.33 min; ESI-MS (positive ion): m/z 180.27 [M+H]$^+$ (calcd 179.22 for $C_{10}H_{13}NO_2$). $^1$H-NMR (DMSO-d$_6$): 1.15 (t, J=7.0 Hz, 3H); 3.59 (br s, 1H); 4.11 (q, J=7.0 Hz, 2H); 4.65 (s, 2H); 7.00 (m, 1H); 7.07 (m, 2H); 7.33 (m, 2H); 10.6 (br s, 1H).

Preparation of Amines of Formula HNR$^7$R$^8$:

The following amines are prepared according to the references listed below.

N-Phenyl-phenethylamine a) M. Beller, C. Breindl, T. H. Riermeier, M. Eichberger, H. Trauthwein, *Angew. Chme. Int. Ed.* 1998, 37, 3389-3391; b) F. Y. Kwang, A. Klapars, S. L. Buchwald, *Org. Lett.* 2002, 4, 581-584; c) L. Guy, C. Schaeffer, *Heterocycles* 1998, 48, 171-174.

5,6,11,12-Tetrahydro-dibenzo[b,f]azocine

A. M. Monro, R. M. Quinton, T. I. Wrigley, *J. Med. Chem.* 1963, 6, 255-261.

6,11-Dihydro-5H-dibenzo[b,e]azepine a) E. J. Warawa, B. M. Migler, C. J. Ohnmacht, A. L. Needles, G. C. Gatos, F. M. McLaren, C. L. Nelson, K. M. Kirkland, *J. Med. Chem.* 2001, 44, 372-389; b) L. H. Werner, S. Ricca, E. Mohacsi, A. Rossi, V. P. Arys, *J. Med. Chem.* 1965, 8, 74-80.

5,11-Dihydrodibenzo[b,e][1,4]oxazepine

B. J. Margolis, J. J. Swidorski, B. N. Rogers, *J. Org. Chem.* 2003, 68, 644-647.

Diphenethylamine

W. S. Bryant, I. A. Guzei, A. L. Rheingold, J. S. Merola, H. W. Gibson, *J. Org. Chem.* 1998, 63, 7634-7639.

[2-(4-Fluoro-phenyl)-ethyl]-phenyl-amine

J. D. Albright, V. G. DeVries, E. E. Largis, T. G. Miner, M. F. Reich, S. A. Schaffer, R. G. Shepherd, J. Upeslacis, *J. Med. Chem.* 1983, 26, 1378-1393.

[2-(4-chloro-phenyl)-ethyl]-phenyl-amine, phenyl-(3-phenyl-propyl)-amine, phenyl-(2-thiophen-3-yl-ethyl)-amine and (2,2-diphenyl-ethyl)-phenyl-amine are prepared applying the same procedure.

Example A-01

(±)-(3-Dibenzylcarbamoyl-1,2,3,4-tetrahydro-carbazol-9-yl)-acetic acid a): Ethyl (±)-(3-dibenzylcarbamoyl-1,2,3,4-tetrahydro-carbazol-9-yl)-acetate A solution of Intermediate 1.1 (30 mg, 0.1 mmol), N,N,N',N'-tetramethyl-O-(7-azabenzotriazole-1-yl)-uronium-hexafluorophosphate (38 mg, 0.1 mmol) and DIEA (51 µl, 0.3 mmol) in THF/DMF 4:1 (1 ml) is stirred at rt for 10 min and then is treated with dibenzylamine (20 mg, 0.1 mmol). After further stirring overnight at rt, the reaction mixture is diluted with H$_2$O (3 ml) and extracted three times with diethyl ether. The combined organic layers are evaporated and the obtained crude subtitle compound is used for further synthesis without purification. t$_R$ (LC-3) 3.03 min; MS (positive ion) m/z 481.29 [M+H]$^+$ (calcd 480.62 for $C_{31}H_{32}N_2O_3$).

b) (±)-(3-Dibenzylcarbamoyl-1,2,3,4-tetrahydro-carbazol-9-yl)-acetic acid

A stirred solution of crude ethyl (±)-(3-dibenzylcarbamoyl-1,2,3,4-tetrahydro-carbazol-9-yl)-acetate (0.1 mmol) in THF (1 ml) is treated with 0.2 N aqueous NaOH (0.5 ml, 0.1 mmol) added at rt for 15 min. Then, the reaction mixture is extracted twice with diethyl ether (2 ml), acidified to pH 1 by addition of 1M HCl and extracted with CH$_2$Cl$_2$. The combined organic layers are dried (Na$_2$SO$_4$), filtered and evaporated. The resulting solid is recrystallized from diethyl ether to yield title compound as a pale yellow solid. t$_R$ (LC-2) 2.74 min; MS (positive ion) m/z 453.26 [M+H]$^+$ (calcd 452.55 for $C_{29}H_{28}N_2O_3$).

$^1$H-NMR (DMSO-d$_6$): 1.96 (m, 2H); 2.68 (m, 4H); 2.95 (m, 1H); 4.05 (m, 2H); 4.66 (m, 2H); 4.81 (s, 2H); 6.98 (m, 2H); 7.26 (m, 12H); 12.8 (s, 1H).

Example A-02

{3-[(4-Chloro-phenyl)-methyl-carbamoyl]-1,2,3,4-tetrahydro-carbazol-9-yl}-acetic acid a) Ethyl (±)-{3-[(4-chloro-phenyl)-methyl-carbamoyl]-1,2,3,4-tetrahydro-carbazol-9-yl}-acetate and its enantiomers At −10° C., bis(trichloromethyl)carbonate (66 mg, 0.22 mmol) and collidine (0.29 ml, 2.2 mmol) are added to a stirred solution of Intermediate 1.1 (0.20 g, 0.66 mmol) in dry THF (3 ml). The resulting suspension is stirred at this temperature for 1 min and then treated with 4-chloro-N-methylanilin (94 mg, 0.66 mmol). After stirring for 30 min the reaction is complete, the mixture poured onto 1M HCl (50 ml) and extracted three times with diethyl ether. The combined organic layers are dried over $Na_2SO_4$ and evaporated to dryness to leave the crude subtitle compound (0.20 g) in 71% yield as a pale yellow glassy solid. This material is used for further synthesis without purification. $t_R$ (LC-1) 1.24 min; MS (positive ion) m/z 446.96 [M+Na]$^+$ (calcd 424.92 for $C_{24}H_{25}N_2O_3Cl$). Retention times of the two enantiomers are respectively 10.1 min and 13.1 min (LC-6, 55% B), the more polar enantiomer displaying a rotation of the plane of the polarized light in a clockwise direction, the less polar enantiomer displaying a rotation in an anticlockwise direction, respectively, resulting a positive (+) and a negative (−) signal of the polarimetric plot, as co-monitored with an interfaced polarimeter.

Resolution into the enantiomers is carried out on a preparative chiral HPLC column (Chiralcel OD, 20×250 mm, 10 μm) under isocratic elution conditions (EtOH/hexane 45:55), runtime 30 min; flow rate 10 ml/min, detection at 220 nm. The (+) enantiomer of ethyl-{3-[(4-chloro-phenyl)-methyl-carbamoyl]-1,2,3,4-tetrahydro-carbazol-9-yl}-acetate is eluting after 15.0 min, the (−) enantiomer after 18.5 min. Both enantiomers are obtained in >99% ee, as verified with LC-6 (55% B).

b) (±)-{3-[(4-Chloro-phenyl)-methyl-carbamoyl]-1,2,3,4-tetrahydro-carbazol-9-yl}-acetic acid The title compound is obtained using conditions for the hydrolysis of crude ethyl (±)-{3-[(4-chloro-phenyl)-methyl-carbamoyl]-1,2,3,4-tetrahydro-carbazol-9-yl}-acetate analogous to Example 1: $t_R$ (LC-1) 1.09 min; ESI-MS (positive ion): m/z 396.92 [M]$^+$ (calcd 396.12 for $C_{22}H_{21}N_2O_3Cl$). $^1$H-NMR (CDCl$_3$): 2.05 (m, 2H); 2.42 (m, 1H); 2.70 (m, 3H); 2.92 (m, 1H); 3.28 (s, 3H); 4.65 (s, 2H); 7.11 (m, 5H); 7.37 (m, 3H). Retention times of the two enantiomers are respectively 12.4 min and 15.5 min (LC-6, 75% B), the more polar enantiomer displaying a rotation of the plane of the polarized light in a clockwise direction, the less polar enantiomer displaying a rotation in an anticlockwise direction, respectively, resulting a positive (+) and a negative (−) signal of the polarimetric plot, as co-monitored with an interfaced polarimeter.

b1) (+)-{3-[(4-Chloro-phenyl)-methyl-carbamoyl]-1,2,3,4-tetrahydro-carbazol-9-yl}-acetic acid The title compound is obtained using conditions for the hydrolysis of ethyl (+)-{3-[(4-chloro-phenyl)-methyl-carbamoyl]-1,2,3,4-tetrahydro-carbazol-9-yl}-acetate analogous to Example 1: $t_R$ (LC-1) 1.09 min; ESI-MS (positive ion): m/z 396.92 [M]$^+$; $t_R$ (LC-6, 75% B) 12.4 min, positive signal of the polarimetric plot; ee>99%.

b2) (−)-{3-[(4-Chloro-phenyl)-methyl-carbamoyl]-1,2,3,4-tetrahydro-carbazol-9-yl}-acetic acid The title compound is obtained using conditions for the hydrolysis of ethyl (−)-{3-[(4-chloro-phenyl)-methyl-carbamoyl]-1,2,3,4-tetrahydro-carbazol-9-yl}-acetate analogous to Example 1: $t_R$ (LC-1) 1.09 min; ESI-MS (positive ion): m/z 396.92 [M]$^+$; $t_R$ (LC-6, 75% B) 15.5 min, negative signal of the polarimetric plot; ee>99%.

TABLE 1

Examples A-03 to A-61 are prepared using procedures analogous to those described for Example A-01 or A-02.

| Ex. | Compound Name | Formula MW | $t_R$ (Method) | ESI m/z |
|---|---|---|---|---|
| A-03 | (±)-[3-(3,4-Dihydro-1H-isoquinoline-2-carbonyl)-1,2,3,4-tetrahydro-carbazol-9-yl]-acetic acid | C24H24N2O3 388.46 | 2.28 (LC-3) | 389.18 |
| A-04 | (±)-(3-Phenylcarbamoyl-1,2,3,4-tetrahydro-carbazol-9-yl)-acetic acid | C21H20N2O3 348.401 | 2.08 (LC-3) | 371.15 [M+Na]$^+$ |
| A-05 | (±)-{3-[Benzyl-((S)-1-phenyl-ethyl)-carbamoyl]-1,2,3,4-tetrahydro-carbazol-9-yl}-acetic acid | C30H30N2O3 466.579 | 2.55 (LC-3) | 467.21 |
| A-06 | (±)-{3-[Benzyl-((R)-1-phenyl-ethyl)-carbamoyl]-1,2,3,4-tetrahydro-carbazol-9-yl}-acetic acid | C30H30N2O3 466.579 | 2.53 (LC-3) | 467.21 |
| A-07 | (±)-[3-(Methyl-phenethyl-carbamoyl)-1,2,3,4-tetrahydro-carbazol-9-yl]-acetic acid | C24H26N2O3 390.481 | 2.22 (LC-3) | 391.21 |
| A-08 | (±)-[3-(Benzyl-phenethyl-carbamoyl)-1,2,3,4-tetrahydro-carbazol-9-yl]-acetic acid | C30H30N2O3 466.579 | 2.48 (LC-3) | 467.28 |
| A-09 | (±)-(3-Diphenethylcarbamoyl-1,2,3,4-tetrahydro-carbazol-9-yl)-acetic acid | C31H32N2O3 480.606 | 2.56 (LC-3) | 481.23 |
| A-10 | (±)-[3-(6,11-Dihydro-dibenzo[b,e]azepine-5-carbonyl)-1,2,3,4-tetrahydro-carbazol-9-yl]-acetic acid | C29H26N2O3 450.536 | 1.14 (LC-4) | 450.98 |
| A-11 | (±)-{3-[Phenyl-(3-phenyl-propyl)-carbamoyl]-1,2,3,4-tetrahydro-carbazol-9-yl}-acetic acid | C30H30N2O3 466.579 | 1.19 (LC-4) | 467.04 |
| A-12 | (±)-[3-(Phenyl-thiophen-3-ylmethyl-carbamoyl)-1,2,3,4-tetrahydro-carbazol-9-yl]-acetic acid | C26H24N2O3S 444.554 | 1.13 (LC-4) | 444.96 |
| A-13 | (±)-[3-(Isopropyl-phenyl-carbamoyl)-1,2,3,4-tetrahydro-carbazol-9-yl]-acetic acid | C24H26N2O3 390.481 | 1.11 (LC-4) | 391.04 |
| A-14 | (±)-[3-(11,12-Dihydro-6H-dibenzo[b,f]azocine-5-carbonyl)-1,2,3,4-tetrahydro-carbazol-9-yl]-acetic acid | C30H28N2O3 464.563 | 2.46 (LC-3) | 465.17 |
| A-15 | (±)-(3-(Butyl-phenyl-carbamoyl)-1,2,3,4-tetrahydro-carbazol-9-yl)-acetic acid | C25H28N2O3 404.508 | 2.47 (LC-3) | 405.23 |
| A-16 | (±)-[3-(3,4-Dihydro-2H-quinoline-1-carbonyl)-1,2,3,4-tetrahydro-carbazol-9-yl]-acetic acid | C24H24N2O3 388.466 | 2.22 (LC-0) | 389.31 |
| A-17 | (±)-[3-(Benzyl-phenyl-carbamoyl)-1,2,3,4-tetrahydro-carbazol-9-yl]-acetic acid | C28H26N2O3 438.525 | 2.32 (LC-3) | 439.26 |
| A-18 | (±)-[3-(2-Methoxy-phenylcarbamoyl)-1,2,3,4-tetrahydro-carbazol-9-yl]-acetic acid | C22H22N2O4 378.427 | 2.12 (LC-3) | 379.05 |
| A-19 | (±)-[3-(4-Methoxy-biphenyl-3-ylcarbamoyl)-1,2,3,4-tetrahydro-carbazol-9-yl]-acetic acid | C28H26N2O4 454.524 | 2.41 (LC-3) | 455.37 |

TABLE 1-continued

Examples A-03 to A-61 are prepared using procedures analogous to those described for Example A-01 or A-02.

| Ex. | Compound Name | Formula MW | LC-MS $t_R$ (Method) | ESI m/z |
|---|---|---|---|---|
| A-20 | (±)-[3-(Ethyl-phenyl-carbamoyl)-1,2,3,4-tetrahydro-carbazol-9-yl]-acetic acid | C23H24N2O3 376.455 | 2.13 (LC-3) | 377.23 |
| A-21 | (±)-[3-(Methyl-phenyl-carbamoyl)-1,2,3,4-tetrahydro-carbazol-9-yl]-acetic acid | C22H22N2O3 362.428 | 2.03 (LC-3) | 363.26 |
| A-22 | (±)-[3-(3-Benzoyl-phenylcarbamoyl)-1,2,3,4-tetrahydro-carbazol-9-yl]-acetic acid | C28H24N2O4 452.509 | 2.28 (LC-3) | 453.21 |
| A-23 | (±)-[3-(5-Chloro-2-methoxy-phenylcarbamoyl)-1,2,3,4-tetrahydro-carbazol-9-yl]-acetic acid | C22H21N2O4Cl 412.872 | 2.33 (LC-3) | 435.30 [M + Na]+ |
| A-24 | (±)-[3-(2-Benzyl-phenylcarbamoyl)-1,2,3,4-tetrahydro-carbazol-9-yl]-acetic acid | C28H26N2O3 438.525 | 2.27 (LC-3) | 439.25 |
| A-25 | (±)-[3-(Dibenzo[b,f]azepine-5-carbonyl)-1,2,3,4-tetrahydro-carbazol-9-yl]-acetic acid | C29H24N2O3 448.521 | 2.29 (LC-3) | 449.28 |
| A-26 | (±)-[3-(6,7-Dimethoxy-3,4-dihydro-1H-isoquinoline-2-carbonyl)-1,2,3,4-tetrahydro-carbazol-9-yl]-acetic acid | C26H28N2O5 448.517 | 1.98 (LC-3) | 449.18 |
| A-27 | (±)-{3-[(4-Fluoro-phenyl)-methyl-carbamoyl]-1,2,3,4-tetrahydro-carbazol-9-yl}-acetic acid | C22H21N2O3F 380.418 | 2.10 (LC-0) | 381.28 |
| A-28 | (±)-[3-(Ethyl-naphthalen-1-yl-carbamoyl)-1,2,3,4-tetrahydro-carbazol-9-yl]-acetic acid | C27H26N2O3 426.514 | 1.08 (LC-4) | 426.98 |
| A-29 | (±)-[3-(Cyclohexyl-phenyl-carbamoyl)-1,2,3,4-tetrahydro-carbazol-9-yl]-acetic acid | C27H30N2O3 430.546 | 1.14 (LC-4) | 430.97 |
| A-30 | (±)-[3-(Phenethyl-phenyl-carbamoyl)-1,2,3,4-tetrahydro-carbazol-9-yl]-acetic acid | C29H28N2O3 452.552 | 1.14 (LC-4) | 453.05 |
| A-31 | (±)-[3-(Methyl-o-tolyl-carbamoyl)-1,2,3,4-tetrahydro-carbazol-9-yl]-acetic acid | C23H24N2O3 376.455 | 1.06 (LC-4) | 376.99 |
| A-32 | (±)-[3-(Allyl-phenyl-carbamoyl)-1,2,3,4-tetrahydro-carbazol-9-yl]-acetic acid | C24H24N2O3 388.466 | 1.09 (LC-4) | 388.96 |
| A-33 | (±)-[3-(7-Trifluoromethyl-3,4-dihydro-2H-quinoline-1-carbonyl)-1,2,3,4-tetrahydro-carbazol-9-yl]-acetic acid | C25H23N2O3F3 456.463 | 1.17 (LC-4) | 457.14 |
| A-34 | (±)-[3-(Benzyl-isopropyl-carbamoyl)-1,2,3,4-tetrahydro-carbazol-9-yl]-acetic acid | C25H28N2O3 404.508 | 1.13 (LC-1) | 405.02 |
| A-35 | (±)-{3-[(3-Chloro-phenyl)-methyl-carbamoyl]-1,2,3,4-tetrahydro-carbazol-9-yl}-acetic acid | C22H21N2O3Cl 396.873 | 1.08 (LC-1) | 396.92 |
| A-36 | (±)-[3-(Benzhydryl-carbamoyl)-1,2,3,4-tetrahydro-carbazol-9-yl]-acetic acid | C28H26N2O3 438.525 | 1.12 (LC-1) | 439.07 |
| A-37 | (±)-{3-[Methyl-(2-trifluoromethyl-phenyl)-carbamoyl]-1,2,3,4-tetrahydro-carbazol-9-yl}-acetic acid | C23H21N2O3F3 430.425 | 1.08 (LC-1) | 430.89 |
| A-38 | (±)-{3-[(3,4-Dichloro-phenyl)-methyl-carbamoyl]-1,2,3,4-tetrahydro-carbazol-9-yl}-acetic acid | C22H20N2O3Cl2 431.318 | 1.14 (LC-1) | 452.77 [M + Na]+ |
| A-39 | (±)-[3-(2,3-Dihydro-indole-1-carbonyl)-1,2,3,4-tetrahydro-carbazol-9-yl]-acetic acid | C23H22N2O3 374.439 | 1.09 (LC-1) | 374.92 |
| A-40 | (±)-{3-[(3-Fluoro-phenyl)-methyl-carbamoyl]-1,2,3,4-tetrahydro-carbazol-9-yl}-acetic acid | C22H21N2O3F 380.418 | 1.03 (LC-1) | 380.94 |
| A-41 | (±)-{3-[Ethyl-(4-trifluoromethoxy-phenyl)-carbamoyl]-1,2,3,4-tetrahydro-carbazol-9-yl}-acetic acid | C24H23N2O4F3 460.451 | 1.16 (LC-1) | 461.02 |
| A-42 | (±)-[3-(Benzhydryl-methyl-carbamoyl)-1,2,3,4-tetrahydro-carbazol-9-yl]-acetic acid | C29H28N2O3 452.552 | 1.18 (LC-1) | 453.05 |
| A-43 | (±)-{3-[Benzyl-(2-cyano-ethyl)-carbamoyl]-1,2,3,4-tetrahydro-carbazol-9-yl}-acetic acid | C25H25N3O3 415.492 | 1.02 (LC-1) | 416.02 |
| A-44 | (±)-{3-[Methyl-(2-pyridin-2-yl-ethyl)-carbamoyl]-1,2,3,4-tetrahydro-carbazol-9-yl}-acetic acid | C23H25N3O3 391.47 | 0.69 (LC-1) | 392.01 |
| A-45 | (±)-{3-[(Benzo[1,3]dioxol-5-ylmethyl)-carbamoyl]-1,2,3,4-tetrahydro-carbazol-9-yl}-acetic acid | C23H22N2O5 406.437 | 0.99 (LC-1) | 406.87 |
| A-46 | (±)-{3-[4-(4-Fluoro-phenyl)-piperazine-1-carbonyl]-1,2,3,4-tetrahydro-carbazol-9-yl}-acetic acid | C25H26N3O3F 435.497 | 1.07 (LC-1) | 436.03 |
| A-47 | (±)-[3-(2-Fluoro-phenylcarbamoyl)-1,2,3,4-tetrahydro-carbazol-9-yl]-acetic acid | C21H19N2O3F 366.391 | 1.04 (LC-4) | 389.06 [M + Na] |
| A-48 | (±)-[3-(3-Fluoro-phenylcarbamoyl)-1,2,3,4-tetrahydro-carbazol-9-yl]-acetic acid | C21H19N2O3F 366.391 | 1.05 (LC-4) | 367.03 |
| A-49 | (±)-[3-(4-Fluoro-phenylcarbamoyl)-1,2,3,4-tetrahydro-carbazol-9-yl]-acetic acid | C21H19N2O3F 366.391 | 1.03 (LC-4) | 367.1 |
| A-50 | (±)-{3-[Benzyl-(3-fluoro-benzyl)-carbamoyl]-1,2,3,4-tetrahydro-carbazol-9-yl}-acetic acid | C29H27N2O3F 470.542 | 1.14 (LC-4) | 471.13 |
| A-51 | (±)-{3-[Benzyl-(4-fluoro-benzyl)- | C29H27N2O3F 470.542 | 1.13 (LC-4) | 469.19 [M − H] |

TABLE 1-continued

Examples A-03 to A-61 are prepared using procedures analogous to those described for Example A-01 or A-02.

| Ex. | Compound Name | Formula MW | t_R (Method) | LC-MS ESI m/z |
|---|---|---|---|---|
| | carbamoyl]-1,2,3,4-tetrahydro-carbazol-9-yl}-acetic acid | | | |
| A-52 | (±)-{3-[Benzyl-(2-trifluoromethyl-benzyl)-carbamoyl]-1,2,3,4-tetrahydro-carbazol-9-yl}-acetic acid | C30H27N2O3F3 520.549 | 1.15 (LC-4) | 521.07 |
| A-53 | (±)-{3-[Benzyl-(3-trifluoromethyl-benzyl)-carbamoyl]-1,2,3,4-tetrahydro-carbazol-9-yl}-acetic acid | C30H27N2O3F3 520.549 | 1.17 (LC-4) | 521.21 |
| A-54 | (±)-{3-[Benzyl-(2,5-difluoro-benzyl)-carbamoyl]-1,2,3,4-tetrahydro-carbazol-9-yl}-acetic acid | C29H26N2O3F2 488.532 | 1.14 (LC-4) | 489.14 |
| A-55 | (±)-{3-[Benzyl-(3,5-difluoro-benzyl)-carbamoyl]-1,2,3,4-tetrahydro-carbazol-9-yl}-acetic acid | C29H26N2O3F2 488.532 | 1.14 (LC-4) | 489.21 |
| A-56 | (±)-{3-[Benzyl-(4-chloro-2-fluoro-benzyl)-carbamoyl]-1,2,3,4-tetrahydro-carbazol-9-yl}-acetic acid | C29H26N2O3ClF 504.987 | 1.16 (LC-4) | 505.14 |
| A-57 | (±)-(3-{Benzyl-[2-(2-fluoro-phenyl)-ethyl]-carbamoyl}-1,2,3,4-tetrahydro-carbazol-9-yl)-acetic acid | C30H29N2O3F 484.569 | 1.14 (LC-4) | 485.19 |
| A-58 | (±)-(3-{Benzyl-[2-(3-fluoro-phenyl)-ethyl]-carbamoyl}-1,2,3,4-tetrahydro-carbazol-9-yl)-acetic acid | C30H29N2O3F 484.569 | 1.14 (LC-4) | 485.19 |
| A-59 | (±)-(3-{Benzyl-[2-(4-fluoro-phenyl)-ethyl]-carbamoyl}-1,2,3,4-tetrahydro-carbazol-9-yl)-acetic acid | C30H29N2O3F 484.569 | 1.14 (LC-4) | 485.19 |
| A-60 | (±)-(3-{Benzyl-[2-(4-chloro-phenyl)-ethyl]-carbamoyl}-1,2,3,4-tetrahydro-carbazol-9-yl)-acetic acid | C30H29N2O3Cl 501.024 | 1.17 (LC-4) | 501.12 |
| A-61 | (±)-(3-{Benzyl-[2-(2,6-dichloro-phenyl)-ethyl]-carbamoyl}-1,2,3,4-tetrahydro-carbazol-9-yl)-acetic acid | C30H28N2O3Cl2 535.469 | 1.19 (LC-4) | 535.13 |

TABLE 2

Examples B-01 to B-71 are prepared using procedures analogous to those described for Example A-01 or A-02.

| Ex. | Compound Name | Formula MW | t_R (Method) | LC-MS ESI m/z |
|---|---|---|---|---|
| B-01 | (±)-[3-Methyl-3-(methyl-phenyl-carbamoyl)-1,2,3,4-tetrahydro-carbazol-9-yl]-acetic acid | C23H24N2O3 376.455 | 0.96 (LC-5) | 377.32 |
| B-02 | (±)-[3-(2,3-Dihydro-indole-1-carbonyl)-3-methyl-1,2,3,4-tetrahydro-carbazol-9-yl]-acetic acid | C24H24N2O3 388.466 | 1.14 (LC-1) | 388.96 |
| B-03 | (±)-[3-(6,11-Dihydro-dibenzo[b,e]azepine-5-carbonyl)-3-methyl-1,2,3,4-tetrahydro-carbazol-9-yl]-acetic acid | C30H28N2O3 464.563 | 1.24 (LC-1) | 465.03 |
| B-04 | (±)-[3-(Benzyl-phenyl-carbamoyl)-3-methyl-1,2,3,4-tetrahydro-carbazol-9-yl]-acetic acid | C29H28N2O3 452.552 | 1.23 (LC-1) | 453.05 |
| B-05 | (±)-{3-Methyl-3-[phenyl-(3-phenyl-propyl)-carbamoyl]-1,2,3,4-tetrahydro-carbazol-9-yl}-acetic acid | C31H32N2O3 480.606 | 1.29 (LC-2) | 481.09 |
| B-06 | (±)-[3-(Benzhydryl-methyl-carbamoyl)-3-methyl-1,2,3,4-tetrahydro-carbazol-9-yl]-acetic acid | C30H30N2O3 466.579 | 1.24 (LC-2) | 488.98 [M+Na]+ |
| B-07 | (±)-[3-Methyl-3-(phenyl-thiophen-3-ylmethyl-carbamoyl)-1,2,3,4-tetrahydro-carbazol-9-yl]-acetic acid | C27H26N2O3S 458.58 | 1.22 (LC-1) | 458.94 |
| B-08 | (±)-[3-(3,4-Dihydro-2H-quinoline-1-carbonyl)-3-methyl-1,2,3,4-tetrahydro-carbazol-9-yl]-acetic acid | C25H26N2O3 402.492 | 1.15 (LC-1) | 402.94 |
| B-09 | (±)-[3-(Cyclohexyl-phenyl-carbamoyl)-3-methyl-1,2,3,4-tetrahydro-carbazol-9-yl]-acetic acid | C28H32N2O3 444.573 | 1.31 (LC-1) | 467.04 [M+Na]+ |
| B-10 | (±)-{3-[(3-Chloro-phenyl)-methyl-carbamoyl]-3-methyl-1,2,3,4-tetrahydro-carbazol-9-yl}-acetic acid | C23H23N2O3Cl 410.9 | 1.15 (LC-1) | 432.91 [M+Na]+ |
| B-11 | (±)-[3-Methyl-3-(phenethyl-phenyl-carbamoyl)-1,2,3,4-tetrahydro-carbazol-9-yl]-acetic acid | C30H30N2O3 466.579 | 1.26 (LC-2) | 466.93 |
| B-12 | (±)-{3-[(4-Fluoro-phenyl)-methyl-carbamoyl]-3-methyl-1,2,3,4-tetrahydro-carbazol-9-yl}-acetic acid | C23H23N2O3F 394.445 | 1.10 (LC-1) | 416.92 [M+Na]+ |
| B-13 | (±)-{3-[(3,4-Dichloro-phenyl)-methyl-carbamoyl]-3-methyl-1,2,3,4-tetrahydro-carbazol-9-yl}-acetic acid | C23H22N2O3Cl2 445.345 | 1.21 (LC-1) | 466.9 [M+Na]+ |
| B-14 | (±)-[3-Methyl-3-(methyl-o-tolyl-carbamoyl)-1,2,3,4-tetrahydro-carbazol-9-yl]-acetic acid | C24H26N2O3 390.481 | 1.13 (LC-1) | 390.97 |

TABLE 2-continued

Examples B-01 to B-71 are prepared using procedures analogous to those described for Example A-01 or A-02.

| Ex. | Compound Name | Formula MW | LC-MS $t_R$ (Method) | ESI m/z |
|---|---|---|---|---|
| B-15 | (±)-[3-(Isopropyl-phenyl-carbamoyl)-3-methyl-1,2,3,4-tetrahydro-carbazol-9-yl]-acetic acid | C25H28N2O3 404.508 | 1.19 (LC-1) | 427.03 [M + Na]+ |
| B-16 | (±)-[3-(Ethyl-naphthalen-1-yl-carbamoyl)-3-methyl-1,2,3,4-tetrahydro-carbazol-9-yl]-acetic acid | C28H28N2O3 440.541 | 1.03 (LC-5) | 441.34 |
| B-17 | (±)-[3-(Allyl-phenyl-carbamoyl)-3-methyl-1,2,3,4-tetrahydro-carbazol-9-yl]-acetic acid | C25H26N2O3 402.492 | 1.00 (LC-5) | 403.34 |
| B-18 | (±)-{3-[Benzyl-((R)-1-phenyl-ethyl)-carbamoyl]-3-methyl-1,2,3,4-tetrahydro-carbazol-9-yl}-acetic acid | C31H32N2O3 480.606 | 1.25 (LC-1) | 503.04 |
| B-19 | (±)-[3-(2-Benzyl-phenylcarbamoyl)-3-methyl-1,2,3,4-tetrahydro-carbazol-9-yl]-acetic acid | C29H28N2O3 452.552 | 1.18 (LC-1) | 453.05 |
| B-20 | (±)-[3-(Benzyl-phenethyl-carbamoyl)-3-methyl-1,2,3,4-tetrahydro-carbazol-9-yl]-acetic acid | C31H32N2O3 480.606 | 1.07 (LC-5) | 481.43 |
| B-21 | (±)-[3-(2,3-Dihydro-indole-1-carbonyl)-3-propyl-1,2,3,4-tetrahydro-carbazol-9-yl]-acetic acid | C26H28N2O3 416.519 | 1.14 (LC-4) | 438.93 |
| B-22 | (±)-[3-(2,3-Dihydro-indole-1-carbonyl)-3-ethyl-1,2,3,4-tetrahydro-carbazol-9-yl]-acetic acid | C25H26N2O3 402.492 | 1.11 (LC-4) | 402.78 |
| B-23 | (±)-(3-Ethyl-3-phenylcarbamoyl-1,2,3,4-tetrahydro-carbazol-9-yl)-acetic acid | C23H24N2O3 376.455 | 1.07 (LC-4) | 377.04 |
| B-24 | (±)-[3-Ethyl-3-(4-fluoro-phenylcarbamoyl)-1,2,3,4-tetrahydro-carbazol-9-yl]-acetic acid | C23H23N2O3F 394.445 | 1.07 (LC-4) | 416.99 [M + Na] |
| B-25 | (±)-(3-Phenylcarbamoyl-3-propyl-1,2,3,4-tetrahydro-carbazol-9-yl)-acetic acid | C24H26N2O3 390.481 | 1.08 (LC-4) | 413.04 [M + Na] |
| B-26 | (±)-(3-Methyl-3-phenylcarbamoyl-1,2,3,4-tetrahydro-carbazol-9-yl)-acetic acid | C22H22N2O3 362.428 | 1.05 (LC-4) | 361.11 [M − H] |
| B-27 | (±)-[3-(2-Fluoro-phenylcarbamoyl)-3-methyl-1,2,3,4-tetrahydro-carbazol-9-yl]-acetic acid | C22H21N2O3F 380.418 | 1.04 (LC-4) | 403.00 [M + Na] |
| B-28 | (±)-[3-(3-Fluoro-phenylcarbamoyl)-3-methyl-1,2,3,4-tetrahydro-carbazol-9-yl]-acetic acid | C22H21N2O3F 380.418 | 1.07 (LC-4) | 403.00 [M + Na] |
| B-29 | (±)-[3-(4-Fluoro-phenylcarbamoyl)-3-methyl-1,2,3,4-tetrahydro-carbazol-9-yl]-acetic acid | C22H21N2O3F 380.418 | 1.05 (LC-4) | 379.04 [M − H] |
| B-30 | (±)-[3-(Methyl-phenyl-carbamoyl)-3-propyl-1,2,3,4-tetrahydro-carbazol-9-yl]-acetic acid | C25H28N2O3 404.508 | 1.12 (LC-4) | 427.03 [M + Na] |
| B-31 | (±)-[3-(4-Fluoro-phenylcarbamoyl)-3-propyl-1,2,3,4-tetrahydro-carbazol-9-yl]-acetic acid | C24H25N2O3F 408.472 | 1.11 (LC-4) | 431.05 [M + Na] |
| B-32 | (±)-[3-(3-Fluoro-phenylcarbamoyl)-3-propyl-1,2,3,4-tetrahydro-carbazol-9-yl]-acetic acid | C24H25N2O3F 408.472 | 1.12 (LC-4) | 431.05 [M + Na] |
| B-33 | (±)-[3-(2-Fluoro-phenylcarbamoyl)-3-propyl-1,2,3,4-tetrahydro-carbazol-9-yl]-acetic acid | C24H25N2O3F 408.472 | 1.10 (LC-4) | 430.89 [M + Na] |
| B-34 | (±)-[3-(Benzhydryl-carbamoyl)-3-propyl-1,2,3,4-tetrahydro-carbazol-9-yl]-acetic acid | C31H32N2O3 480.606 | 1.16 (LC-4) | 503.14 [M + Na] |
| B-35 | (±)-[3-Ethyl-3-(methyl-phenyl-carbamoyl)-1,2,3,4-tetrahydro-carbazol-9-yl]-acetic acid | C24H26N2O3 390.481 | 1.09 (LC-4) | 413.04 [M + Na] |
| B-36 | (±)-[3-(Benzhydryl-carbamoyl)-3-ethyl-1,2,3,4-tetrahydro-carbazol-9-yl]-acetic acid | C30H30N2O3 466.579 | 1.13 (LC-4) | 489.08 [M + Na] |
| B-37 | (±){3-[Benzyl-(3-fluoro-benzyl)-carbamoyl]-3-methyl-1,2,3,4-tetrahydro-carbazol-9-yl}-acetic acid | C30H29N2O3F 484.569 | 1.17 (LC-4) | 485.19 |
| B-38 | (±){3-[Benzyl-(4-fluoro-benzyl)-carbamoyl]-3-methyl-1,2,3,4-tetrahydro-carbazol-9-yl}-acetic acid | C30H29N2O3F 484.569 | 1.17 (LC-4) | 485.19 |
| B-39 | (±)-{3-[Benzyl-(2-trifluoromethyl-benzyl)-carbamoyl]-3-methyl-1,2,3,4-tetrahydro-carbazol-9-yl}-acetic acid | C31H29N2O3F3 534.576 | 1.20 (LC-4) | 557.23 [M + Na] |
| B-40 | (±)-{3-[Benzyl-(3-trifluoromethyl-benzyl)-carbamoyl]-3-methyl-1,2,3,4-tetrahydro-carbazol-9-yl}-acetic acid | C31H29N2O3F3 534.576 | 1.20 (LC-4) | 557.16 [M + Na] |
| B-41 | (±)-{3-[Benzyl-(2,5-difluoro-benzyl)-carbamoyl]-3-methyl-1,2,3,4-tetrahydro-carbazol-9-yl}-acetic acid | C30H28N2O3F2 502.559 | 1.17 (LC-4) | 503.2 |

TABLE 2-continued

Examples B-01 to B-71 are prepared using procedures analogous to those described for Example A-01 or A-02.

| Ex. | Compound Name | Formula MW | LC-MS $t_R$ (Method) | ESI m/z |
|---|---|---|---|---|
| B-42 | (±)-{3-[Benzyl-(3,5-difluoro-benzyl)-carbamoyl]-3-methyl-1,2,3,4-tetrahydro-carbazol-9-yl}-acetic acid | C30H28N2O3F2 502.559 | 1.17 (LC-4) | 503.2 |
| B-43 | (±)-{3-[Benzyl-(4-chloro-2-fluoro-benzyl)-carbamoyl]-3-methyl-1,2,3,4-tetrahydro-carbazol-9-yl]-acetic acid | C30H28N2O3ClF 519.014 | 1.20 (LC-4) | 541.16 [M + Na] |
| B-44 | (±)-(3-{Benzyl-[2-(2-fluoro-phenyl)-ethyl]-carbamoyl}-3-methyl-1,2,3,4-tetrahydro-carbazol-9-yl)-acetic acid | C31H31N2O3F 498.596 | 1.17 (LC-4) | 499.18 |
| B-45 | (±)-(3-{Benzyl-[2-(3-fluoro-phenyl)-ethyl]-carbamoyl}-3-methyl-1,2,3,4-tetrahydro-carbazol-9-yl)-acetic acid | C31H31N2O3F 498.596 | 1.17 (LC-4) | 499.18 |
| B-46 | (±)-(3-{Benzyl-[2-(4-fluoro-phenyl)-ethyl]-carbamoyl}-3-methyl-1,2,3,4-tetrahydro-carbazol-9-yl)-acetic acid | C31H31N2O3F 498.596 | 1.17 (LC-4) | 499.18 |
| B-47 | (±)-(3-{Benzyl-[2-(4-chloro-phenyl)-ethyl]-carbamoyl}-3-methyl-1,2,3,4-tetrahydro-carbazol-9-yl)-acetic acid | C31H31N2O3Cl 515.051 | 1.20 (LC-4) | 515.11 |
| B-48 | (±)-(3-{Benzyl-[2-(2,6-dichloro-phenyl)-ethyl]-carbamoyl}-3-methyl-1,2,3,4-tetrahydro-carbazol-9-yl)-acetic acid | C31H30N2O3Cl2 549.496 | 1.23 (LC-4) | 549.13 |
| B-49 | (±)-[3-Ethyl-3-(2-fluoro-phenylcarbamoyl)-1,2,3,4-tetrahydro-carbazol-9-yl]-acetic acid | C23H23N2O3F 394.445 | 1.06 (LC-4) | 395.15 |
| B-50 | (±)-[3-Ethyl-3-(3-fluoro-phenylcarbamoyl)-1,2,3,4-tetrahydro-carbazol-9-yl]-acetic acid | C23H23N2O3F 394.445 | 1.08 (LC-4) | 395.15 |
| B-51 | (±)-[3-(Benzhydryl-carbamoyl)-3-methyl-1,2,3,4-tetrahydro-carbazol-9-yl]-acetic acid | C29H28N2O3 452.552 | 1.14 (LC-4) | 453.19 |
| B-52 | (±)-[3-(Benzyl-methyl-carbamoyl)-3-methyl-1,2,3,4-tetrahydro-carbazol-9-yl]-acetic acid | C24H26N2O3 390.481 | 1.07 (LC-4) | 391.13 |
| B-53 | (±)-{3-Methyl-3-[(R)-(1,2,3,4-tetrahydro-naphthalen-1-yl)carbamoyl]-1,2,3,4-tetrahydro-carbazol-9-yl}-acetic acid | C26H28N2O3 416.519 | 1.08 (LC-4) | 439.13 [M + Na] |
| B-54 | (±)-{3-Methyl-3-[(naphthalen-1-ylmethyl)-carbamoyl]-1,2,3,4-tetrahydro-carbazol-9-yl}-acetic acid | C27H26N2O3 426.514 | 1.08 (LC-4) | 427.21 |
| B-55 | (±)-[3-(Benzyl-butyl-carbamoyl)-3-methyl-1,2,3,4-tetrahydro-carbazol-9-yl]-acetic acid | C27H32N2O3 432.562 | 1.16 (LC-4) | 453.19 [M + Na] |
| B-56 | (±)-{3-[Benzyl-(2-cyano-ethyl)-carbamoyl]-3-methyl-1,2,3,4-tetrahydro-carbazol-9-yl}-acetic acid | C26H27N3O3 429.518 | 1.06 (LC-4) | 452.15 [M + Na] |
| B-57 | (±)-[3-(Benzyl-ethyl-carbamoyl)-3-methyl-1,2,3,4-tetrahydro-carbazol-9-yl]-acetic acid | C25H28N2O3 404.508 | 1.10 (LC-4) | 405.19 |
| B-58 | (±)-[3-(Benzyl-isopropyl-carbamoyl)-3-methyl-1,2,3,4-tetrahydro-carbazol-9-yl]-acetic acid | C26H30N2O3 418.535 | 1.12 (LC-4) | 417.38 [M − H] |
| B-59 | (±)-[3-(1H,3H-Benzo[d,e]isoquinoline-2-carbonyl)-3-methyl-1,2,3,4-tetrahydro-carbazol-9-yl]-acetic acid | C28H26N2O3 438.525 | 1.11 (LC-4) | 461.08 [M + Na] |
| B-60 | (±)-[3-Methyl-3-(4-pentyl-benzylcarbamoyl)-1,2,3,4-tetrahydro-carbazol-9-yl]-acetic acid | C28H34N2O3 446.589 | 1.17 (LC-4) | 447.23 |
| B-61 | (±)-[3-(4-Fluoro-benzylcarbamoyl)-3-methyl-1,2,3,4-tetrahydro-carbazol-9-yl]-acetic acid | C23H23N2O3F 394.445 | 1.03 (LC-4) | 395.15 |
| B-62 | (±)-[3-(2-Fluoro-benzylcarbamoyl)-3-methyl-1,2,3,4-tetrahydro-carbazol-9-yl]-acetic acid | C23H23N2O3F 394.445 | 1.04 (LC-4) | 395.15 |
| B-63 | (±)-[3-Methyl-3-(2-methylsulfanyl-benzylcarbamoyl)-1,2,3,4-tetrahydro-carbazol-9-yl]-acetic acid | C24H26N2O3S 422.547 | 1.07 (LC-4) | 423.13 |
| B-64 | (±)-[3-(4-Chloro-benzylcarbamoyl)-3-methyl-1,2,3,4-tetrahydro-carbazol-9-yl]-acetic acid | C23H23N2O3Cl 410.9 | 1.06 (LC-4) | 411.08 |
| B-65 | (±)-[3-(2-Chloro-benzylcarbamoyl)-3-methyl-1,2,3,4-tetrahydro-carbazol-9-yl]-acetic acid | C23H23N2O3Cl 410.9 | 1.06 (LC-4) | 411.08 |
| B-66 | (±)-[3-(2-Difluoromethoxy-benzylcarbamoyl)-3-methyl-1,2,3,4-tetrahydro-carbazol-9-yl]-acetic acid | C24H24N2O4F2 442.461 | 1.07 (LC-4) | 443.14 |
| B-67 | (±)-[3-(2,4-Dichloro-benzylcarbamoyl)-3-methyl-1,2,3,4-tetrahydro- | C23H22N2O3Cl2 445.345 | 1.10 (LC-4) | 445.01 |

TABLE 2-continued

Examples B-01 to B-71 are prepared using procedures analogous to those described for Example A-01 or A-02.

| Ex. | Compound Name | Formula MW | $t_R$ (Method) | LC-MS ESI m/z |
|---|---|---|---|---|
| | tetrahydro-carbazol-9-yl]-acetic acid | | | |
| B-68 | (±)-[3-(3,5-Difluoro-benzylcarbamoyl)-3-methyl-1,2,3,4-tetrahydro-carbazol-9-yl]-acetic acid | C23H22N2O3F2 412.435 | 1.04 (LC-4) | 413.09 |
| B-69 | (±)-[3-(3,4-Dichloro-benzylcarbamoyl)-3-methyl-1,2,3,4-tetrahydro-carbazol-9-yl]-acetic acid | C23H22N2O3Cl2 445.345 | 1.09 (LC-4) | 446.19 |
| B-70 | (±)-[3-(2,4-Difluoro-benzylcarbamoyl)-3-methyl-1,2,3,4-tetrahydro-carbazol-9-yl]-acetic acid | C23H22N2O3F2 412.435 | 1.05 (LC-4) | 411.15 [M − H] |
| B-71 | (±)-[3-(2,6-Difluoro-benzylcarbamoyl)-3-methyl-1,2,3,4-tetrahydro-carbazol-9-yl]-acetic acid | C23H22N2O3F2 412.435 | 1.04 (LC-4) | 413.16 |

Example C-01

(±)-[6-Cyano-3-(methyl-phenyl-carbamoyl)-1,2,3,4-tetrahydro-carbazol-9-yl]-acetic acid a) (±)-6-Cyano-2,3,4,9-tetrahydro-1H-carbazole-3-carboxylic acid methyl-phenyl-amide A stirred solution of 4-oxo-cyclohexanecarboxylic acid methyl-phenyl-amide (50 mg, 0.22 mmol) and (4-cyanophenyl)-hydrazine hydrochloric acid salt (36.5 mg, 0.22 mmol) in glacial AcOH (1 ml) is heated to reflux for 1 h. At rt, two drops of conc. H$_2$SO$_4$ are added and the reaction mixture is again heated to reflux for another 1 h, then cooled to rt and poured into 5% aqueous NaOAc. The resulting precipitate is filtered, rinsed several times with H$_2$O and dried under high vacuum providing pure subtitle compound (35 mg) in 49% yield as a white solid. $t_R$ (LC-4) 1.06 min; ESI-MS (positive ion): m/z 329.96 [M]$^+$ (calcd 329.40 for C$_{21}$H$_{19}$N$_3$O). $^1$H-NMR (CDCl$_3$): 2.12 (m, 2H); 2.53 (m, 1H); 2.73 (m, 3H); 2.93 (m, 1H); 3.34 (s, 3H); 7.25 (m, 3H); 7.32 (m, 2H); 7.41 (m, 2H), 7.71 (s, 1H); 8.04 (br s, 1H).

a1) 4-Oxo-cyclohexanecarboxylic acid methyl-phenyl-amide

Oxalyl chloride (0.89 g, 7.0 mmol) and a few drops of dry DMF are added to a stirred solution of 4-oxo-cyclohexanecarboxylic acid (0.50 g, 3.5 mmol) in CH$_2$Cl$_2$ (7 ml) and the reaction is kept stirring at rt overnight. The volatiles are removed under reduced pressure, the residue is azeotroped with toluene and dried under high vacuum yielding crude acid chloride. This material is reacted without further purification with N-methylaniline (0.16 g, 1.5 mmol) in CH$_2$Cl$_2$ (7 ml) in the presence of DIEA (0.58 g, 4.5 mmol). After stirring overnight at rt, saturated aqueous NaHCO$_3$ is added and the mixture extracted three times with CH$_2$Cl$_2$. The combined organic layers are dried over Na$_2$SO$_4$ and evaporated. The residue is column chromatographed on silica gel (hexane/EtOAc 2:1) and the title compound is obtained as a pale yellow solid (0.47 g) in 57% yield. $t_R$ (LC-4) 0.89 min; ESI-MS (positive ion): m/z 231.98 [M]$^+$ (calcd 231.13 for C$_{14}$H$_{17}$NO$_2$).
$^1$H-NMR (CDCl$_3$): 2.04 (m, 6H); 2.45 (m, 2H); 2.65 (m, 1H); 3.28 (s, 3H); 7.22 (m, 2H); 7.44 (m, 3H).

b) Ethyl (±)-[6-cyano-3-(methyl-phenyl-carbamoyl)-1,2,3,4-tetrahydro-carbazol-9-yl]-acetate To a stirred solution of (±)-6-cyano-2,3,4,9-tetrahydro-1H-carbazole-3-carboxylic acid methyl-phenyl-amide (0.14 g, 0.43 mmol) in dry DMF (1.5 ml) is added KOtBu (58 mg, 0.52 mmol) and ethyl bromoacetate (79 mg, 0.47 mmol). The reaction mixture is stirred at rt overnight, then poured into saturated aqueous KH$_2$PO$_4$ and extracted with CH$_2$Cl$_2$. The combined organic layers are washed with H$_2$O and brine, dried over Na$_2$SO$_4$, filtered and evaporated. The residue is purified by column chromatography on silica gel (hexane/EtOAc 1:1) to provide subtitle compound (91 mg) as a beige solid in 51% yield. $t_R$ (LC-3) 1.15 min; ESI-MS (positive ion): m/z 416.09 [M+H]$^+$ (calcd 415.19 for C$_{25}$H$_{25}$N$_3$O$_3$).
$^1$H-NMR (CDCl$_3$): 1.13 (t, J=7.0 Hz, 3H); 1.79 (m, 1H); 2.05 (m, 1H); 2.25 (m, 1H); 2.65 (m, 1H); 2.72 (m, 2H); 3.19 (s, 3H); 3.24 (m, 1H); 4.07 (q, J=7.0 Hz, 2H); 5.00 (d, J=3.3 Hz, 2H); 7.33 (m, 1H); 7.41 (m, 5H); 7.50 (d, J=8.0 Hz, 1H); 7.87 (s, 1H).

c) (±)-[6-Cyano-3-(methyl-phenyl-carbamoyl)-1,2,3,4-tetrahydro-carbazol-9-yl]-acetic acid Ethyl [6-cyano-3-(methyl-phenyl-carbamoyl)-1,2,3,4-tetrahydro-carbazol-9-yl]-acetate is saponified analogous to the conditions described for Example 1 yielding the title compound: $t_R$ (LC-4) 1.05 min; ESI-MS (positive ion): m/z 388.06 [M+H]$^+$ (calcd 387.44 for C$_{23}$H$_{21}$N$_3$O$_3$). $^1$H-NMR (CDCl$_3$): 1.76 (m, 1H); 1.99 (m, 1H); 2.20 (m, 1H); 2.64 (m, 3H); 3.15 (s, 3H); 3.26 (m, 1H); 4.83 (s, 2H); 7.36 (m, 7H); 7.81 (s, 1H).

TABLE 3

Examples C-02 to C-38 are prepared using a procedure analogous to that described for Example C-01, Example A-01 or A-02.

| Ex. | Compound Name | Formula MW | $t_R$ (Method) | LC-MS ESI m/z |
|---|---|---|---|---|
| C-02 | (±)-[6-Methyl-3-(methyl-phenyl-carbamoyl)-1,2,3,4-tetrahydro-carbazol-9-yl]-acetic acid | C23H24N2O3 376.455 | 2.28 (LC-3) | 377.2 |
| C-03 | (±)-[6-Fluoro-3-(methyl-phenyl-carbamoyl)-1,2,3,4-tetrahydro-carbazol-9-yl]-acetic acid | C22H21N2O3F 380.418 | 2.19 (LC-3) | 381.15 |
| C-04 | (±)-[6-Chloro-3-(methyl-phenyl-carbamoyl)-1,2,3,4-tetrahydro-carbazol-9-yl]-acetic acid | C22H21N2O3Cl 396.873 | 2.31 (LC-3) | 397.14 |
| C-05 | (±)-[6-Iodo-3-(methyl-phenyl-carbamoyl)-carbazol-9-yl1,2,3,4-tetrahydro]-acetic acid | C22H21N2O3I 488.32 | 2.44 (LC-3) | 489.00 |
| C-06 | (±)-[6-Bromo-3-(methyl-phenyl- | C22H21N2O3Br 441.324 | 2.38 (LC-3) | 443.00 |

TABLE 3-continued

Examples C-02 to C-38 are prepared using a procedure analogous to that described for Example C-01, Example A-01 or A-02.

| Ex. | Compound Name | Formula MW | $t_R$ (Method) | ESI m/z |
|---|---|---|---|---|
| | carbamoyl)-1,2,3,4-tetrahydro-carbazol-9-yl]-acetic acid | | | |
| C-07 | (±)-[6-Methoxy-3-(methyl-phenyl-carbamoyl)-1,2,3,4-tetrahydro-carbazol-9-yl]-acetic acid | C23H24N2O4 392.454 | 2.17 (LC-3) | 393.13 |
| C-08 | (±)-[7-Chloro-3-(methyl-phenyl-carbamoyl)-1,2,3,4-tetrahydro-carbazol-9-yl]-acetic acid | C22H21N2O3Cl 396.873 | 2.34 (LC-3) | 397.07 |
| C-09 | (±)-[6-Isopropyl-3-(methyl-phenyl-carbamoyl)-1,2,3,4-tetrahydro-carbazol-9-yl]-acetic acid | C25H28N2O3 404.508 | 2.22 (LC-3) | 405.16 |
| C-10 | (±)-[8-Chloro-3-(methyl-phenyl-carbamoyl)-1,2,3,4-tetrahydro-carbazol-9-yl]-acetic acid | C22H21N2O3Cl 396.873 | 2.09 (LC-3) | 397.07 |
| C-11 | (±)-[3-(Methyl-phenyl-carbamoyl)-6-nitro-1,2,3,4-tetrahydro-carbazol-9-yl]-acetic acid | C22H21N3O5 407.425 | 1.08 (LC-4) | 408.06 |
| C-12 | (±)-[3-(Methyl-phenyl-carbamoyl)-6-trifluoromethyl-1,2,3,4-tetrahydro-carbazol-9-yl]-acetic acid | C23H21N2O3F3 430.425 | 1.13 (LC-4) | 431.04 |
| C-13 | (±)-[7-Methyl-3-(methyl-phenyl-carbamoyl)-1,2,3,4-tetrahydro-carbazol-9-yl]-acetic acid | C23H24N2O3 376.455 | 1.03 (LC-2) | 377.04 |
| C-14 | (±)-[8-Chloro-3-(indan-2-ylcarbamoyl)-1,2,3,4-tetrahydro-carbazol-9-yl]-acetic acid | C24H23N2O3Cl 422.911 | 0.97 (LC-5) | 423.23 |
| C-15 | (±)-[8-Chloro-3-(2,2-diphenyl-ethylcarbamoyl)-1,2,3,4-tetrahydro-carbazol-9-yl]-acetic acid | C29H27N2O3Cl 486.997 | 1.02 (LC-5) | 487.29 |
| C-16 | (±)-[8-Chloro-3-(2,3-dihydro-indole-1-carbonyl)-1,2,3,4-tetrahydro-carbazol-9-yl]-acetic acid | C23H21N2O3Cl 408.884 | 0.99 (LC-5) | 409.2 |
| C-17 | (±)-{8-Chloro-3-[4-(4-fluoro-phenyl)-piperazine-1-carbonyl]-1,2,3,4-tetrahydro-carbazol-9-yl}-acetic acid | C25H25N3O3ClF 469.943 | 0.97 (LC-5) | 470.27 |
| C-18 | (±)-[3-(Benzhydryl-methyl-carbamoyl)-8-chloro-1,2,3,4-tetrahydro-carbazol-9-yl]-acetic acid | C29H27N2O3Cl 486.997 | 1.06 (LC-5) | 487.31 |
| C-19 | (±)-[3-(Benzhydryl-carbamoyl)-8-chloro-1,2,3,4-tetrahydro-carbazol-9-yl]-acetic acid | C28H25N2O3Cl 472.971 | 1.01 (LC-5) | 473.3 |
| C-20 | (±)-[3-(4-Benzhydryl-piperazine-1-carbonyl)-8-chloro-1,2,3,4-tetrahydro-carbazol-9-yl]-acetic acid | C32H32N3O3Cl 542.077 | 0.87 (LC-5) | 542.35 |
| C-21 | (+)-[3-(2,3-Dihydro-indole-1-carbonyl)-6-fluoro-1,2,3,4-tetrahydro-carbazol-9-yl]-acetic acid | C23H21N2O3F 392.429 | 13.8 (LC-8) | 393.14 |
| C-22 | (+)-[6-Fluoro-3-(methyl-phenyl-carbamoyl)-1,2,3,4-tetrahydro-carbazol-9-yl]-acetic acid | C22H21N2O3F 380.418 | 6.8 (LC-8) | 381.09 |
| C-23 | (+)-[3-(Benzhydryl-methyl-carbamoyl)-6-fluoro-1,2,3,4-tetrahydro-carbazol-9-yl]-acetic acid | C29H27N2O3F 470.542 | 1.14 (LC-4) | 471.13 |
| C-24 | (+)-{6-Fluoro-3-[4-(4-fluoro-phenyl)-piperazine-1-carbonyl]-1,2,3,4-tetrahydro-carbazol-9-yl}-acetic acid | C25H25N3O3F2 453.488 | 1.08 (LC-4) | 454.23 |
| C-25 | (+)-[3-(Benzyl-isopropyl-carbamoyl)-6-fluoro-1,2,3,4-tetrahydro-carbazol-9-yl]-acetic acid | C25H27N2O3F 422.498 | 7.2 (LC-8) | 423.16 |
| C-26 | (+)-[3-(Benzyl-phenethyl-carbamoyl)-6-fluoro-1,2,3,4-tetrahydro-carbazol-9-yl]-acetic acid | C30H29N2O3F 484.569 | 10.0 (LC-8) | 485.26 |
| C-27 | (+)-[3-(Azocane-1-carbonyl)-6-fluoro-1,2,3,4-tetrahydro-carbazol-9-yl]-acetic acid | C22H27N2O3F 386.465 | 6.5 (LC-8) | 387.25 |
| C-28 | (+)-{3-[Benzyl-((S)-1-phenyl-ethyl)-carbamoyl]-6-fluoro-1,2,3,4-tetrahydro-carbazol-9-yl}-acetic acid | C30H29N2O3F 484.569 | 9.0 (LC-8) | 485.19 |
| C-29 | (+)-{3-[Benzyl-((R)-1-phenyl-ethyl)-carbamoyl]-6-fluoro-1,2,3,4-tetrahydro-carbazol-9-yl}-acetic acid | C30H29N2O3F 484.569 | 7.4 (LC-8) | 485.33 |
| C-30 | (+)-[6-Fluoro-3-((R)-1-phenyl-ethylcarbamoyl)-1,2,3,4-tetrahydro-carbazol-9-yl]-acetic acid | C23H23N2O3F 394.445 | 10.6 (LC-9) | 395.15 |
| C-31 | (−)-[3-(Benzhydryl-methyl-carbamoyl)-6-fluoro-1,2,3,4-tetrahydro-carbazol-9-yl]-acetic acid | C29H27N2O3F 470.542 | 1.21 (LC-4) | 471.47 |
| C-32 | (−)-{6-Fluoro-3-[4-(4-fluoro-phenyl)-piperazine-1-carbonyl]-1,2,3,4-tetrahydro-carbazol-9-yl}-acetic acid | C25H25N3O3F2 453.488 | 1.09 (LC-2) | 454.23 |

TABLE 3-continued

Examples C-02 to C-38 are prepared using a procedure analogous to that described for Example C-01, Example A-01 or A-02.

| Ex. | Compound Name | Formula MW | $t_R$ (Method) | LC-MS ESI m/z |
|---|---|---|---|---|
| C-33 | (−)-[3-(Benzyl-isopropyl-carbamoyl)-6-fluoro-1,2,3,4-tetrahydro-carbazol-9-yl]-acetic acid | C25H27N2O3F 422.498 | 6.5 (LC-8) | 423.2 |
| C-34 | (−)-[3-(Benzyl-phenethyl-carbamoyl)-6-fluoro-1,2,3,4-tetrahydro-carbazol-9-yl]-acetic acid | C30H29N2O3F 484.569 | 10.3 (LC-8) | 485.19 |
| C-35 | (−)-[3-(Azocane-1-carbonyl)-6-fluoro-1,2,3,4-tetrahydro-carbazol-9-yl]-acetic acid | C22H27N2O3F 386.465 | 7.8 (LC-8) | 387.19 |
| C-36 | (−)-{3-[Benzyl-((S)-1-phenyl-ethyl)-carbamoyl]-6-fluoro-1,2,3,4-tetrahydro-carbazol-9-yl}-acetic acid | C30H29N2O3F 484.569 | 9.0 (LC-8) | 485.46 |
| C-37 | (−)-{3-[Benzyl-((R)-1-phenyl-ethyl)-carbamoyl]-6-fluoro-1,2,3,4-tetrahydro-carbazol-9-yl}-acetic acid | C30H29N2O3F 484.569 | 8.0 (LC-8) | 485.4 |
| C-38 | (−)-[6-Fluoro-3-((R)-1-phenyl-ethylcarbamoyl)-1,2,3,4-tetrahydro-carbazol-9-yl]-acetic acid | C23H23N2O3F 394.445 | 7.5 (LC-9) | 395.08 |

Example D-01

Benzyl (±)-9-carboxymethyl-2,3,4,9-tetrahydro-1H-carbazole-3-carboxylate a) Benzyl (±)-9-ethoxycarbonylmethyl-2,3,4,9-tetrahydro-1H-carbazole-3-carboxylate Cesium carbonate (0.32 g, 1.0 mmol) and benzylbromide (60 mg, 0.35 mmol) are added to a stirred solution of Intermediate 1.1 (100 mg, 0.33 mmol) in dry DMF (1 ml). The resulting suspension is stirred at rt for 2 h, poured into saturated aqueous $KH_2PO_4$ solution and extracted three times with diethyl ether. The combined organic layers are washed with $H_2O$ and brine, dried over $Na_2SO_4$ and evaporated. The residue is crystallized from diisopropyl ether to give pure subtitle compound (95 mg) as a white solid in 73% yield. $t_R$ (LC-4) 1.21 min; MS (positive ion) m/z 392.94 [M+H]$^+$ (calcd 391.18 for $C_{24}H_{25}NO_4$).

$^1$H-NMR (CDCl$_3$): 1.06 (m, 3H); 1.89 (m, 1H); 2.17 (m, 1H); 2.56 (m, 2H); 2.73 (m, 2H); 2.90 (m, 1H); 3.98 (m, 2H); 4.51 (d, J=12.8 Hz, 2H); 4.98 (d, J=12.8 Hz, 2H); 6.94 (m, 3H); 7.12 (m, 5H); 7.27 (m, 1H).

b) Benzyl (±)-9-carboxymethyl-2,3,4,9-tetrahydro-1H-carbazole-3-carboxylate

Benzyl (±)-9-ethoxycarbonylmethyl-2,3,4,9-tetrahydro-1H-carbazole-3-carboxylate is saponified analogous to the conditions described for Example A-01 yielding pure title compound: $t_R$ (LC-4) 1.09 min; ESI-MS (positive ion): m/z 364.96 [M]$^+$ (calcd 363.41 for $C_{22}H_{21}NO_4$).

Example D-02

(R)-1-Phenyl-ethyl (±)-9-carboxymethyl-2,3,4,9-tetrahydro-1H-carbazole-3-carboxylate a) Ethyl (±)-(3-chlorocarbonyl-1,2,3,4-tetrahydro-carbazol-9-yl)-acetate Oxalyl chloride (1.26 g, 10 mmol) is dropwise added to a solution of Intermediate 1.1 (1.5 g, 5 mmol) in dry $CH_2Cl_2$ and the resulting orange solution is stirred overnight at rt. The volatiles are removed under reduced pressure and the residue is azeoptroped twice with dry toluene and then dried under high vacuum to leave the crude subtitle compound as brownish oil, which is used without further purification.

b): (R)-1-Phenyl-ethyl (±)-9-ethoxycarbonylmethyl-2,3,4,9-tetrahydro-1H-carbazole-3-carboxylate Crude ethyl (±)-(3-chlorocarbonyl-1,2,3,4-tetrahydro-carbazol-9-yl)-acetate (5 mmol) is dissolved in dry $CH_2Cl_2$ and treated with (R)-1-phenyl-ethanol (0.55 g, 5.4 mmol), DIEA (1.94 g, 15 mmol) and DMAP (61 mg, 0.5 mmol). The resulting yellow solution is stirred at rt overnight, diluted with EtOAc and successively washed with 0.1 N HCl, saturated aqueous $NaHCO_3$, $H_2O$ and brine. The organic layer is dried over $Na_2SO_4$, filtered and evaporated. The residue is purified by column chromatography on silica gel (hexane/EtOAc 5:1) to provide the subtitle compound as yellow oil (1.36 g) in 76% yield.

$t_R$ (LC-4) 1.23 min; ESI-MS (positive ion): m/z 406.14 [M+H]$^+$ (calcd 405.49 for $C_{25}H_{27}NO_4$).

$^1$H-NMR (CDCl$_3$): 1.24 (t, J=7.1 Hz, 3H); 1.56 (d, J=6.5 Hz, 3H); 2.05 (m, 1H); 2.34 (m, 1H); 2.87 (m, 4H); 3.12 (m, 1H); 4.18 (q, J=6.5 Hz, 2H); 4.71 (s, 2H); 5.95 (q, J=6.5 Hz, 1H); 7.14 (m, 3H); 7.34 (m, 5H); 7.48 (m, 1H).

c) (R)-1-Phenyl-ethyl (±)-9-carboxymethyl-2,3,4,9-tetrahydro-1H-carbazole-3-carboxylate A stirred solution of (R)-1-phenyl-ethyl (±)-9-ethoxycarbonylmethyl-2,3,4,9-tetrahydro-1H-carbazole-3-carboxylate (50 mg, 0.123 mmol) in THF (1.1 ml) is treated with 0.2 N aqueous NaOH (0.555 ml, 0.111 mmol) at rt for 1 h. The basic reaction mixture is washed three times with diethyl ether and the aqueous phase is evaporated to dryness. The resulting solid is recrystallized from diisopropyl ether to give the pure sodium salt of the title compound as a white solid (30 mg) in 61% yield.

$t_R$ (LC-4) 1.16 min; ESI-MS (positive ion): m/z 399.97 [M]$^+$ (calcd 399.41 for $C_{23}H_{22}NNaO_4$).

$^1$H-NMR (DMSO-d$_6$): 1.48 (d, J=5.8 Hz, 3H); 1.83 (m, 1H); 2.21 (m, 1H); 2.74 (m, 4H); 2.95 (m, 1H); 4.23 (s, 2H); 5.84 (q, J=5.8 Hz, 1H); 6.88 (t, J=7.2 Hz, 1H); 6.95 (t, J=7.2 Hz, 1H); 7.15 (d, J=8.1 Hz, 1H); 7.32 (m, 6H).

Biological Assays:

Preparation of CRTH2 Membranes and Radioligand Binding Assay:

Preparation of the membranes and radioligand binding assays are performed according to known procedures, e.g. Sawyer N. et al. (*Br. J. Pharmacol.*, 2002, 137, 1163-1172). A clonal HEK 293 cell line, expressing high level of recombinant hCRTH2 receptor, is selected for the preparation of membranes. Cells are detached from culture plates in 5 ml buffer A (5 mM Tris, 1 mM MgCl$_2$×6 H$_2$O, 0.1 mM PMSF, 0.1 mM phenanthroline) per plate using a police rubber and transferred into centrifugation tubes and frozen at −80° C. After thawing, the cells are centrifuged at 500 g for 5 min and then resuspended in buffer A. Cells are then fragmented by homogenization with a Polytron homogenizer for 30 s. The membrane fragments are centrifuged at 3000 g for 40 min and resuspended in membranes in buffer B (50 mM Tris, 25 mM MgCl$_2$, 250 mM saccharose, pH 7.4) and aliquots are stored frozen.

Binding assay is performed in a total volume of 250 µl. In each well, 75 µl buffer C (50 mM Tris, 100 mM NaCl, 1 mM EDTA, 0.1% BSA (protease free), 0.01% NaN$_3$, pH 7.4) is mixed with 50 µl {$^3$H}-PGD$_2$ (at 2.5 nM (220.000 dpm per well) from Amersham, TRK734), 100 µl CRTH2 membranes to give 80 µg per well and 25 µl of test compound in buffer C containing 1% DMSO. For unspecific binding, PGD2 is added to the reaction mixture at 1 µM final concentration. This binding assay mix is incubated at rt for 90 min and then filtered through a GF/C filter plate. The filter is washed three times with ice cold binding buffer. Then, 40 µl per well Microscint-40 (Packard) are added and the bound radioactivity is quantified by means of Topcount (Packard).

Test for Antagonist Binding to the CRTH2 Receptor:

Compounds of Formula I displayed IC$_{50}$ values of less than 10 µM, as exemplified in the following Table 4.

TABLE 4

| Compound Name | hCRTH2 BDG IC$_{50}$ [µM] |
| --- | --- |
| (±)-{3-[(3-Chloro-phenyl)-methyl-carbamoyl]-3-methyl-1,2,3,4-tetrahydro-carbazol-9-yl}-acetic acid | 0.001 |
| (±)-[3-(2,3-Dihydro-indole-1-carbonyl)-1,2,3,4-tetrahydro-carbazol-9-yl]-acetic acid | 0.002 |
| (±)-[3-Methyl-3-(phenyl-thiophen-3-ylmethyl-carbamoyl)-1,2,3,4-tetrahydro-carbazol-9-yl]-acetic acid | 0.002 |
| (±)-[3-Methyl-3-(methyl-phenyl-carbamoyl)-1,2,3,4-tetrahydro-carbazol-9-yl]-acetic acid | 0.003 |
| (±)-[3-(Benzyl-phenyl-carbamoyl)-3-methyl-1,2,3,4-tetrahydro-carbazol-9-yl]-acetic acid | 0.003 |
| (+)-[3-(Benzyl-isopropyl-carbamoyl)-6-fluoro-1,2,3,4-tetrahydro-carbazol-9-yl]-acetic acid | 0.003 |
| (±)-[3-(3,5-Difluoro-benzylcarbamoyl)-3-methyl-1,2,3,4-tetrahydro-carbazol-9-yl]-acetic acid | 0.019 |
| (±)-[3-(3-Fluoro-phenylcarbamoyl)-3-propyl-1,2,3,4-tetrahydro-carbazol-9-yl]-acetic acid | 0.022 |
| (−)-[3-(Benzyl-isopropyl-carbamoyl)-6-fluoro-1,2,3,4-tetrahydro-carbazol-9-yl]-acetic acid | 0.067 |

Intracellular Calcium Mobilization Assay (FLIPR):

Cells (HEK-293), stably expressing the hCRTH$_2$ receptor under the control of the cytomegalovirus promotor from a single insertion of the expression vector pcDNA5 (Invitrogen), are grown to confluency in DMEM (low glucose, Gibco) medium supplemented with 10% fetal calf serum (both Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 µM Fluo-4 and 0.04% Pluronic F-127 (both Molecular Probes), 20 mM HEPES (Gibco) in assay buffer, the cells are washed with and resuspended in assay buffer, then seeded onto 384-well FLIPR assay plates (Greiner) at 50,000 cells in 66 µl per well, and sedimented by centrifugation.

Stock solutions of test compounds are made up at a concentration of 10 mM in DMSO, and serially diluted in assay buffer to concentrations required for inhibition dose response curves. Prostaglandin D$_2$ (Biomol, Plymouth Meeting, Pa.) is used as an agonist.

A FLIPR384 instrument (Molecular Devices) is operated according to the manufacturer's standard instructions, adding 4 µl of test compound dissolved at 10 mM in DMSO and diluted prior to the experiment in assay buffer to obtain the desired final concentration. 10 µl of 80 nM prostaglandin D$_2$ (Biomol, Plymouth Meeting, Pa.) in assay buffer, supplemented with 0.8% bovine serum albumin (fatty acid content<0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin D$_2$ addition are exported after base line subtraction. Values are normalized to high-level control (no test compound added) after subtraction of base line value (no prostaglandin D$_2$ added). The program XL1fit 3.0 (IDBS) is used to fit the data to a single site dose response curve of the equation (A+((B−A)/(1+((C/x)^D)))) and to calculate the IC$_{50}$ values.

Antagonist Analysis:

Compounds of Formula I antagonize prostaglandin D2 mediated hCRTH2 receptor activity with an IC$_{50}$ less than 10 µM as exemplified in the following Table 5.

TABLE 5

| Compound Name | hCRTH2 FLIPR IC$_{50}$ [µM] |
| --- | --- |
| (±)-[3-(Methyl-phenyl-carbamoyl)-6-nitro-1,2,3,4-tetrahydro-carbazol-9-yl]-acetic acid | 0.011 |
| (±)-[3-Methyl-3-(methyl-phenyl-carbamoyl)-1,2,3,4-tetrahydro-carbazol-9-yl]-acetic acid | 0.013 |
| (±)-[3-(Benzhydryl-methyl-carbamoyl)-1,2,3,4-tetrahydro-carbazol-9-yl]-acetic acid | 0.017 |
| (±)-{3-[(3-Chloro-phenyl)-methyl-carbamoyl]-3-methyl-1,2,3,4-tetrahydro-carbazol-9-yl}-acetic acid | 0.020 |
| (±)-{3-[Methyl-(2-trifluoromethyl-phenyl)-carbamoyl]-1,2,3,4-tetrahydro-carbazol-9-yl}-acetic acid | 0.045 |
| (+)-[3-(2,3-Dihydro-indole-1-carbonyl)-6-fluoro-1,2,3,4-tetrahydro-carbazol-9-yl]-acetic acid | 0.028 |
| (+)-[3-(Azocane-1-carbonyl)-6-fluoro-1,2,3,4-tetrahydro-carbazol-9-yl]-acetic acid | 0.046 |
| (±)-{3-[Benzyl-(2-cyano-ethyl)-carbamoyl]-3-methyl-1,2,3,4-tetrahydro-carbazol-9-yl}-acetic acid | 0.036 |
| [3-(2,3-Dihydro-indole-1-carbonyl)-3-ethyl-1,2,3,4-tetrahydro-carbazol-9-yl]-acetic acid | 0.067 |
| (−)-{6-Fluoro-3-[4-(4-fluoro-phenyl)-piperazine-1-carbonyl]-1,2,3,4-tetrahydro-carbazol-9-yl}-acetic acid | 0.599 |

The compounds of the invention can be formulated as the active ingredient according to methods known per se to give pharmaceutical preparations of the following compositions:

Example E-01

Gelatin Solution

A sterile-filtered aqueous solution, with 20% cyclodextrins as solubilisers, of one of the compounds of Formula I mentioned in the preceding Examples (e.g. Example A-02 as active ingredient), is so mixed under aseptic conditions, with heating, with a sterile gelatin solution containing phenol as preservative, that 1.0 ml of solution has the following composition:

| | |
|---|---|
| active ingredient | 3 mg |
| gelatin | 150.0 mg |
| phenol | 4.7 mg |
| dist. water with 20% cyclodextrins as solubilisers | 1.0 ml |

Example E-02

Sterile Dry Substance for Injection 5 mg of one of a compound of Formula I mentioned in the preceding Examples (e.g. Example B-02) as active ingredient are dissolved in 1 ml of an aqueous solution with 20 mg of mannitol and 20% cyclodextrins as solubilisers. The solution is sterile-filtered and introduced under aseptic conditions into a 2 ml ampoule, deep-frozen and lyophilized. Before use, the lyophilisate is dissolved in 1 ml of distilled water or 1 ml of physiological saline solution. The solution is administered intramuscularly or intravenously. This formulation can also be introduced into a twin-chambered injection ampoule.

Example E-03

Film-Coated Tablets

The following ingredients are used for the preparation of 10,000 tablets each containing 100 mg of the active ingredient:

| | |
|---|---|
| active ingredient | 1000 g |
| corn starch | 680 g |
| colloidal silica | 200 g |
| magnesium stearate | 20 g |
| stearic acid | 50 g |
| sodium carboxymethyl starch | 250 g |
| water | quantum satis |

A mixture of one of the compounds of Formula I mentioned in the preceding Examples (e.g. Example B-10) as active ingredient, 50 g of corn starch and the colloidal silica is processed with a starch paste, made from 250 g of corn starch and 2.2 kg of demineralised water, to form a moist mass. This is forced through a sieve having a mesh size of 3 mm and dried at 45° C. for 30 min in a fluidized bed drier. The dry granulates are pressed through a sieve having a mesh size of 1 mm, mixed with a pre-sieved mixture (1 mm sieve) of 330 g of corn starch, the magnesium stearate, the stearic acid and the sodium carboxymethyl starch, and compressed to form slightly biconvex tablets.

Example E-04

Soft Capsules 5000 soft gelatin capsules, each comprising as active ingredient 0.05 g of one of the compounds of Formula I mentioned in the preceding Examples (e.g. C-03) are prepared as follows:

| | |
|---|---|
| active ingredient | 250 g |
| lauroglycol ® | 2 liters |

The pulverized active ingredient is suspenden in Lauroglykol® (propylene glycol laureate, Glattefossé S. A., Saint Priest, France) and ground in a wet pulverizer to produce a particle size of about 1 to 3 μm. 0.42 g portions of the mixture are then introduced into soft gelatin capsules using a capsule-filling machine.

The invention claimed is:

1. A compound of Formula I:

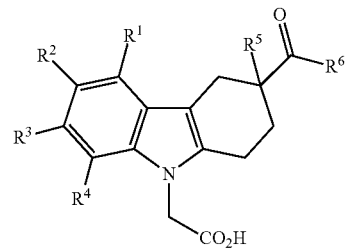

wherein
$R^1$, $R^2$, $R^3$, and $R^4$ independently represent hydrogen, alkyl, alkoxy, halogen, nitro, cyano, trifluoromethyl, or formyl;
$R^5$ represents hydrogen, alkyl, or —$CF_3$; and
$R^6$ represents alkoxy, benzyloxy, 1-phenyl-ethoxy, or —$NR^7R^8$,
wherein
$R^7$ and $R^8$ independently represent hydrogen; alkyl; cyanoalkyl alkenyl; a phenyl or naphthyl group, said groups being optionally mono-substituted by halogen, alkyl, alkoxy, —$CF_3$, —$OCF_3$, phenyl-alkyl or phenyl-carbonyl; a phenyl or naphthyl group, said groups being di-substituted with a halogen, alkoxy or phenyl; phenyl-alkyl optionally substituted in the alkyl chain by phenyl or optionally substituted in the phenyl ring by methylendioxy; phenyl-alkyl which is di-substituted by halogen or mono-substituted by halogen, —$CF_3$, —$OCHF_2$, alkyl or alkylsulfanyl; naphthyl-alkyl; phenylcarbonyl; cycloalkyl, wherein cycloalkyl refers to a cyclopentyl or cyclohexyl group, wherein said groups are optionally substituted with an annulated benzene ring; pyridyl-alkyl; thienyl-alkyl; furanyl-alkyl; or imidazolyl-alkyl; or
$R^7$ and $R^8$, together with the nitrogen atom to which they are attached, form a heterocyclic 5-, 6-, 7-, or 8-membered ring system with 1 or 2 nitrogen and which ring system is optionally substituted with (i) one or two annulated benzene rings, wherein the benzene rings are unsubstituted or substituted with one or two C1-C4 alkyl, C1-C4 alkoxy, halogen, —$CF_3$, or —$OCF_3$; (ii) an unsubstituted phenyl ring; (iii) a mono- or di-substituted phenyl ring, wherein the substituents are halogen, C1-C4 alkyl, C1-C4 alkoxy, —$CF_3$, and —$OCF_3$; or (iv) phenyl-alkyl wherein the alkyl chain is substituted by phenyl;
or an optically pure enantiomer, a mixture of enantiomers, an optically pure diastereomer, a mixture of diastereomers, a mixture of an enantiomer and a diasteromer, a meso form, or a geometric isomer, thereof; or a pharmaceutically acceptable salt thereof.

2. The compound according to claim 1, wherein
$R^1$, $R^2$, $R^3$, and $R^4$ independently represent hydrogen, alkyl, alkoxy, halogen, nitro, cyano, trifluoromethyl, or formyl;

$R^5$ represents hydrogen, alkyl, or —$CF_3$; and $R^6$ represents alkoxy; benzyloxy; 1-phenyl-ethoxy; or —$NR^7R^8$, wherein $R^7$ and $R^8$ independently represent hydrogen; alkyl; cyano-alkyl; alkenyl; phenyl optionally mono-substituted by halogen, alkyl, alkoxy, —$CF_3$, —$OCF_3$, phenyl-alkyl or phenyl-carbonyl; phenyl, di-substituted with halogen, alkoxy and phenyl; naphthyl; phenyl-alkyl optionally substituted in the alkyl chain by phenyl or optionally substituted in the phenyl ring by methylendioxy; phenyl-alkyl which is di-substituted by halogen or mono-substituted by halogen, —$CF_3$, —$OCHF_2$, alkyl or alkylsulfanyl; naphthyl-alkyl; phenylcarbonyl; cycloalkyl, wherein cycloalkyl refers to a cyclopentyl or cyclohexyl group, wherein said groups are optionally substituted with an annulated benzene ring; pyridyl-alkyl; thienyl-alkyl; furanyl-alkyl; or imidazolyl-alkyl; or $R^7$ and $R^8$, together with the nitrogen atom to which they are attached, form a heterocyclic 5-, 6-, 7-, or 8-membered ring system with 1 or 2 nitrogen heteroatoms and which ring system is optionally substituted with (i) one or two annulated benzene rings, wherein the benzene rings are unsubstituted or substituted with one or two C1-C4 alkyl, C1-C4 alkoxy, halogen, —$CF_3$, or —$OCF_3$; (ii) an unsubstituted phenyl ring; or (iii) a mono- or di-substituted phenyl ring substituted with halogen, C1-C4 alkyl, C1-C4 alkoxy, —$CF_3$, or —$OCF_3$;

or a pharmaceutically acceptable salt thereof.

3. The compound according to claim 1 or 2, wherein $R^1$, $R^2$, $R^3$ and $R^4$ independently represent $C_1$-$C_4$ alkyl, $C_1$-$C_4$ alkoxy, halogen, nitro, cyano, or trifluoromethyl; or a pharmaceutically acceptable salt thereof.

4. The compound according to claim 1 or 2, wherein $R^1$, $R^2$, $R^3$ and $R^4$ independently represent methyl, trifluoromethyl, methoxy, fluoro, chloro, bromo, or iodo; or a pharmaceutically acceptable salt thereof.

5. The compound according to claim 1 or 2, wherein $R^7$ represents alkenyl; alkyl; phenyl-C1-C4 alkyl optionally substituted in the alkyl chain by phenyl or optionally substituted in the phenyl ring by methylendioxy; phenyl-C1-C4 alkyl which is di-substituted by halogen or mono-substituted by halogen, —$CF_3$, —$OCHF_2$, alkyl or alkylsulfanyl; naphthyl-C1-C4 alkyl; cycloalkyl, wherein cycloalkyl refers to a cyclopentyl or cyclohexyl group, wherein said groups are optionally substituted with an annulated benzene ring; thienyl-C1-C4 alkyl; furanyl-C1-C4 alkyl; pyridyl-C1-C4 alkyl; or imidazolyl-C1-C4 alkyl; and $R^8$ represents hydrogen; phenyl optionally mono-substituted by halogen, alkyl, alkoxy, —$CF_3$, —$OCF_3$, phenyl-alkyl or phenyl-carbonyl; phenyl, di-substituted with halogen, alkoxy or phenyl; naphthyl; phenyl-C1-C4 alkyl optionally substituted in the alkyl chain by phenyl or optionally substituted in the phenyl ring by methylendioxy; phenyl-C1-C4 alkyl which is di-substituted by halogen or mono-substituted by halogen, —$CF_3$, —$OCHF_2$, alkyl or alkylsulfanyl; naphthyl-C1-C4 alkyl; furanyl-C1-C4 alkyl, pyridyl-C1-C4 alkyl, or thienyl-C1-C4 alkyl;

or a pharmaceutically acceptable salt thereof.

6. The compound according to, wherein $R^7$ represents hydrogen, allyl, 2-cyano-ethyl, methyl, butyl, ethyl, isopropyl, benzyl, 1-phenyl-ethyl, 2-phenyl-ethyl, phenyl-propyl, cyclohexyl, or thiophen-3-ylmethyl; and $R^8$ represents phenyl, 2-benzoyl-phenyl, 2-methoxy-phenyl, 2-methyl-phenyl, 2-trifluoromethyl-phenyl, 3,4-dichloro-phenyl, 3-benzoyl-phenyl, 3-chloro-phenyl, 2-fluoro-phenyl, 3-fluoro-phenyl, 4-chloro-phenyl, 4-fluoro-phenyl, 4-methoxy-biphenyl-3-yl, 4-trifluoromethoxy-phenyl, 5-chloro-2-methoxy-phenyl, naphthalen-1-yl, benzo[1,3]dioxol-5-ylmethyl, benzyl, diphenylmethyl, 1-phenyl-ethyl, 2-phenyl-ethyl, 2-pyridin-2-yl-ethyl, 3,4-dichloro-benzyl, 2,4-dichloro-benzyl, difluoromethoxy-benzyl, 2-chloro-benzyl, 4-chloro-benzyl, 2-methylsulfanyl-benzyl, 2-fluoro-benzyl, 3-fluoro-benzyl, 4-fluoro-benzyl, 2-trifluoromethyl-benzyl, 3-trifluoromethyl-benzyl, 2,4-difluoro-benzyl, 2,5-difluoro-benzyl, 2,6-difluoro-benzyl, 3,5-difluoro-benzyl, 4-chloro-2-fluoro-benzyl, (2-fluoro-phenyl)-ethyl, (3-fluoro-phenyl)-ethyl, (4-fluoro-phenyl)-ethyl, (4-chloro-phenyl)-ethyl, (2,6-dichloro-phenyl)-ethyl, naphthalene-1-ylmethyl, 1,2,3,4-tetrahydro-naphthalen-1-yl, indan-2-yl, or 2,2-diphenyl-ethyl; or a pharmaceutically acceptable salt thereof.

7. The compound according to claim 1 or 2, wherein $R^7$ and $R^8$, together with the nitrogen atom to which they are attached, form a dihydro-dibenzo[b,f]azocine, dihydro-indole, dihydroisoquinoline, dihydroquinoline, or dibenzoazepine ring;

or a pharmaceutically acceptable salt thereof.

8. The compound according to claim 1 or 2, wherein $R^7$ and $R^8$, together with the nitrogen atom to which they are attached, form a heterocyclic ring system which is 11,12-dihydro-6H-dibenzo[b,f]azocine-5-yl, 2,3-dihydro-indole-1-yl, 3,4-dihydro-1H-isoquinoline-2-yl, 3,4-dihydro-2H-quinoline-1-yl, 4-(4-fluoro-phenyl)-piperazine-1-yl, 6,11-dihydro-dibenzo[b,e]azepine-5-yl, 6,7-dimethoxy-3,4-dihydro-1H-isoquinoline-2-yl, 7-trifluoromethyl-3,4-dihydro-2H-quinoline-1-yl, dibenzo[b,f]azepine-5-yl, 1H,3H-benzo[d,e]isoquinoline-2-yl, 4-benzhydryl-piperazine-1-yl, or azocane-1-yl; or a pharmaceutically acceptable salt thereof.

9. The compound according to claim 1 or 2, wherein $R^6$ represents (R)-1-phenyl-ethyloxy or benzyloxy; or a pharmaceutically acceptable salt thereof.

10. The compound according to claim 1, wherein $R^1$, $R^2$, $R^3$, and $R^4$ independently represent hydrogen, alkyl, alkoxy, halogen, nitro, cyano, or trifluoromethyl;

$R^5$ represents hydrogen or alkyl; and $R^6$ represents benzyloxy, 1-phenyl-ethoxy or —$NR^7R^8$, wherein $R^7$ and $R^8$ independently represent hydrogen; alkyl; cyano-alkyl; alkenyl; phenyl optionally mono-substituted by halogen, alkyl, alkoxy, —$CF_3$, —$OCF_3$, phenyl-alkyl or phenyl-carbonyl; phenyl, di-substituted with halogen, alkoxy and phenyl; phenyl-alkyl optionally substituted in the alkyl chain by phenyl or optionally substituted in the phenyl ring by methylendioxy; phenyl-alkyl which is di-substituted by halogen or mono-substituted by halogen, —$CF_3$, —$OCHF_2$, alkyl or alkylsulfanyl; naphthyl; naphthyl-alkyl; cycloalkyl, wherein cycloalkyl refers to a cyclopentyl or cyclohexyl group, wherein said groups are optionally substituted with an annulated benzene ring; pyridyl-alkyl; or thienyl-alkyl; or $R^7$ and $R^8$, together with the nitrogen atom to which they are attached, form a heterocyclic 5-, 6-, 7-, or 8-membered ring system with one or two nitrogen heteroatoms and which ring system is optionally substituted with (i) one or two annulated benzene rings, wherein the benzene rings are unsubstituted or substituted with one or two substituents of alkoxy or —$CF_3$; (ii) a mono-substituted phenyl ring substituted with halogen; or (iii) phenyl-alkyl, wherein the alkyl chain is substituted with phenyl; or a pharmaceutically acceptable salt thereof.

11. The compound according to claim 1, wherein the compound is:

[3-methyl-3-(methyl-phenyl-carbamoyl)-1,2,3,4-tetrahydro-carbazol-9-yl]-acetic acid;
{3-[(3-chloro-phenyl)-methyl-carbamoyl]-3-methyl-1,2,3,4-tetrahydro-carbazol-9-yl}-acetic acid;
[3-(2,3-dihydro-indole-1-carbonyl)-1,2,3,4-tetrahydro-carbazol-9-yl]-acetic acid;
[3-methyl-3-(phenyl-thiophen-3-ylmethyl-carbamoyl)-1,2,3,4-tetrahydro-carbazol-9-yl]-acetic acid;
[3-(benzyl-phenyl-carbamoyl)-3-methyl-1,2,3,4-tetrahydro-carbazol-9-yl]-acetic acid;
{3-[(4-fluoro-phenyl)-methyl-carbamoyl]-3-methyl-1,2,3,4-tetrahydro-carbazol-9-yl}-acetic acid;
[3-(6,11-dihydro-dibenzo[b,e]azepine-5-carbonyl)-1,2,3,4-tetrahydro-carbazol-9-yl]-acetic acid;
[3-(benzyl-phenyl-carbamoyl)-1,2,3,4-tetrahydro-carbazol-9-yl]-acetic acid;
{3-[phenyl-(3-phenyl-propyl)-carbamoyl]-1,2,3,4-tetrahydro-carbazol-9-yl}-acetic acid;
[3-(2,3-dihydro-indole-1-carbonyl)-3-methyl-1,2,3,4-tetrahydro-carbazol-9-yl]-acetic acid;
{3-[(3,4-dichloro-phenyl)-methyl-carbamoyl]-3-methyl-1,2,3,4-tetrahydro-carbazol-9-yl}-acetic acid;
[3-(allyl-phenyl-carbamoyl)-3-methyl-1,2,3,4-tetrahydro-carbazol-9-yl]-acetic acid;
{3-[benzyl-((S)-1-phenyl-ethyl)-carbamoyl]-1,2,3,4-tetrahydro-carbazol-9-yl}-acetic acid;
{3-[methyl-(2-trifluoromethyl-phenyl)-carbamoyl]-1,2,3,4-tetrahydro-carbazol-9-yl}-acetic acid;
[3-(methyl-phenyl-carbamoyl)-6-trifluoromethyl-1,2,3,4-tetrahydro-carbazol-9-yl]-acetic acid;
[3-methyl-3-(methyl-o-tolyl-carbamoyl)-1,2,3,4-tetrahydro-carbazol-9-yl]-acetic acid;
[3-(2-benzyl-phenylcarbamoyl)-1,2,3,4-tetrahydro-carbazol-9-yl]-acetic acid;
[3-(dibenzo[b,f]azepine-5-carbonyl)-1,2,3,4-tetrahydro-carbazol-9-yl]-acetic acid;
[3-(ethyl-naphthalen-1-yl-carbamoyl)-1,2,3,4-tetrahydro-carbazol-9-yl]-acetic acid;
[3-(benzhydryl-methyl-carbamoyl)-1,2,3,4-tetrahydro-carbazol-9-yl]-acetic acid;
{3-methyl-3-[phenyl-(3-phenyl-propyl)-carbamoyl]-1,2,3,4-tetrahydro-carbazol-9-yl}-acetic acid;
[3-(ethyl-phenyl-carbamoyl)-1,2,3,4-tetrahydro-carbazol-9-yl]-acetic acid;
[3-(phenyl-thiophen-3-ylmethyl-carbamoyl)-1,2,3,4-tetrahydro-carbazol-9-yl]-acetic acid;
[3-(benzyl-isopropyl-carbamoyl)-1,2,3,4-tetrahydro-carbazol-9-yl]-acetic acid;
{3-[4-(4-fluoro-phenyl)-piperazine-1-carbonyl]-1,2,3,4-tetrahydro-carbazol-9-yl}-acetic acid;
[3-(benzyl-phenethyl-carbamoyl)-3-methyl-1,2,3,4-tetrahydro-carbazol-9-yl]-acetic acid;
[3-(3,4-dihydro-2H-quinoline-1-carbonyl)-1,2,3,4-tetrahydro-carbazol-9-yl]-acetic acid;
[3-(cyclohexyl-phenyl-carbamoyl)-1,2,3,4-tetrahydro-carbazol-9-yl]-acetic acid;
{3-[(3-chloro-phenyl)-methyl-carbamoyl]-1,2,3,4-tetrahydro-carbazol-9-yl}-acetic acid;
[3-methyl-3-(phenethyl-phenyl-carbamoyl)-1,2,3,4-tetrahydro-carbazol-9-yl]-acetic acid;
[3-(2-methoxy-phenylcarbamoyl)-1,2,3,4-tetrahydro-carbazol-9-yl]-acetic acid;
[3-(allyl-phenyl-carbamoyl)-1,2,3,4-tetrahydro-carbazol-9-yl]-acetic acid;
[3-(benzyl-phenethyl-carbamoyl)-1,2,3,4-tetrahydro-carbazol-9-yl]-acetic acid;
[3-(phenethyl-phenyl-carbamoyl)-1,2,3,4-tetrahydro-carbazol-9-yl]-acetic acid;
[3-(methyl-o-tolyl-carbamoyl)-1,2,3,4-tetrahydro-carbazol-9-yl]-acetic acid;
{3-[benzyl-((R)-1-phenyl-ethyl)-carbamoyl]-1,2,3,4-tetrahydro-carbazol-9-yl}-acetic acid;
[3-(methyl-phenyl-carbamoyl)-6-nitro-1,2,3,4-tetrahydro-carbazol-9-yl]-acetic acid;
[3-(7-trifluoromethyl-3,4-dihydro-2H-quinoline-1-carbonyl)-1,2,3,4-tetrahydro-carbazol-9-yl]-acetic acid;
[3-(3,4-dihydro-2H-quinoline-1-carbonyl)-3-methyl-1,2,3,4-tetrahydro-carbazol-9-yl]-acetic acid;
{3-[(4-fluoro-phenyl)-methyl-carbamoyl]-1,2,3,4-tetrahydro-carbazol-9-yl}-acetic acid;
[3-(4-methoxy-biphenyl-3-ylcarbamoyl)-1,2,3,4-tetrahydro-carbazol-9-yl]-acetic acid;
[6-fluoro-3-(methyl-phenyl-carbamoyl)-1,2,3,4-tetrahydro-carbazol-9-yl]-acetic acid;
[7-chloro-3-(methyl-phenyl-carbamoyl)-1,2,3,4-tetrahydro-carbazol-9-yl]-acetic acid;
[6-chloro-3-(methyl-phenyl-carbamoyl)-1,2,3,4-tetrahydro-carbazol-9-yl]-acetic acid;
{3-[methyl-(2-pyridin-2-yl-ethyl)-carbamoyl]-1,2,3,4-tetrahydro-carbazol-9-yl}-acetic acid;
{3-[(4-chloro-phenyl)-methyl-carbamoyl]-1,2,3,4-tetrahydro-carbazol-9-yl}-acetic acid;
{(R)-3-[(4-chloro-phenyl)-methyl-carbamoyl]-1,2,3,4-tetrahydro-carbazol-9-yl}-acetic acid;
[3-(isopropyl-phenyl-carbamoyl)-1,2,3,4-tetrahydro-carbazol-9-yl]-acetic acid;
{3-[(3,4-dichloro-phenyl)-methyl-carbamoyl]-1,2,3,4-tetrahydro-carbazol-9-yl}-acetic acid;
[3-(benzhydryl-carbamoyl)-1,2,3,4-tetrahydro-carbazol-9-yl]-acetic acid;
[6-cyano-3-(methyl-phenyl-carbamoyl)-1,2,3,4-tetrahydro-carbazol-9-yl]-acetic acid;
{3-[benzyl-((R)-1-phenyl-ethyl)-carbamoyl]-3-methyl-1,2,3,4-tetrahydro-carbazol-9-yl}-acetic acid;
[3-(2-benzyl-phenylcarbamoyl)-3-methyl-1,2,3,4-tetrahydro-carbazol-9-yl]-acetic acid;
[6-isopropyl-3-(methyl-phenyl-carbamoyl)-1,2,3,4-tetrahydro-carbazol-9-yl]-acetic acid;
[6-methyl-3-(methyl-phenyl-carbamoyl)-1,2,3,4-tetrahydro-carbazol-9-yl]-acetic acid;
[3-(11,12-dihydro-6H-dibenzo[b,f]azocine-5-carbonyl)-1,2,3,4-tetrahydro-carbazol-9-yl]-acetic acid;
[3-(methyl-phenethyl-carbamoyl)-1,2,3,4-tetrahydro-carbazol-9-yl]-acetic acid;
[6-bromo-3-(methyl-phenyl-carbamoyl)-1,2,3,4-tetrahydro-carbazol-9-yl]-acetic acid;
[3-(3-benzoyl-phenylcarbamoyl)-1,2,3,4-tetrahydro-carbazol-9-yl]-acetic acid;
(3-dibenzylcarbamoyl-1,2,3,4-tetrahydro-carbazol-9-yl)-acetic acid;
[3-(ethyl-naphthalen-1-yl-carbamoyl)-3-methyl-1,2,3,4-tetrahydro-carbazol-9-yl]-acetic acid;
{3-[(3-fluoro-phenyl)-methyl-carbamoyl]-1,2,3,4-tetrahydro-carbazol-9-yl}-acetic acid;
{3-[benzyl-(2-cyano-ethyl)-carbamoyl]-1,2,3,4-tetrahydro-carbazol-9-yl}-acetic acid;
(3-phenylcarbamoyl-1,2,3,4-tetrahydro-carbazol-9-yl)-acetic acid;
[3-(isopropyl-phenyl-carbamoyl)-3-methyl-1,2,3,4-tetrahydro-carbazol-9-yl]-acetic acid;

(3-diphenethylcarbamoyl-1,2,3,4-tetrahydro-carbazol-9-yl)-acetic acid;
[3-(benzhydryl-methyl-carbamoyl)-3-methyl-1,2,3,4-tetrahydro-carbazol-9-yl]-acetic acid;
[3-(5-chloro-2-methoxy-phenylcarbamoyl)-1,2,3,4-tetrahydro-carbazol-9-yl]-acetic acid;
[3-(butyl-phenyl-carbamoyl)-1,2,3,4-tetrahydro-carbazol-9-yl]-acetic acid;
{3-[ethyl-(4-trifluoromethoxy-phenyl)-carbamoyl]-1,2,3,4-tetrahydro-carbazol-9-yl}-acetic acid;
[3-(methyl-phenyl-carbamoyl)-1,2,3,4-tetrahydro-carbazol-9-yl]-acetic acid;
[6-iodo-3-(methyl-phenyl-carbamoyl)-1,2,3,4-tetrahydro-carbazol-9-yl]-acetic acid;
[6-methoxy-3-(methyl-phenyl-carbamoyl)-1,2,3,4-tetrahydro-carbazol-9-yl]-acetic acid;
9-carboxymethyl-2,3,4,9-tetrahydro-1H-carbazole-3-carboxylic acid (R)-1-phenyl-ethyl ester;
(S)-3-[(4-chloro-phenyl)-methyl-carbamoyl]-1,2,3,4-tetrahydro-carbazol-9-yl]-acetic acid;
[3-(6,11-dihydro-dibenzo[b,e]azepine-5-carbonyl)-3-methyl-1,2,3,4-tetrahydro-carbazol-9-yl]-acetic acid;
[8-chloro-3-(methyl-phenyl-carbamoyl)-1,2,3,4-tetrahydro-carbazol-9-yl]-acetic acid;
9-carboxymethyl-2,3,4,9-tetrahydro-1H-carbazole-3-carboxylic acid benzyl ester;
[3-(3,4-dihydro-1H-isoquinoline-2-carbonyl)-1,2,3,4-tetrahydro-carbazol-9-yl]-acetic acid;
[3-(6,7-dimethoxy-3,4-dihydro-1H-isoquinoline-2-carbonyl)-1,2,3,4-tetrahydro-carbazol-9-yl]-acetic acid;
{3-[(benzo[1,3[dioxol-5-ylmethyl)-carbamoyl]-1,2,3,4-tetrahydro-carbazol-9-yl}-acetic acid; and or
[3-(cyclohexyl-phenyl-carbamoyl)-3-methyl-1,2,3,4-tetrahydro-carbazol-9-yl]-acetic acid;
or a pharmaceutically acceptable salt thereof.

12. The compound according to claim 1, wherein the compound is:
{3-[benzyl-((R)-1-phenyl-ethyl)-carbamoyl]-6-fluoro-1,2,3,4-tetrahydro-carbazol-9-yl}-acetic acid;
[3-(benzhydryl-methyl-carbamoyl)-6-fluoro-1,2,3,4-tetrahydro-carbazol-9-yl]-acetic acid;
{3-[benzyl-((S)-1-phenyl-ethyl)-carbamoyl]-6-fluoro-1,2,3,4-tetrahydro-carbazol-9-yl}-acetic acid;
[3-(benzyl-phenethyl-carbamoyl)-6-fluoro-1,2,3,4-tetrahydro-carbazol-9-yl]-acetic acid;
[3-(2,3-dihydro-indole-1-carbonyl)-6-fluoro-1,2,3,4-tetrahydro-carbazol-9-yl]-acetic acid;
[3-(benzyl-isopropyl-carbamoyl)-6-fluoro-1,2,3,4-tetrahydro-carbazol-9-yl]-acetic acid;
[3-(azocane-1-carbonyl)-6-fluoro-1,2,3,4-tetrahydro-carbazol-9-yl]-acetic acid;
(3-phenylcarbamoyl-3-propyl-1,2,3,4-tetrahydro-carbazol-9-yl)-acetic acid;
[3-(methyl-phenyl-carbamoyl)-3-propyl-1,2,3,4-tetrahydro-carbazol-9-yl]-acetic acid;
[6-fluoro-3-(methyl-phenyl-carbamoyl)-1,2,3,4-tetrahydro-carbazol-9-yl]-acetic acid;
{6-fluoro-3-[4-(4-fluoro-phenyl)-piperazine-1-carbonyl]-1,2,3,4-tetrahydro-carbazol-9-yl}-acetic acid;
[3-(4-fluoro-phenylcarbamoyl)-3-propyl-1,2,3,4-tetrahydro-carbazol-9-yl]-acetic acid;
{6-fluoro-3-[4-(4-fluoro-phenyl)-piperazine-1-carbonyl]-1,2,3,4-tetrahydro-carbazol-9-yl}-acetic acid;
[3-(benzhydryl-methyl-carbamoyl)-6-fluoro-1,2,3,4-tetrahydro-carbazol-9-yl]-acetic acid;
(3-{benzyl-[2-(2,6-dichloro-phenyl)-ethyl]-carbamoyl}-1,2,3,4-tetrahydro-carbazol-9-yl)-acetic acid;
{3-[benzyl-((S)-1-phenyl-ethyl)-carbamoyl]-6-fluoro-1,2,3,4-tetrahydro-carbazol-9-yl}-acetic acid;
[3-(3-fluoro-phenylcarbamoyl)-3-methyl-1,2,3,4-tetrahydro-carbazol-9-yl]-acetic acid;
[3-(3,5-difluoro-benzylcarbamoyl)-3-methyl-1,2,3,4-tetrahydro-carbazol-9-yl]-acetic acid;
[3-(3-fluoro-phenylcarbamoyl)-3-propyl-1,2,3,4-tetrahydro-carbazol-9-yl]-acetic acid;
[3-(3-fluoro-phenylcarbamoyl)-1,2,3,4-tetrahydro-carbazol-9-yl]-acetic acid;
[3-(2,3-dihydro-indole-1-carbonyl)-3-ethyl-1,2,3,4-tetrahydro-carbazol-9-yl]-acetic acid;
[3-ethyl-3-(3-fluoro-phenylcarbamoyl)-1,2,3,4-tetrahydro-carbazol-9-yl]-acetic acid;
[3-ethyl-3-(4-fluoro-phenylcarbamoyl)-1,2,3,4-tetrahydro-carbazol-9-yl]-acetic acid;
[3-(2-chloro-benzylcarbamoyl)-3-methyl-1,2,3,4-tetrahydro-carbazol-9-yl]-acetic acid;
[3-(benzyl-phenethyl-carbamoyl)-6-fluoro-1,2,3,4-tetrahydro-carbazol-9-yl]-acetic acid;
[3-methyl-3-(2-methylsulfanyl-benzylcarbamoyl)-1,2,3,4-tetrahydro-carbazol-9-yl]-acetic acid;
(3-ethyl-3-phenylcarbamoyl-1,2,3,4-tetrahydro-carbazol-9-yl)-acetic acid;
{3-[benzyl-((R)-1-phenyl-ethyl)-carbamoyl]-6-fluoro-1,2,3,4-tetrahydro-carbazol-9-yl}-acetic acid;
[3-ethyl-3-(methyl-phenyl-carbamoyl)-1,2,3,4-tetrahydro-carbazol-9-yl]-acetic acid;
[3-(2-fluoro-phenylcarbamoyl)-3-propyl-1,2,3,4-tetrahydro-carbazol-9-yl]-acetic acid;
[3-(2-fluoro-phenylcarbamoyl)-3-methyl-1,2,3,4-tetrahydro-carbazol-9-yl]-acetic acid;
{3-methyl-3-[(naphthalen-1-ylmethyl)-carbamoyl]-1,2,3,4-tetrahydro-carbazol-9-yl}-acetic acid;
{3-[benzyl-(2-cyano-ethyl)-carbamoyl]-3-methyl-1,2,3,4-tetrahydro-carbazol-9-yl}-acetic acid;
[3-(benzyl-butyl-carbamoyl)-3-methyl-1,2,3,4-tetrahydro-carbazol-9-yl]-acetic acid;
[3-(4-fluoro-phenylcarbamoyl)-3-methyl-1,2,3,4-tetrahydro-carbazol-9-yl]-acetic acid;
[3-(4-fluoro-phenylcarbamoyl)-1,2,3,4-tetrahydro-carbazol-9-yl]-acetic acid;
[3-(2,4-dichloro-benzylcarbamoyl)-3-methyl-1,2,3,4-tetrahydro-carbazol-9-yl]-acetic acid;
(3-[benzyl-(4-fluoro-benzyl)-carbamoyl)-(4-tetrahydro-carbazol-9-yl]-acetic acid;
[3-(benzyl-isopropyl-carbamoyl)-6-fluoro-1,2,3,4-tetrahydro-carbazol-9-yl]-acetic acid;
[3-(2-difluoromethoxy-benzylcarbamoyl)-3-methyl-1,2,3,4-tetrahydro-carbazol-9-yl]-acetic acid;
[3-(2-fluoro-phenylcarbamoyl)-1,2,3,4-tetrahydro-carbazol-9-yl]-acetic acid;
[3-(benzyl-ethyl-carbamoyl)-3-methyl-1,2,3,4-tetrahydro-carbazol-9-yl]-acetic acid;
(3-methyl-3-phenylcarbamoyl-1,2,3,4-tetrahydro-carbazol-9-yl)-acetic acid;
[3-ethyl-3-(2-fluoro-phenylcarbamoyl)-1,2,3,4-tetrahydro-carbazol-9-yl]-acetic acid;
[3-(4-chloro-benzylcarbamoyl)-3-methyl-1,2,3,4-tetrahydro-carbazol-9-yl]-acetic acid;
(3-{benzyl-[2-(4-fluoro-phenyl)-ethyl]-carbamoyl}-1,2,3,4-tetrahydro-carbazol-9-yl)-acetic acid;
[3-methyl-3-(4-pentyl-benzylcarbamoyl)-1,2,3,4-tetrahydro-carbazol-9-yl]-acetic acid;
{3-[benzyl-(4-chloro-2-fluoro-benzyl)-carbamoyl]-1,2,3,4-tetrahydro-carbazol-9-yl}-acetic acid;

[3-(azocane-1-carbonyl)-6-fluoro-1,2,3,4-tetrahydro-carbazol-9-yl]-acetic acid;
[3-(2-fluoro-benzylcarbamoyl)-3-methyl-1,2,3,4-tetrahydro-carbazol-9-yl]-acetic acid;
[3-(3,4-dichloro-benzylcarbamoyl)-3-methyl-1,2,3,4-tetrahydro-carbazol-9-yl]-acetic acid;
(3-{benzyl-[2-(4-chloro-phenyl)-ethyl]-carbamoyl}-1,2,3,4-tetrahydro-carbazol-9-yl)-acetic acid;
[3-(2,4-difluoro-benzylcarbamoyl)-3-methyl-1,2,3,4-tetrahydro-carbazol-9-yl]-acetic acid;
[3-(benzhydryl-carbamoyl)-3-propyl-1,2,3,4-tetrahydro-carbazol-9-yl]-acetic acid;
{8-chloro-3-[4-(4-fluoro-phenyl)-piperazine-1-carbonyl]-1,2,3,4-tetrahydro-carbazol-9-yl}-acetic acid;
[8-chloro-3-(2,3-dihydro-indole-1-carbonyl)-1,2,3,4-tetrahydro-carbazol-9-yl]-acetic acid;
[3-(2,6-difluoro-benzylcarbamoyl)-3-methyl-1,2,3,4-tetrahydro-carbazol-9-yl]-acetic acid;
{3-[benzyl-(3-fluoro-benzyl)-carbamoyl]-1,2,3,4-tetrahydro-carbazol-9-yl}-acetic acid;
[3-(benzhydryl-methyl-carbamoyl)-8-chloro-1,2,3,4-tetrahydro-carbazol-9-yl]-acetic acid;
[3-(benzhydryl-carbamoyl)-3-methyl-1,2,3,4-tetrahydro-carbazol-9-yl]-acetic acid;
{3-[benzyl-(3-trifluoromethyl-benzyl)-carbamoyl]-1,2,3,4-tetrahydro-carbazol-9-yl}-acetic acid;
[3-(benzhydryl-carbamoyl)-3-ethyl-1,2,3,4-tetrahydro-carbazol-9-yl]-acetic acid;
[3-(4-fluoro-benzylcarbamoyl)-3-methyl-1,2,3,4-tetrahydro-carbazol-9-yl]-acetic acid;
(3-{benzyl-[2-(3-fluoro-phenyl)-ethyl]-carbamoyl}-1,2,3,4-tetrahydro-carbazol-9-yl)-acetic acid;
[3-(benzyl-isopropyl-carbamoyl)-3-methyl-1,2,3,4-tetrahydro-carbazol-9-yl]-acetic acid;
{3-[benzyl-(3,5-difluoro-benzyl)-carbamoyl]-1,2,3,4-tetrahydro-carbazol-9-yl}-acetic acid;
(3-{benzyl-[2-(2-fluoro-phenyl)-ethyl]-carbamoyl}-1,2,3,4-tetrahydro-carbazol-9-yl)-acetic acid;
{3-[benzyl-(2-trifluoromethyl-benzyl)-carbamoyl]-1,2,3,4-tetrahydro-carbazol-9-yl}-acetic acid;
{3-[benzyl-(4-fluoro-benzyl)-carbamoyl]-3-methyl-1,2,3,4-tetrahydro-carbazol-9-yl}-acetic acid;
[3-(1H,3H-benzo[de]isoquinoline-2-carbonyl)-3-methyl-1,2,3,4-tetrahydro-carbazol-9-yl]-acetic acid;
{3-[benzyl-(2,5-difluoro-benzyl)-carbamoyl]-1,2,3,4-tetrahydro-carbazol-9-yl}-acetic acid;
{3-[benzyl-(3-fluoro-benzyl-carbamoyl]-3-methyl-1,2,3,4-tetrahydro-carbazol-9-yl}-acetic acid;
{3-methyl-3-[(R)-(1,2,3,4-tetrahydro-naphthalen-1-yl)carbamoyl]-1,2,3,4-tetrahydro-carbazol-9-yl}-acetic acid;
{3-[benzyl-(3,5-difluoro-benzyl)-carbamoyl]-3-methyl-1,2,3,4-tetrahydro-carbazol-9-yl}-acetic acid;
[3-(benzyl-methyl-carbamoyl)-3-methyl-1,2,3,4-tetrahydro-carbazol-9-yl]-acetic acid;
(3-{benzyl-[2-(4-chloro-phenyl)-ethyl]-carbamoyl}-3-methyl-1,2,3,4-tetrahydro-carbazol-9-yl)-acetic acid;
(3-{benzyl-[2-(4-fluoro-phenyl)-ethyl]-carbamoyl}-3-methyl-1,2,3,4-tetrahydro-carbazol-9-yl)-acetic acid;
[8-chloro-3-(2,2-diphenyl-ethylcarbamoyl)-1,2,3,4-tetrahydro-carbazol-9-yl]-acetic acid;
{3-[benzyl-(3-trifluoromethyl-benzyl)-carbamoyl]-3-methyl-1,2,3,4-tetrahydro-carbazol-9-yl}-acetic acid;
[3-(4-benzhydryl-piperazine-1-carbonyl)-8-chloro-1,2,3,4-tetrahydro-carbazol-9-yl]-acetic acid;
{3-[benzyl-(4-chloro-2-fluoro-benzyl)-carbamoyl]-3-methyl-1,2,3,4-tetrahydro-carbazol-9-yl}-acetic acid;
[3-(benzhydryl-carbamoyl)-8-chloro-1,2,3,4-tetrahydro-carbazol-9-yl]-acetic acid;
[3-(2,3-dihydro-indole-1-carbonyl)-3-propyl-1,2,3,4-tetrahydro-carbazol-9-yl]-acetic acid;
(3-{benzyl-[2-(3-fluoro-phenyl)-ethyl]-carbamoyl}-3-methyl-1,2,3,4-tetrahydro-carbazol-9-yl)-acetic acid;
(3-{benzyl-[2-(2,6-dichloro-phenyl)-ethyl]-carbamoyl}-3-methyl-1,2,3,4-tetrahydro-carbazol-9-yl)-acetic acid;
{3-[benzyl-(2-trifluoromethyl-benzyl)-carbamoyl]-3-methyl-1,2,3,4-tetrahydro-carbazol-9-yl}-acetic acid;
{3-[benzyl-(2,5-difluoro-benzyl)-carbamoyl]-3-methyl-1,2,3,4-tetrahydro-carbazol-9-yl}-acetic acid;
[8-chloro-3-(indan-2-yl-carbamoyl)-1,2,3,4-tetrahydro-carbazol-9-yl]-acetic acid;
(3-{benzyl-[2-(2-fluoro-phenyl)-ethyl]-carbamoyl}-3-methyl-1,2,3,4-tetrahydro-carbazol-9-yl)-acetic acid;
[6-fluoro-3-((R)-1-phenyl-ethylcarbamoyl)-1,2,3,4-tetrahydro-carbazol-9-yl]-acetic acid;
[6-fluoro-3-((R)-1-phenyl-ethylcarbamoyl)-1,2,3,4-tetrahydro-carbazol-9-yl]-acetic acid;
[3-(benzyl-cyanomethyl-carbamoyl)-3-methyl-1,2,3,4-tetrahydro-carbazol-9-yl]-acetic acid;
[3-(2,3-dichloro-benzylcarbamoyl)-3-methyl-1,2,3,4-tetrahydro-carbazol-9-yl]-acetic acid; or
[7-methyl-3-(methyl-phenyl-carbamoyl)-1,2,3,4-tetrahydro-carbazol-9-yl]-acetic acid;

or a pharmaceutically acceptable salt thereof.

13. A pharmaceutical composition comprising the compound according to claim 1 or 2 and a pharmaceutically acceptable carrier.

14. A method of antagonizing a CRTH2 receptor, comprising administering to a subject in need thereof an antagonistic amount of the compound of claim 1, or a pharmaceutically acceptable salt thereof, wherein the antagonistic amount treats allergic asthma, rhinitis, allergic nephritis, conjunctivitis, atopic dermatitis, bronchial asthma, food allergy, anaphylactic shock, urticaria, eczema, itching, Churg-Strauss syndrome, or sinusitis.

* * * * *